(12) United States Patent
Pelcman et al.

(10) Patent No.: US 8,097,623 B2
(45) Date of Patent: Jan. 17, 2012

(54) INDOLES USEFUL IN THE TREATMENT OF INFLAMMATION

(75) Inventors: Benjamin Pelcman, Solna (SE); Kristofer Olofsson, Solna (SE); Martins Katkevics, Riga (LV); Vita Ozola, Riga (LV); Edgars Suna, Riga (LV); Ivars Kalvins, Riga (LV); Peteris Trapencieris, Riga (LV); Dace Katkevica, Riga (LV); Wesley Schaal, Solna (SE)

(73) Assignee: Biolipox AB, Solna (SE)

( * ) Notice: Subject to any disclaimer, the term of this patent is extended or adjusted under 35 U.S.C. 154(b) by 716 days.

(21) Appl. No.: 11/795,628

(22) PCT Filed: Dec. 22, 2005

(86) PCT No.: PCT/GB2005/004981
§ 371 (c)(1),
(2), (4) Date: Sep. 25, 2008

(87) PCT Pub. No.: WO2006/077366
PCT Pub. Date: Jul. 27, 2006

(65) Prior Publication Data
US 2009/0076004 A1  Mar. 19, 2009

(51) Int. Cl.
*A61K 31/5375* (2006.01)
*A61K 31/47* (2006.01)
*A61K 31/445* (2006.01)
*A61K 31/44* (2006.01)
*A61K 31/40* (2006.01)
*C07D 413/00* (2006.01)
*C07D 215/00* (2006.01)
*C07D 401/00* (2006.01)
*C07D 207/00* (2006.01)
*C07D 209/00* (2006.01)

(52) U.S. Cl. .............. 514/235.2; 514/314; 514/323; 514/339; 514/414; 544/143; 546/152; 546/201; 546/278.1; 548/440; 548/465; 548/492

(58) Field of Classification Search .......... 514/235.2, 514/314, 323, 339, 414; 544/143; 546/152, 546/201, 278.1; 548/440, 465, 492
See application file for complete search history.

(56) References Cited

U.S. PATENT DOCUMENTS

| | | |
|---|---|---|
| 4,960,786 A | 10/1990 | Salituro et al. |
| 5,081,138 A | 1/1992 | Gillard et al. |
| 5,081,145 A | 1/1992 | Guindon et al. |
| 5,189,054 A | 2/1993 | Salituro et al. |
| 5,236,916 A | 8/1993 | Weller, III et al. .......... 514/229.2 |
| 5,294,722 A | 3/1994 | Kim .............. 548/251 |
| 5,374,615 A | 12/1994 | Poss ............. 514/3.81 |
| 5,399,559 A | 3/1995 | Curtze et al. |
| 6,075,037 A | 6/2000 | Elliott et al. |
| 6,288,103 B1 | 9/2001 | Faull et al. |
| 6,337,344 B1 | 1/2002 | Defossa et al. |
| 6,353,007 B1 | 3/2002 | Sharma ............ 514/339 |
| 6,441,004 B1 | 8/2002 | Faull et al. |
| 6,479,527 B1 | 11/2002 | Barker et al. |
| 6,500,853 B1 | 12/2002 | Seehra et al. |
| 6,569,888 B1 | 5/2003 | Kettle et al. |
| 6,613,760 B1 | 9/2003 | Kettle et al. |
| 6,630,496 B1 | 10/2003 | Seehra et al. |
| 6,787,651 B2 | 9/2004 | Stolle et al. |
| 6,816,841 B1 | 11/2004 | Suginuma |
| 6,828,344 B1 | 12/2004 | Seehra et al. |
| 6,833,387 B1 | 12/2004 | Faull et al. |
| 6,916,841 B2 | 7/2005 | Seehra et al. |
| 7,169,925 B2 | 1/2007 | Merriman et al. |
| 7,705,023 B2 | 4/2010 | Olofsson et al. |
| 2003/0119830 A1 | 6/2003 | Faull et al. ............ 514/232.8 |
| 2006/0160879 A1 | 7/2006 | Olofsson et al. |
| 2008/0146616 A1 | 6/2008 | Olofsson et al. |
| 2008/0188473 A1 | 8/2008 | Olofsson et al. |
| 2008/0249091 A1 | 10/2008 | Pelcman et al. |
| 2009/0042949 A1 | 2/2009 | Pelcman et al. |
| 2009/0048285 A1 | 2/2009 | Pelcman et al. |

(Continued)

FOREIGN PATENT DOCUMENTS

EP    0 166 491 A2    1/1986

(Continued)

OTHER PUBLICATIONS

Dorwald F. A. (Side Reactions in Organic Synthesis, 2005, Wiley: VCH, Weinheim p. IX of Preface.).*
Dermer, Bio/Technology 12:320 (1994).
Freshney, Culture of Animal Cells, a manual of Basic Technique, Aln R. Liss, Inc., 1983, New York, pp. 3-4.
Rajur, S.B., et al., "Attempted synthesis of 9-substituted 34-amino-7-methyl (or phenyl)-5,6-dihydroindolo[1,2-α]quinoxalines as possible antiallergic agents", Indian Journal of Chemistry Section B; Organic Chemistry Including Medicinal Chemistry; 31B:551-554 (1992).
Roy, P.J., et al., "The Hemetsberger-Knitted Synthesis of Substituted 5-, 6-, and 7-Azaindoles", Synthesis, 16:2751-2757 (2005).
Lachance, N., et al., "Rapid and Efficient Microwave-Assisted Synthesis of 4-, 5-, 6- and 7-Azaindoles", Synthesis, 15:2571-2577 (2005).

(Continued)

*Primary Examiner* — Rebecca Anderson
*Assistant Examiner* — Samantha Shterengarts
(74) *Attorney, Agent, or Firm* — Morgan Lewis & Bockius LLP

(57) ABSTRACT

(I)

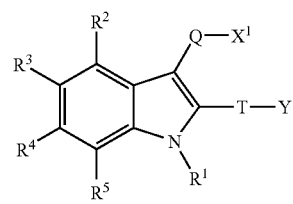

There is provided compounds of formula (I), wherein $X^1$, Q, T, Y, $R^1$, $R^2$, $R^3$, $R^4$ and $R^5$ have meanings given in the description, and pharmaceutically-acceptable salts thereof, which compounds are useful in the treatment of diseases in which inhibition of the activity of a member of the MAPEG family is desired and/or required, and particularly in the treatment of inflammation.

37 Claims, No Drawings

U.S. PATENT DOCUMENTS

| | | | |
|---|---|---|---|
| 2009/0069384 A1 | 3/2009 | Pelcman et al. | |

FOREIGN PATENT DOCUMENTS

| | | |
|---|---|---|
| EP | 0166591 | 1/1986 |
| EP | 0 275 667 A1 | 7/1988 |
| EP | 0 429 257 A2 | 5/1991 |
| EP | 0 275 667 B1 | 3/1992 |
| EP | 488 532 | 6/1992 |
| EP | 186 367 B1 | 3/1993 |
| EP | 0 535 924 A1 | 4/1993 |
| EP | 547 556 A1 | 6/1993 |
| EP | 986 666 | 12/1993 |
| EP | 0 639 573 A1 | 2/1995 |
| EP | 0 643 695 B1 | 8/1996 |
| EP | 0 483 881 B1 | 1/1998 |
| EP | 1001935 | 2/1999 |
| EP | 1 056 719 | 9/1999 |
| EP | 0985666 | 3/2000 |
| EP | 1 173 421 | 8/2000 |
| EP | 0 633 886 B1 | 10/2000 |
| EP | 1341761 | 4/2002 |
| EP | 1 159 269 B1 | 3/2003 |
| EP | 1 314 733 A1 | 5/2003 |
| EP | 1 003 504 B1 | 7/2003 |
| EP | 1 150 953 B1 | 9/2003 |
| EP | 1 042 287 B1 | 4/2005 |
| IT | 1303260 | 10/1998 |
| WO | WO 93/25524 A1 | 12/1993 |
| WO | WO 93/25546 A1 | 12/1993 |
| WO | WO 94/13662 A1 | 6/1994 |
| WO | WO 94/14434 A1 | 7/1994 |
| WO | WO 95/33748 A1 | 12/1995 |
| WO | WO 96/03377 A1 | 2/1996 |
| WO | WO 96/18393 A1 | 6/1996 |
| WO | WO 98/08818 A1 | 3/1998 |
| WO | WO 99/05104 | 2/1999 |
| WO | WO 99/07351 A2 | 2/1999 |
| WO | WO 99/07678 A1 | 2/1999 |
| WO | WO 99/15501 | 4/1999 |
| WO | WO 99/33800 A1 | 7/1999 |
| WO | WO 99/40914 A1 | 8/1999 |
| WO | WO 99/43434 A1 | 9/1999 |
| WO | WO 99/43651 A2 | 9/1999 |
| WO | WO 99/43654 A2 | 9/1999 |
| WO | WO 99/43672 | 9/1999 |
| WO | WO 99/43672 A1 | 9/1999 |
| WO | WO 00/46195 A1 | 8/2000 |
| WO | WO 00/46197 A1 | 8/2000 |
| WO | WO 00/46198 A1 | 8/2000 |
| WO | WO 00/46199 A2 | 8/2000 |
| WO | WO 01/00197 A2 | 1/2001 |
| WO | WO 01/30343 A1 | 5/2001 |
| WO | WO 01/32621 A1 | 5/2001 |
| WO | WO 02/06273 | 1/2002 |
| WO | WO 02/30895 A1 | 4/2002 |
| WO | WO 03/029212 | 4/2003 |
| WO | WO 03/044014 | 5/2003 |
| WO | WO 03/057670 | 7/2003 |
| WO | WO 2004/022537 | 3/2004 |
| WO | WO 2005/005415 | 1/2005 |
| WO | WO 2005/123673 | 12/2005 |
| WO | WO 2005/123674 | 12/2005 |
| WO | WO 2005/123675 | 12/2005 |
| WO | WO 2006/077364 | 7/2006 |
| WO | WO 2006/077365 | 7/2006 |
| WO | WO 2006/077367 | 7/2006 |
| WO | WO 2006/077401 | 7/2006 |
| WO | WO 2006/077412 | 7/2006 |

OTHER PUBLICATIONS

Dropinski, J.F., et al., "Synthesis and biological activities of novel aryl indole-2-carboxylic acid analogs as PPARγ partial agonists", Bioorganic & Medicinal Chemistry Letters, 15:5035-5038 (2005).

Sommen, G., et al., "Preparation of thieno[2,3-*b*]pyrroles starting from ketene-*N*,*S*-acetals", Tetrahedron, 59:1557-1564 (2003).

Sommen, G., et al., "An Easy Access to Variously Substituted Thieno[2,3-*b*]pyrroles by Using Isothiocyanates", Synlett., 11(10):1731-1734 (2001).

El-Hamed, M.K.A., et al., "Synthesis of Some Fused Thienopyrimidine Derivatives of Potential Antimicrobial Activity", Bulletin of the Faculty of Pharmacy (Cairo University), 39(3):11-21 (2001).

El-Shafei, A.K., et al., "Synthesis of Thienol(2,3-b)Thiophenes and Related Structures", Phosphorus, Sulfur and Silicon and the Related Elements, 73:15-25 (1992).

Kumar, P.R., e al., "Synthesis and biological evaluation of thiophene [3,2-*b*] pyrrole derivatives as potential anti-inflammatory agents", Bioorganic & Medicinal Chemistry, 12:1221-1230 (2004).

\* cited by examiner

INDOLES USEFUL IN THE TREATMENT OF INFLAMMATION

This is a §371 national phase conversion of PCT/GB2005/004981, filed Dec. 22, 2005, which claims priority benefit of U.S. Provisional Application No. 60/644,558, filed Jan. 19, 2005.

FIELD OF THE INVENTION

This invention relates to novel pharmaceutically-useful compounds, which compounds are useful as inhibitors of enzymes belonging to the membrane-associated proteins in the eicosanoid and glutathione metabolism (MAPEG) family. Members of the MAPEG family include the microsomal prostaglandin E synthase-1 (mPGES-1), 5-lipoxygenase-activating protein (FLAP), leukotriene $C_4$ synthase and microsomal glutathione S-transferases (MGST1, MGST2 and MGST3). The compounds are of potential utility in the treatment of inflammatory diseases including respiratory diseases. The invention also relates to the use of such compounds as medicaments, to pharmaceutical compositions containing them, and to synthetic routes for their production.

BACKGROUND OF THE INVENTION

There are many diseases/disorders that are inflammatory in their nature. One of the major problems associated with existing treatments of inflammatory conditions is a lack of efficacy and/or the prevalence of side effects (real or perceived).

Inflammatory diseases that affect the population include asthma, inflammatory bowel disease, rheumatoid arthritis, osteoarthritis, rhinitis, conjunctivitis and dermatitis.

Inflammation is also a common cause of pain. Inflammatory pain may arise for numerous reasons, such as infection, surgery or other trauma. Moreover, several diseases including malignancies and cardioavascular diseases are known to have inflammatory components adding to the symptomatology of the patients.

Asthma is a disease of the airways that contains elements of both inflammation and bronchoconstriction. Treatment regimens for asthma are based on the severity of the condition. Mild cases are either untreated or are only treated with inhaled β-agonists which affect the bronchoconstriction element, whereas patients with more severe asthma typically are treated regularly with inhaled corticosteroids which to a large extent are anti-inflammatory in their nature.

Another common disease of the airways with inflammatory and bronchoconstrictive components is chronic obstructive pulmonary disease (COPD). The disease is potentially lethal, and the morbidity and mortality from the condition is considerable. At present, there is no known pharmacological treatment capable of changing the course of the disease.

The cyclooxygenase (COX) enzyme exists in two forms, one that is constitutively expressed in many cells and tissues (COX-1), and one that is induced by pro-inflammatory stimuli, such as cytokines, during an inflammatory response (COX-2).

COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects.

$PGE_2$ in particular is known to be a strong pro-inflammatory mediator, and is also known to induce fever and pain.

Consequently, numerous drugs have been developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$.

However, the inhibition of COXs has the disadvantage that it results in the reduction of the formation of all metabolites of arachidonic acid, some of which are known to have beneficial properties. In view of this, drugs which act by inhibition of COXs are therefore known/suspected to cause adverse biological effects. For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that inhibits (preferably selectively) the transformation of $PGH_2$ to the pro-inflammatory mediator $PGE_2$ might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described.

The leukotrienes (LTs) are formed from arachidonic acid by a set of enzymes distinct from those in the COX/PGES pathway. Leukotriene B4 is known to be a strong proinflammatory mediator, while the cysteinyl-containing leukotrienes $C_4$, $D_4$ and $E_4$ (CysLTs) are mainly very potent bronchoconstrictors and have thus been implicated in the pathobiology of asthma. The biological activities of the CysLTs are mediated through two receptors designated $CysLT_1$ and $CysLT_2$. As an alternative to steroids, leukotriene receptor antagonists (LTRas) have been developed in the treatment of asthma. These drugs may be given orally, but do not control inflammation satisfactorily. The presently used LTRas are highly selective for $CysLT_1$. It may be hypothesised that better control of asthma, and possibly also COPD, may be attained if the activity of both of the CysLT receptors could be reduced. This may be achieved by developing unselective LTRas, but also by inhibiting the activity of proteins, e.g. enzymes, involved in the synthesis of the CysLTs. Among these proteins, 5-lipoxygenase, 5-lipoxygenase-activating protein (FLAP), and leukotriene $C_4$ synthase may be mentioned. A FLAP inhibitor would also decrease the formation of the proinflammatory $LTB_4$.

mPGES-1, FLAP and leukotriene $C_4$ synthase belong to the membrane-associated proteins in the eicosanoid and glutathione metabolism (MAPEG) family. Other members of this family include the microsomal glutathione S-transferases (MGST1, MGST2 and MGST3). For a review, c.f. P.-J. Jacobsson et al in *Am. J. Respir. Crit. Care Med.* 161, S20 (2000). It is well known that compounds prepared as antagonists to one of the MAPEGs may also exhibit inhibitory activity towards other family members, c.f. J. H Hutchinson et al in *J. Med. Chem.* 38, 4538 (1995) and D. Claveau et al in *J. Immunol.* 170, 4738 (2003). The former paper also describes that such compounds may also display notable cross-reactivity with proteins in the arachidonic acid cascade that do not belong to the MAPEG family, e.g. 5-lipoxygenase.

Thus, agents that are capable of inhibiting the action of mPGES-1, and thus reducing the formation of the specific arachidonic acid metabolite $PGE_2$, are likely to be of benefit in the treatment of inflammation. Further, agents that are capable of inhibiting the action of the proteins involved in the synthesis of the leukotrienes are also likely to be of benefit in the treatment of asthma and COPD.

PRIOR ART

Indole-based compounds have been disclosed in international patent applications WO 96/03377, WO 01/00197, WO 03/044014 and WO 03/057670, U.S. Pat. Nos. 5,189,054, 5,294,722 and 4,960,786 and European patent applications EP 429 257, EP 483 881, EP 547 556, EP 639 573 and EP 1 314 733. In particular European patent application EP 488 532 and U.S. Pat. Nos. 5,236,916 and 5,374,615 disclose 1(N)-phenylindole-2-carboxylates as antihypertensive agents and as chemical intermediates. However, none of these documents disclose or suggest the use of such compounds in the treatment of inflammation.

Indoles have also been disclosed for potential use in the treatment of inflammation in international patent applications WO 99/43672, WO 98/08818, WO 99/43654, WO 99/43651, WO 99/05104 and WO 03/029212, European patent application EP 986 666 and U.S. Pat. Nos. 6,500,853 and 6,630,496. However, there is no specific disclosure in any of these documents of indole-2-carboxylates in which an aromatic group is directly attached via the indole nitrogen.

International patent application WO 01/30343, and European patent application EP 186 367, also mention indoles for potential use as PPAR-γ binding agents, and in the treatment of inflammation, respectively. However, these documents do not mention or suggest compounds in which the benzenoid moiety of the indole is substituted with an aromatic ring.

Various 1(N)-benzylindole-2-carboxylates and derivatives thereof are known from international patent applications WO 99/33800 as Factor Xa inhibitors; WO 99/07678, WO 99/07351, WO 00/46198, WO 00/46197, WO 00/46195 and WO 00/46199 as inhibitors of MCP-1; international patent application WO 96/18393 as inhibitors of IL-8; international patent applications WO 93/25546 and WO 94/13662, European patent application EP 535 924 A1 and U.S. Pat. No. 5,081,138 as inhibitors of leukotriene biosynthesis; international patent application WO 02/30895 as PPAR-γ binding agents; and European patent application EP 166 591 as prostaglandin antagonists. Further, international patent application WO 2005/005415 discloses such compounds for use as inhibitors of mPGES and this in the treatment of inflammation. However, there is no specific disclosure in any of these documents of indole-2-carboxylates in which an aromatic group is directly attached via the indole nitrogen.

Unpublished international patent applications PCT/GB2005/002404, PCT/GB2005/002391 and PCT/GB2005/002396 disclose indoles for use as inhibitors of mPGES and thus in the treatment of inflammation. However, there is no specific disclosure in any of these documents of compounds that are substituted in the 3-position of the indoe ring with a carbocyclic acid, or equivalent, group.

Finally, international patent application WO 94/14434 discloses structurally similar indoles as endothelin receptor antagonists. There is no specific disclosure in this document of compounds with indole-2-carboxylates in which an aromatic group is directly attached via the indole nitrogen, nor of compounds in which aromatic and heteroaromatic moieties are attached to the benzenoid part of the indole via a linking group.

DISCLOSURE OF THE INVENTION

According to the invention there is provided a compound of formula I,

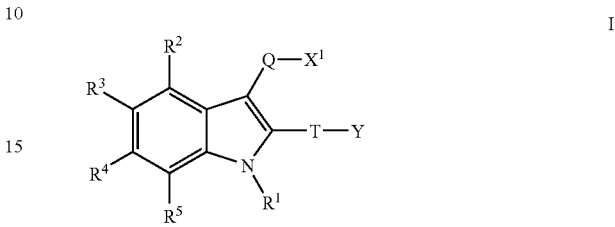

I wherein
one of the groups $R^2$, $R^3$, $R^4$ and $R^5$ represents -D-E and:
a) the other groups are independently selected from hydrogen, $G^1$, an aryl group, a heteroaryl group (which latter two groups are optionally substituted by one or more substituents selected from A), $C_{1-8}$ alkyl and a heterocycloalkyl group (which latter two groups are optionally substituted by one or more substituents selected from $G^1$ and/or $Z^1$); and/or
b) any two other groups which are adjacent to each other are optionally linked to form, along with two atoms of the essential benzene ring in the compound of formula I, a 3- to 8-membered ring, optionally containing 1 to 3 heteroatoms, which ring is itself optionally substituted by one or more substituents selected from halo, $—R^6$, $—OR^6$ and $=O$;
D represents a single bond, $—O—$, $—C(R^7)(R^8)—$, $C_{2-4}$ alkylene, $—C(O)—$ or $—S(O)_m—$;
$R^1$ and E independently represent an aryl group or a heteroaryl group, both of which groups are optionally substituted by one or more substituents selected from A;
$R^7$ and $R^8$ independently represent H, halo or $C_{1-6}$ alkyl, which latter group is optionally substituted by halo, or $R^7$ and $R^8$ may together form, along with the carbon atom to which they are attached, a 3- to 6-membered ring, which ring optionally contains a heteroatom and is optionally substituted by one or more substituents selected from halo and $C_{1-3}$ alkyl, which latter group is optionally substituted by one or more halo substituents;
Q represents a single bond, or a $C_{1-8}$ alkylene or $C_{2-8}$ heteroalkylene chain, both of which latter two groups optionally contain one or more unsaturations (for example double or triple bonds) and are optionally substituted by one or more substituents selected from $G^1$ and/or $Z^1$;
$X^1$ represents:
(a) $—C(O)OR^{9a}$, $—C(O)N(R^{10b})R^{9b}$, $—C(O)N(H)C(=NR^{9c})N(R^{10d})R^{9d}$; $—C(O)N(H)CN$, $—S(O)_3R^{9e}$, $—P(O)(OR^{9f})_2$, $—P(O)(OR^{9g})N(R^{10h})R^{9h}$, $—P(O)(N(R^{10i})R^{9i})_2$, $—B(OR^{9j})_2$, $—C(O)N(H)S(O)_2R^{11}$ or, provided that T does not represent a single bond when Y represents $—C(O)OR^{9a}$, unsubstituted tetrazolyl;
(b) an aryl group or a heteroaryl group, both of which are substituted by at least one substituent selected from $X^2$, and one or more further optional substituents selected from A; or
(c) a heterocycloalkyl group substituted by at least one substituent selected from $X^2$, and one or more further optional substituents selected from $G^1$ and/or $Z^1$;

$X^2$ represents —C(O)OR$^{9a}$, —C(O)N(R$^{10b}$)R$^{9b}$, —C(O)N(H)C(=NR$^{9c}$)N(R$^{10d}$)R$^{9d}$; —C(O)N(H)CN, —S(O)$_3$R$^{9e}$, —P(O)(OR$^{9f}$)$_2$, —P(O)(OR$^{9g}$)N(R$^{10h}$)R$^{9h}$, —P(O)(N(R$^{10i}$)R$^{9i}$)$_2$, —B(OR$^{9y}$)$_2$, —C(O)N(H)S(O)$_2$R$^{11}$ or unsubstituted tetrazolyl;

T represents:
(a) a single bond;
(b) a $C_{1-8}$ alkylene or a $C_{2-8}$ heteroalkylene chain, both of which latter two groups:
  (i) optionally contain one or more unsaturations (for example double or triple bonds);
  (ii) are optionally substituted by one or more substituents selected from $G^1$ and/or $Z^1$; and/or
  (iii) may comprise an additional 3- to 8-membered ring formed between any one or more (e.g. one or two) members of the $C_{1-8}$ alkylene or $C_{2-8}$ heteroalkylene chain, which ring optionally contains 1 to 3 heteroatoms and/or 1 to 3 unsaturations (for example double or triple bonds) and which ring is itself optionally substituted by one or more substituents selected from $G^1$ and/or $Z^1$;
(c) an arylene group or a heteroarylene group, both of which groups are optionally substituted by one or more substituents selected from A; or
(d) -T$^1$-W$^1$-T$^2$-;
one of T$^1$ and T$^2$ represents a $C_{1-8}$ alkylene or a $C_{2-8}$ heteroalkylene chain, both of which latter two groups:
(i) optionally contain one or more unsaturations (for example double or triple bonds);
(ii) are optionally substituted by one or more substituents selected from $G^1$ and/or $Z^1$; and/or
(iii) may comprise an additional 3- to 8-membered ring formed between any one or more (e.g. one or two) members of the $C_{1-8}$ alkylene or $C_{2-8}$ heteroalkylene chain, which ring optionally contains 1 to 3 heteroatoms and/or 1 to 3 unsaturations (for example double or triple bonds) and which ring is itself optionally substituted by one or more substituents selected from $G^1$ and/or $Z^1$;
and the other represents an arylene group or a heteroarylene group, both of which groups are optionally substituted by one or more substituents selected from A;

$W^1$ represents —O— or —S(O)$_m$—;
m represents, on each occasion when mentioned above, 0, 1 or 2;
Y represents C(H)(CF$_3$)OH, —C(O)CF$_3$, —C(OH)$_2$CF$_3$, —C(O)OR$^{9a}$, —S(O)$_3$R$^{9e}$, —P(O)(OR$^{9f}$)$_2$, —P(O)(OR$^{9g}$)N(R$^{10h}$)R$^{9h}$, —P(O)(—N(R$^{10i}$)R$^{9i}$)$_2$, —B(OR$^{9y}$)$_2$, —C(CF$_3$)$_2$OH, —S(O)$_2$N(R$^{10z}$)R$^{9z}$ or any one of the following groups:

$R^6$, $R^{9a}$ to $R^{9z}$, $R^{10b}$, $R^{10d}$, $R^{10h}$, $R^{10i}$, $R^{10j}$ and $R^{10z}$ independently represent, on each occasion when mentioned above:
I) hydrogen;
II) an aryl group or a heteroaryl group, both of which are optionally substituted by one or more substituents selected from B; or
III) $C_{1-8}$ alkyl or a heterocycloalkyl group, both of which are optionally substituted by one or more substituents selected from $G^1$ and/or $Z^1$; or
any pair of $R^{9a}$ to $R^{9y}$ and $R^{10b}$, $R^{10d}$, $R^{10h}$, $R^{10i}$ or $R^{10j}$, may be linked together to form, along with the atom(s) to which they are attached, a 3- to 8-membered ring, optionally containing 1 to 3 heteroatoms and/or 1 to 3 double bonds, which ring is optionally substituted by one or more substituents selected from $G^1$ and/or $Z^1$;

$R^{11}$ represents:
I) an aryl group or a heteroaryl group, both of which are optionally substituted by one or more substituents selected from B; or
II) $C_{1-8}$ alkyl or a heterocycloalkyl group, both of which are optionally substituted by one or more substituents selected from $G^1$ and/or $Z^1$;

A represents, on each occasion when mentioned above:
I) an aryl group or a heteroaryl group, both of which are optionally substituted by one or more substituents selected from B;
II) $C_{1-8}$ alkyl or a heterocycloalkyl group, both of which are optionally substituted by one or more substituents selected from $G^1$ and/or $Z^1$; or
III) a $G^1$ group;

$G^1$ represents, on each occasion when mentioned above, halo, cyano, —N$_3$, —NO$_2$, —ONO$_2$ or -A$^1$-R$^{12a}$;
wherein A$^1$ represents a single bond or a spacer group selected from —C(O)A$^2$-, —S(O)$_2$A$^3$-, N(R$^{13a}$)A$^4$ or —OA$^5$-, in which:
A$^2$ represents a single bond, —O—, —N(R$^{13b}$)— or —C(O)—;
A$^3$ represents a single bond, —O— or —N(R$^{13c}$)—;
A$^4$ and A$^5$ independently represent a single bond, —C(O)—, —C(O)N(R$^{13d}$)—, —C(O)O—, —S(O)$_2$— or —S(O)$_2$N(R$^{13e}$)—;

$Z^1$ represents, on each occasion when mentioned above, =O, =S, =NOR$^{12b}$, =NS(O)$_2$N(R$^{13f}$)R$^{12c}$, =NCN or =C(H)NO$_2$;

B represents, on each occasion when mentioned above:
I) an aryl group or a heteroaryl group, both of which are optionally substituted by one or more substituents selected from $G^2$;
II) $C_{1-8}$ alkyl or a heterocycloalkyl group, both of which are optionally substituted by one or more substituents selected from $G^2$ and/or $Z^2$; or
III) a $G^2$ group;
$G^2$ represents, on each occasion when mentioned above, halo, cyano, $-N_3$, $-NO_2$, $-ONO_2$ or $-A^6-R^{14a}$;
wherein $A^6$ represents a single bond or a spacer group selected from $-C(O)A^7-$, $-S(O)_2A^8-$, $-N(R^{15a})A^9-$ or $-OA^{10}-$, in which:
$A^7$ represents a single bond, $-O-$, $-N(R^{15b})-$ or $-C(O)-$;
$A^8$ represents a single bond, $-O-$ or $-N(R^{15c})-$;
$A^9$ and $A^{10}$ independently represent a single bond, $-C(O)-$, $-C(O)N(R^{15d})-$, $-C(O)O-$, $-S(O)_2-$ or $-S(O)_2N(R^{15e})-$;
$Z^2$ represents, on each occasion when mentioned above, $=O$, $=S$, $=NOR^{14b}$, $=NS(O)_2N(R^{15f})R^{14c}$, $=NCN$ or $=C(H)NO_2$;
$R^{12a}$, $R^{12b}$, $R^{12c}$, $R^{13a}$, $R^{13b}$, $R^{13c}$, $R^{13d}$, $R^{13e}$, $R^{13f}$, $R^{14a}$, $R^{14b}$, $R^{14c}$, $R^{15a}$, $R^{15b}$, $R^{15c}$, $R^{15d}$, $R^{15e}$ and $R^{15f}$ are independently selected from:
i) hydrogen;
ii) an aryl group or a heteroaryl group, both of which are optionally substituted by one or more substituents selected from $G^3$;
iii) $C_{1-8}$ alkyl or a heterocycloalkyl group, both of which are optionally substituted by $G^3$ and/or $Z^3$; or
any pair of $R^{12a}$ to $R^{12c}$ and $R^{13a}$ to $R^{13f}$, and/or $R^{14a}$ to $R^{14c}$ and $R^{15a}$ to $R^{15f}$, may, for example when present on the same or on adjacent atoms, be linked together to form with those, or other relevant, atoms a further 3- to 8-membered ring, optionally containing 1 to 3 heteroatoms and/or 1 to 3 double bonds, which ring is optionally substituted by one or more substituents selected from $G^3$ and/or $Z^3$;
$G^3$ represents, on each occasion when mentioned above, halo, cyano, $-N_3$, $-NO_2$, $-ONO_2$ or $-A^{11}-R^{16a}$;
wherein $A^{11}$ represents a single bond or a spacer group selected from $-C(O)A^{12}-$, $-S(O)A^{13}$, $-N(R^{17a})A^{14}$ or $-OA^{15}-$, in which:
$A^{12}$ represents a single bond, $-O-$, $-N(R^{17b})-$ or $-C(O)-$;
$A^{13}$ represents a single bond, $-O-$ or $-N(R^{17c})-$;
$A^{14}$ and $A^{15}$ independently represent a single bond, $-C(O)-$, $-C(O)N(R^{17d})-$, $-C(O)O-$, $-S(O)_2-$ or $-S(O)_2N(R^{17e})-$;
$Z^3$ represents, on each occasion when mentioned above, $=O$, $=S$, $=NOR^{16b}$, $=NS(O)_2N(R^{17f})R^{16c}$, $=NCN$ or $=C(H)NO_2$;
$R^{16a}$, $R^{16b}$, $R^{16c}$, $R^{17a}$, $R^{17b}$, $R^{17c}$, $R^{17d}$, $R^{17e}$ and $R^{17f}$ are independently selected from:
i) hydrogen;
ii) $C_{1-6}$ alkyl or a heterocycloalkyl group, both of which groups are optionally substituted by one or more substituents selected from halo, $C_{1-4}$ alkyl, $-N(R^{18a})R^{19a}$, $-OR^{18b}$ and $=O$; and
iii) an aryl or heteroaryl group, both of which are optionally substituted by one or more substituents selected from halo, $C_{1-4}$ alkyl, $-N(R^{18c})R^{19b}$ and $-OR^{18d}$; or
any pair of $R^{16a}$ to $R^{16c}$ and $R^{17a}$ to $R^{17f}$ may, for example when present on the same or on adjacent atoms, be linked together to form with those, or other relevant, atoms a further 3- to 8-membered ring, optionally containing 1 to 3 heteroatoms and/or 1 to 3 double bonds, which ring is optionally substituted by one or more substituents selected from halo, $C_{1-4}$ alkyl, $-N(R^{18e})R^{19c}$, $-OR^{18f}$ and $=O$;
$R^{18a}$, $R^{18b}$, $R^{18c}$, $R^{18d}$, $R^{18e}$, $R^{18f}$, $R^{19a}$, $R^{19b}$ and $R^{19c}$ are independently selected from hydrogen and $C_{1-4}$ alkyl, which latter group is optionally substituted by one or more halo groups;
or a pharmaceutically-acceptable salt thereof,
which compounds and salts are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. Factional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise specified, $C_{1-q}$ alkyl, and $C_{1-q}$ alkylene, groups (where q is the upper limit of the range) defined herein may be straight-chain or, when there is a sufficient number (i.e. a minimum of two or three, as appropriate) of carbon atoms, be branched-chain, and/or cyclic (so forming, in the case of alkyl, a $C_{3-q}$-cycloalkyl group or, in the case of alkylene, a $C_{3-q}$ cycloalkylene group). Further, when there is a sufficient number (i.e. a minimum of four) of carbon atoms, such groups may also be part cyclic. When one of the groups $R^2$ to $R^5$ represents -D-E, and any one of the other groups are $C_{1-8}$ alkyl, then it is preferred that such an alkyl group is not cyclic. Such alkyl and alklylene groups may also be saturated or, when there is a sufficient number (i.e. a minimum of two) of carbon atoms, be unsaturated (forming, for example, in the case of alkyl, a $C_{2-q}$ alkenyl or a $C_{2-q}$ alkynyl group or, in the case of alkylene, a $C_{2-q}$ alkenylene or a $C_{2-q}$ alkynylene group).

$C_{3-q}$ cycloalkyl groups (where q is the upper limit of the range) that may be mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double or triple bonds (forming for example a $C_{3-q}$ cycloalkenyl or a $C_{8-q}$ cycloalkynyl group). Substituents may be attached at any point on the cycloalkyl group. Further in the case where the substituent is another cyclic compound, then the cyclic substituent may be attached through a single atom on the cycloalkyl group, forming a so-called "spiro"-compound.

$C_{2-8}$ heteroalkylene chains include $C_{2-8}$ alkylene chains that are interrupted by one or more heteroatom groups selected from —O—, —S— or —N($R^{20}$)— in which $R^{20}$ represents $C_{1-4}$ alkyl optionally substituted by one or more halo (e.g. fluoro) groups.

The term "halo", when used herein, includes fluoro, chloro, bromo and iodo.

Heterocycloalkyl groups that may be mentioned include non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten). Further, such heterocycloalkyl groups may be saturated or unsaturated containing one or more double and/or triple bonds, forming for example a $C_{2-q}$ heterocycloalkenyl (where q is the upper limit of the range) or a $C_{3-q}$ heterocycloalkynyl group. $C_{2-q}$ heterocycloalkyl groups that may be mentioned include 7-azabicyclo[2.2.1]heptanyl, 6-azabicyclo[3.1.1]hept-anyl, 6-azabicyclo[3.2.1]-octanyl, 8-azabicyclo[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo[3.2.1]octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the other substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form.

For the avoidance of doubt, the term "bicyclic", when employed in the context of cycloalkyl and heterocycloalkyl groups refers to such groups in which the second ring is formed between two adjacent atoms of the first ring. The term "bridged", when employed in the context of cycloalkyl or heterocycloalkyl groups refers to monocyclic or bicyclic groups in which two non-adjacent atoms are linked by either an alkylene or heteroalkylene chain (as appropriate).

Aryl groups that may be mentioned include $C_{6-14}$ (such as $C_{6-13}$ (e.g. $C_{6-10}$)) aryl groups. Such groups may be monocyclic, bicyclic or tricyclic and have between 6 and 14 ring carbon atoms, in which at least one ring is aromatic. $C_{6-14}$ aryl groups include phenyl, naphthyl and the like, such as 1,2,3,4-tetrahydronaphthyl, indanyl, indenyl and fluorenyl. The point of attachment of aryl groups may be via any atom of the ring system. However, when aryl groups are bicyclic or tricyclic, they are linked to the rest of the molecule via an aromatic ring.

Heteroaryl groups that may be mentioned include those which have between 5 and 14 (e.g. 10) members. Such groups may be monocyclic, bicyclic or tricyclic, provided that at least one of the rings is aromatic and wherein at least one (e.g. one to four) of the atoms in the ring system is other than carbon (i.e. a heteroatom). Heterocyclic groups that may be mentioned include benzothiadiazolyl (including 2,1,3-benzothiadiazolyl), isothiochromanyl and, more preferably, acridinyl, benzimidazolyl, benzodioxanyl, benzodioxepinyl, benzodioxolyl (including 1,3-benzodioxolyl), benzofuranyl, benzofurazanyl, benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isoxazolyl, naphthyridinyl (including 1,6-naphthyridinyl or, preferably, 1,5-naphthyridinyl and 1,8-napthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form.

Heteroatoms that may be mentioned include phosphorus, silicon, boron, tellurium, selenium and, preferably, oxygen, nitrogen and sulphur.

For the avoidance of doubt, "heterocycloalkylene", "arylene", "heteroarylene" and "cycloalkylene" groups as defined herein comprise "linking" groups in which a heterocycloalkyl, an aryl, a heteroaryl, or a cycloalkyl, group (each of which are as defined hereinbefore), serves the purpose of linking two different parts of a compound of the invention together, in exactly the same way as an alkylene group can be said to constitute a "linking" (i.e. a divalent) alkyl group. Thus, for example, a phenyl group that serves the purpose of linking two substituents within, or parts of, a compound of the invention together would be classified in the context of the present invention as a "phenylene" group.

For the avoidance of doubt, in cases in which the identity of two or more substituents in a compound of the invention may be the same, the actual identities of the respective substituents are not in any way interdependent. For example, in the situation in which $R^1$ and E are both aryl groups substituted by one or more $C_{1-8}$ allyl groups, the alkyl groups in question may be the same or different. Similarly, when groups are substituted by more than one substituent as defined herein, the identities of those individual substituents are not to be regarded as being interdependent. For example, when E and/or $R^1$ represents e.g. an aryl group substituted by $G^1$ in addition to, for example, $C_{1-8}$ allyl, which latter group is substituted by $G^1$, the identities of the two $G^1$ groups are not to be regarded as being interdependent.

For the avoidance of doubt, when a term such as "$R^{9a}$ to $R^{9z}$" is employed herein, this will be understood by the skilled person to mean $R^{9a}$, $R^{9b}$, $R^{9c}$, $R^{9d}$, $R^{9e}$, $R^{9f}$, $R^{9g}$, $R^{9h}$, $R^{9i}$, $R^{9j}$, $R^{9k}$, $R^{9m}$, $R^{9n}$, $R^{9p}$, $R^{9q}$, $R^{9r}$, $R^{9s}$, $R^{9t}$, $R^{9u}$, $R^{9v}$, $R^{9w}$, $R^{9x}$, $R^{9y}$ and $R^{9z}$ inclusively.

Any pair of $R^{9a}$ to $R^{9z}$ and $R^{10b}$, $R^{10d}$, $R^{10h}$, $R^{10i}$, $R^{10j}$ and $R^{10z}$, may be linked together to form a ring as hereinbefore defined. Thus $R^{9a}$ to $R^{9z}$, $R^{10b}$, $R^{10d}$, $R^{10h}$, $R^{10i}$, $R^{10j}$ and $R^{10z}$ groups (e.g. $R^{9d}$ and $R^{10d}$) may be attached to a single nitrogen atom which also forms part of the ring, or two $R^{9a}$ to $R^{9z}$ (e.g. two $R^{9f}$) groups may be attached to different oxygen atoms (for example in a 1,3-relationship) all of which may form part of the ring.

Compounds of the invention that may be mentioned include those in which:

$X^1$ represents:

(a) $C(O)OR^{9a}$, —$C(O)N(R^{10b})R^{9b}$, —$C(O)N(H)C(=NR^{9c})N(R^{10d})R^{9d}$; —$C(O)N(H)CN$, —$S(O)_3R^{9e}$, —$P(O)(OR^{9f})_2$, —$P(O)(OR^{9g})N(R^{10h})R^{9h}$, —$P(O)(N(R^{10i})R^{9i})_2$, —$B(OR^{9y})_2$ or —$C(O)N(H)(O)_2R^{11}$;

(b) an aryl group or a heteroaryl group, both of which are substituted by at least one substituent selected from $X^2$, and one or more farther optional substituents selected from A; or (c) a heterocycloalkyl group substituted by at least one substituent selected from $X^2$, and one or more further optional substituents selected from $G^1$ and/or $Z^1$; and/or $X^2$ represents $C(O)OR^{9a}$, —$C(O)N(R^{10b})R^{9b}$, —$C(O)N(H)C(=NR^{9c})N(R^{10d})R^{9d}$; —$C(O)N(H)CN$, —$S(O)_3R^{9e}$, —$P(O)(OR^{9f})_2$, —$P(O)(OR^{9g})N(R^{10h})R^{9h}$, —$P(O)(N(R^{10i})R^{9i})_2$, —$B(OR^{9y})_2$ or —$C(O)N(H)S(O)_2R^{11}$.

More compounds of the invention that may be mentioned include those in which:

Y represents —$C(O)OR^{9a}$, —$S(O)_3R^{9e}$, —$P(O)(OR^{9f})_2$, —$P(O)(OR^{9g})N(R^{10h})R^{9h}$, —$P(O)(N(R^{10i})R^{9i})_2$, —$B(OR^{9y})_2$, —$C(CF_3)_2OH$, —$S(O)_2N(R^{10z})R^{9z}$ or any one of the following groups:

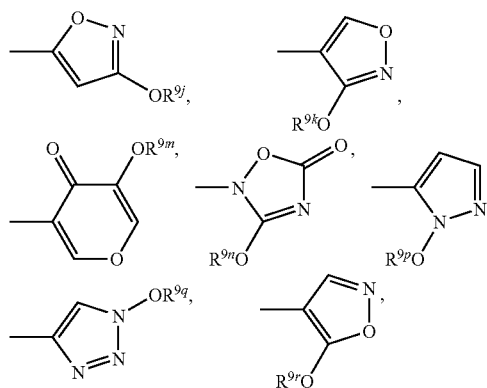

Further compounds of the invention that may be mentioned include those in which, when Y represents either:

and T represents $C_{1-8}$ alkylene or $C_{2-8}$ heteroalkylene, both of which are substituted at the carbon atom that is adjacent to Y by $Z^1$, then $Z^1$ represents =S, =$NOR^{12b}$, =$NS(O)_2N(R^{13f})R^{12c}$, =NCN or =$C(H)NO_2$.

Further compounds of the invention that may be mentioned include those in which, when Y represents —$C(O)OR^{9a}$, T represents:

(a) a $C_{1-8}$ alkylene or a $C_{2-8}$ heteroalkylene chain, both of which latter two groups:
  (i) optionally contain one or more unsaturations (for example double or triple bonds);
  (ii) are optionally substituted by one or more substituents selected from $G^1$ and/or $Z^1$; and/or
  (iii) may comprise an additional 3- to 8-membered ring formed between any one or more (e.g. one or two) members of the $C_{1-8}$ alkylene or $C_{2-8}$ heteroalkylene chain, which ring optionally contains 1 to 3 heteroatoms and/or 1 to 3 unsaturations (for example double or triple bonds) and which ring is itself optionally substituted by one or more substituents selected from $G^1$ and/or $Z^1$; or (b) an arylene group or a heteroarylene group, both of which groups are optionally substituted by one or more substituents selected from A.

More compounds of the invention that may be mentioned include those in which:

$R^1$ is preferably phenyl substituted, for example in the 4-position, by A;

A represents $G^1$;

$G^1$ represents -$A^1$-$R^{12a}$;

$A^1$ represents —$N(R^{13a})A^4$-;

$A^4$ represents a single bond;

$R^{12a}$ and $R^{13a}$ independently represent $C_{1-6}$ alkyl (such as $C_{1-3}$ alkyl (e.g. methyl)), which alkyl group is optionally substituted (by, for example, halo atoms) or, preferably, unsubstituted.

Preferred compounds of the invention include those in which:

T represents a single bond or linear or branched $C_{1-3}$ alkylene, which latter group is optionally substituted by one or more $Z^1$ substituent;

Y represents —C(O)OR$^{9a}$, —B(OR$^{9y}$)$_2$, —S(O)$_3$R$^{9e}$, —P(O)(OR$^{9f}$)$_2$ or a tetrazolyl group as hereinbefore defined;

Q represents a single bond, $C_{1-8}$ alkylene or nitrogen-containing $C_{2-6}$ heteroalkylene, which latter two groups are optionally substituted with one or more $G^1$ groups;

$X^1$ represents —C(O)OR$^{9a}$, —P(O)(OR$^{9f}$)$_2$, or an aryl group, a heteroaryl group or a heterocycloalkyl group, which latter three groups are substituted as hereinbefore defined;

$X^2$ represents —C(O)OR$^{9a}$ or —P(O)(OR$^{9f}$)$_2$;

A represents $G^1$ or $C_{1-7}$ alkyl optionally substituted by one or more $G^1$ groups;

$G^1$ represents cyano, —NO$_2$ or, more preferably, halo or -A$^1$-R$^{12a}$;

$A^1$ represents a single bond, —C(O)A$^2$-, —N(R$^{13a}$)A$^4$- or —OA$^5$-;

$A^4$ and $A^5$ independently represent —C(O)—, —C(O)N(R$^{13d}$)—, —C(O)O— or a single bond;

$R^{12a}$, $R^{12b}$ and $R^{12c}$ independently represent hydrogen, an aryl group, a heteroaryl group (such as tetrazolyl (e.g. 5-tetrazolyl), imidazolyl (e.g. 4-imidazolyl or 2-imidazolyl) or pyridyl (e.g. 3-pyridyl, 4-pyridyl or, especially, pyrid-2-yl), a heterocycloalkyl group (such as $C_{4-8}$ heterocycloalkyl, which group contains one oxygen or, preferably, nitrogen atom and, optionally, a further nitrogen or oxygen atom) or, more preferably, $C_{1-6}$ alkyl, which latter four groups are optionally substituted by one or more $G^3$ groups and/or (in the case of allyl and heterocycloalkyl) $Z^3$ groups;

$Z^1$ represents =NOR$^{12b}$, =NCN or, preferably, =O;

$G^2$ represents cyano, —N$_3$ or, more preferably, halo, —NO$_2$ or -A$^6$-R$^{14a}$;

$A^6$ represents —N(R$^{15a}$)A$^9$- or —OA$^{10}$-;

$A^9$ represents —C(O)N(R$^{15d}$)—, —C(O)O— or, more preferably, a single bond or —C(O)—;

$A^{10}$ represents a single bond;

$Z^2$ represents =NOR$^{14b}$ or =NCN or, more preferably, =O;

$G^3$ represents halo, —NO$_2$ or -A$^{11}$-R$^{16a}$;

$A^{11}$ represents —N(R$^{17a}$)— or —O—;

$Z^3$ represents =O;

when any one of R$^{16a}$, R$^{16b}$, R$^{16c}$, R$^{17a}$, R$^{17b}$, R$^{17c}$, R$^{17d}$, R$^{17e}$ and R$^{17f}$ represents optionally substituted $C_{1-6}$ allyl, the optional substituent is one or more halo groups;

when any one of R$^{18a}$, R$^{18b}$, R$^{18c}$, R$^{18d}$, R$^{18e}$, R$^{18f}$, R$^{19a}$, R$^{19b}$ and R$^{19c}$ represents optionally substituted $C_{1-4}$ allyl, the optional substituent is one or more fluoro groups.

Preferred aryl and heteroaryl groups that $R^1$, $X^1$ (when $X^1$ represents an aryl or heteroaryl group) and E may represent include optionally substituted carbazolyl or, preferably, phenyl, naphthyl, pyrrolyl, furanyl, thienyl, pyrazolyl, imidazolyl (e.g. 1-imidazolyl, 2-imidazolyl or 4-imidazolyl), oxazolyl, isoxazolyl, thiazolyl, pyridyl (e.g. 2-pyridyl, 3-pyridyl or 4-pyridyl), indazolyl, indolyl, indolinyl, isoindolinyl, quinolinyl, 1,2,3,4-tetrahydroquinolinyl, isoquinolinyl, 1,2,3,4-tetrahydroisoquinolinyl, quinolizinyl, benzofuranyl, isobenzofuranyl, chromanyl, benzothienyl, pyridazinyl, pyrimidinyl, pyrazinyl, indazolyl, benzimidazolyl, quinazolinyl, quinoxalinyl, 1,3-benzodioxolyl, tetrazolyl, benzothiazolyl, and/or benzodioxanyl, groups.

Preferred values of $R^1$ include optionally substituted carbazolyl (e.g. 3-carbazolyl), benzodioxolyl and, preferably, phenyl, pyridyl (e.g. pyrid-2-yl) or imidazolyl.

Preferred values of E include optionally substituted naphthyl (e.g. 2-naphtyl), quinolinyl (e.g. 4-quinolinyl) and, preferably, phenyl, pyridyl (e.g. pyrid-2-yl) or imidazolyl.

Optional substituents on $R^1$, $R^2$, $R^3$, $R^4$, $R^5$, $X^1$ and E groups are preferably selected from:

—C(O)OR$^{21}$;

—C(O)N(R$^{21}$)R$^{22}$;

—S(O)$_2$R$^{21}$; or, more preferably, halo (e.g. fluoro, chloro or bromo);

cyano;

—NO$_2$;

$C_{1-6}$ allyl, which alkyl group may be linear or branched (e.g. $C_{1-4}$ alkyl (including ethyl, n-propyl, isopropyl, n-butyl or, preferably, methyl or t-butyl), n-pentyl, isopentyl, n-hexyl or isohexyl), cyclic (e.g. cyclopropyl, cyclobutyl, cyclopentyl or cyclohexyl), part-cyclic (e.g. cyclopropylmethyl), unsaturated (e.g. 1-propenyl, 2-propenyl, 1-butenyl, 2-butenyl, 3-butenyl, 1-pentenyl, 2-pentenyl, 4-pentenyl or 5-hexenyl) and/or optionally substituted with one or more —C(O)OR$^{21}$ group or, preferably, halo (e.g. chloro or, preferably, fluoro) group (so forming, for example, chloromethyl or, preferably, fluoromethyl, difluoromethyl or, preferably, trifluoromethyl);

heterocycloalkyl, such as a $C_{4-5}$ heterocycloalkyl group, preferably containing a nitrogen atom and, optionally, a further nitrogen or oxygen atom, so forming for example morpholinyl (e.g. 4-morpholinyl), piperazinyl (e.g. 4-piperazinyl) or piperidinyl (e.g. 1-piperidinyl and 4-piperidinyl) or pyrrolidinyl (e.g. 1-pyrrolidinyl), which heterocycloalkyl group is optionally substituted by one or more (e.g. one or two) substituents selected from $C_{1-3}$ alkyl (e.g. methyl) and =O; —OR$^{21}$; and

—N(R$^{21}$)R$^{22}$;

wherein $R^{21}$ and $R^{22}$ independently represent, on each occasion when mentioned above, H or $C_{1-6}$ alkyl, such as methyl, ethyl, n-propyl, n-butyl, t-butyl, cyclopropyl, cyclobutyl, cyclohexyl or, preferably, isopropyl or cyclopentyl (which allyl groups are optionally substituted by one or more halo (e.g. fluoro) groups (to form e.g. a trifluoromethyl group)).

Preferred values of R$^{9a}$ to R$^{9z}$ include $C_{1-4}$ alkyl (e.g. ethyl) and, particularly, H. Preferred values of R$^{10b}$, R$^{10d}$, R$^{10h}$, R$^{10i}$, R$^{10j}$ and R$^{10z}$ include $C_{1-6}$ (e.g. $C_{1-3}$) allyl and H.

More preferred compounds include those in which:

one or $R^4$ and, more preferably. $R^3$ represents -D-E and the other (more preferably) represents H;

D represents a single bond or —O—;

$R^2$ and/or $R^5$ represent H;

T represents a single bond, $C_{1-3}$ alkylene (e.g. cyclopropylene (e.g. 1-cyclopropylene), isopropylene (e.g. 1-isopropylene), ethylene (e.g. 1-ethylene) or, preferably, methylene) or phenylene (e.g. 4-phenylene);

Y represents —C(O)OR$^{9a}$;

Q represents a single bond, linear $C_{1-4}$ alkylene (e.g. methylene, ethylene or propylene), branched $C_{2-4}$ alkylene (e.g. 1,1-dimethylmethylene) or cyclic $C_{3-7}$ alkylene (e.g. cyclopropylene or cyclohexylene), all of which alkylene groups are optionally substituted with one or more $G^1$ groups, or $C_{2-3}$ (e.g. $C_2$) heterocycloalkylene, wherein the heteroatom group that interrupts the $C_{2-3}$ alkylene chain is —N(R$^{20}$)—, in which R$^{20}$ represents $C_{1-3}$ alkyl (e.g. methyl);

$X^1$ represents unsubstituted tetrazolyl (e.g. tetrazol-5-yl) or preferably, —C(O)OR$^{9a}$, —P(O)(OR$^{9f}$)$_2$ or a tetrazolyl group (e.g. a 1H-tetrazol-5-yl group), a phenyl or a pyridyl group substituted by $X^2$;

$X^2$ represents —C(O)OR$^{9a}$;

A represents a $C_{4-5}$ heterocycloalkyl group as hereinbefore defined or, preferably, G$^1$ or $C_{1-6}$ alkyl (e.g. ethyl, isopropyl or, preferably, methyl or t-butyl) optionally substituted by one or more G$^1$ groups;

G$^1$ represents cyano or, preferably, fluoro, chloro or -A$^1$-R$^{12a}$;

A$^1$ represents —S(O)$_2$A$^3$ or, preferably, —C(O)A$^2$-, —N(R$^{13a}$)A$^4$- or —OA$^5$-;

A$^2$ represents —N(R$^{13b}$)— or, preferably, —O—;

A$^3$ represents a single bond;

A$^4$ represents a single bond or, preferably, —C(O)—

A$^5$ represents a single bond;

R$^{12a}$, R$^{12b}$ and R$^{12c}$ independently represent H or $C_{1-5}$ alkyl (e.g. ethyl or, preferably, methyl, isopropyl or cyclopentyl);

R$^{13a}$, R$^{13b}$, R$^{13c}$, R$^{13d}$, R$^{13e}$ and R$^{13f}$ independently represent H or $C_{1-2}$ allyl (e.g. methyl or ethyl);

any pair of R$^{12a}$ to R$^{12c}$ and R$^{13a}$ to R$^{13f}$ are linked to form a 5- or 6-membered ring, optionally containing a further heteroatom (e.g. oxygen) so forming, for example, a piperidinyl or morpholinyl group, G$^3$ represents halo (e.g. fluoro).

Preferred values of -Q-X$^1$ include —C(O)OH, —C(O)OC$_2$H$_5$, tetrazol-5-yl, —C(O)OCH$_3$, —CH$_2$CH(N(H)C(O)CH$_3$)C(O)OH, —CH$_2$N(CH$_3$)CH$_2$C(O)OH, —CH$_2$((2-C(O)OH)piperidin-1-yl) and —C$_2$H$_4$C(O)OH.

Preferred values of T-Y include —C(O)OC$_2$H$_5$, —CH$_2$C(O)OC$_2$H$_5$, (4-C(O)OH)phenyl, —C(O)OH, —CH$_2$C(O)OH, -cyclopropyl-C(O)OH (e.g. —C(CH$_2$—CH$_2$)C(O)OH, i.e. a cyclopropyl group substituted by —C(O)OH α to the point of attachment of the T group to the essential indole ring), —C(CH$_3$)$_2$C(O)OH, —CH(CH$_3$)C(O)OH.

R$^1$ preferably represents unsubstituted phenyl, 4-cyclopropoxyphenyl, 4-trifluoromethoxyphenyl, 4-tert-butylphenyl, 4-diethylaminophenyl, chlorophenyl (e.g. 3- or 4-chlorophenyl), methoxyphenyl (e.g. 2-, 3- or 4-methoxyphenyl), benzodioxolyl (e.g. unsubstituted 1,3-benzodioxol-5-yl), 4-carboxymethylphenyl, 4-isopropylphenyl, (9-ethyl)carbazol-3-yl, 4-dimethylaminophenyl, 4-(piperidin-1-yl)phenyl, 4-(morpholin-4-yl)phenyl, 5-methoxypyrid-2-yl and, preferably, 4-cyclopentoxyphenyl and 4-isopropoxyphenyl.

Preferred values of E include trifluoromethylphenyl (e.g. 3- or 4-trifluoromethylphenyl), 4-isopropoxyphenyl, trifluoromethoxyphenyl (e.g. 3- or 4-trifluoromethoxyphenyl), 3-cyano-6-methylpyrid-2-yl, 3-carboxy-6-methylpyrid-2-yl, 3-amido-6-methylpyrid-2-yl, 3-amidopyrid-2-yl, 5-carboxypyrid-2-yl, 5-chloromethylpyrid-2-yl, 5-aminopyrid-2-yl, 3-carboxypyrid-2-yl, 3-carboxyphenyl, 3-methylsulfonylphenyl, 3,5-ditrifluoromethylphenyl, dichlorophenyl (e.g. 3,4-dichlorophenyl), 3-chloro-5-methylphenyl, 3-chloro-4-fluorophenyl, 2-naphthyl, 7-chloroquinolin-4-yl, and, preferably, 4-tert-butylphenyl, chlorophenyl (e.g. 3- or 4-chlorophenyl), 5-trifluoromethylpyrid-2-yl.

Particularly preferred compounds of the invention include those of the examples described hereinafter.

Compounds of the invention may be made in accordance with techniques that are well known to those skilled in the art, for example as described hereinafter.

According to a further aspect of the invention there is provided a process for the preparation of a compound of formula I, which process comprises:

(i) reaction of a compound of formula II,

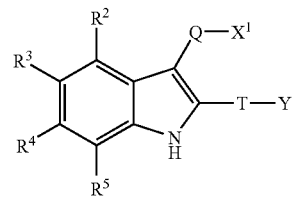

wherein Q, X$^1$, R$^2$, R$^3$, R$^4$, R$^5$, T and Y are as hereinbefore defined, with a compound of formula III,

R$^1$L$^1$  III wherein L$^1$ represents a suitable leaving group such as chloro, bromo, iodo, a sulfonate group (e.g. —OS(O)$_2$CF$_3$, —OS(O)$_2$CH$_3$, —OS(O)$_2$PhMe or a nonaflate) or —B(OH)$_2$ and R$^1$ is as hereinbefore defined, for example optionally in the presence of an appropriate metal catalyst (or a salt or complex thereof) such as Cu, Cu(OAc)$_2$, CuI (or CuI/diamine complex), Pd(OAc)$_2$, Pd$_2$(dba)$_3$ or NiCl$_2$ and an optional additive such as Ph$_3$P, 2,2'-bis(diphenylphosphino)-1,1'-binaphthyl, xantphos, NaI or an appropriate crown ether, such as 18-crown-6-benzene, in the presence of an appropriate base such as NaH, Et$_3$N, pyridine, N,N'dimethylethylenediamine, Na$_2$CO$_3$, K$_2$CO$_3$, K$_3$PO$_4$, Cs$_2$CO$_3$, t-BuONa or t-BuOK (or a mixture thereof), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof) or in the absence of an additional solvent when the reagent may itself act as a solvent (e.g. when R$^1$ represents phenyl and L$^1$ represents bromo, i.e. bromobenzene). This reaction may be carried out at room temperature or above (e.g. at a high temperature, such as the reflux temperature of the solvent system that is employed) or using microwave irradiation;

(ii) for compounds of formula I in which X$^1$ is as hereinbefore defined, and is preferably other than —C(O)N(H)C(=NR$^{9c}$)N(R$^{10d}$)R$^{9d}$; —C(O)N(H)CN or —C(O)N(H)S(O)$_2$R$^{11}$, reaction of a compound of formula IV,

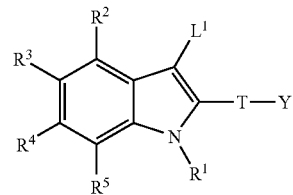

wherein L$^1$, R$^1$, R$^2$, R$^3$, R$^4$, R$^5$, T and Y are as hereinbefore defined, with a compound of formula V,

X$^1$-Q-L$^2$  V wherein L$^2$ represents a suitable leaving group such as chloro, bromo, iodo, —B(OH)$_2$ or a protected derivative thereof, for example a 4,4,5,5-tetramethyl-1,3,2-dioxaborolan-2-yl group, 9-borabicyclo[3.3.1]nonane (9-BBN), —Sn(allyl)$_3$ (e.g. —SnMe$_3$ or —SnBu$_3$), or a similar group known to the skilled person, and Q and $X^1$ are as hereinbefore defined (e.g. $X^1$ is preferably other than —C(O)N(H)C(=NR$^{9c}$)N(R$^{10d}$)R$^{9d}$; —C(O)N(H)CN or —C(O)N(H)S(O)$_2$R$^{11}$). The skilled person will appreciate that $L^1$ and $L^2$ will be mutually compatible. In this respect, preferred leaving groups for compounds of formula V in which Q is $C_{1-8}$ alkylene or $C_{2-8}$ heterocycloalkylene include chloro or bromo groups, and preferred leaving groups for compounds of formula V in which Q is a single bond include halo (e.g. chloro or bromo) groups, —B(OH)$_2$, -4,4,5,5-tetramethyl-1,3,2-dioxaborolan-2-yl, 9-borabicyclo[3.3.1]-nonane (9-BBN), or —Sn(alkyl)$_3$. This reaction may be performed, for example in the presence of a suitable catalyst system, e.g. a metal (or a salt or complex thereof) such as CuI, Pd/C, PdCl$_2$, Pd(OAc)$_2$, Pd(Ph$_3$P)$_2$Cl$_2$, Pd(Ph$_3$P)$_4$, Pd$_2$(dba)$_3$ or NiCl$_2$ and a ligand such as t-Bu$_3$P, (C$_6$H$_{11}$)$_3$P, Ph$_3$P, AsPh$_3$, P(o-Tol)$_3$, 1,2-bis(diphenylphosphino)ethane, 2,2'-bis(di-tert-butylphosphino)-1,1'-biphenyl, 2,2'-bis(diphenylphosphino)-1,1'-bi-naphthyl, 1,1'-bis(diphenylphosphinoferrocene), 1,3-bis(diphenylphosphino)propane, xantphos, or a mixture thereof, together with a suitable base such as, Na$_2$CO$_3$, K$_3$PO$_4$, Cs$_2$CO$_3$, NaOH, KOH, K$_2$CO$_3$, CsF, Et$_3$N, (i-Pr)$_2$NEt, t-BuONa or t-BuOK (or mixtures thereof) in a suitable solvent such as dioxane, toluene, ethanol, dimethylformamide, ethylene glycol dimethyl ether, water, dimethylsulfoxide, acetonitrile, dimethylacetamide, N-methylpyrrolidinone, tetrahydrofuran or mixtures thereof. The reaction may also be carried out for example at room temperature or above (e.g. at a high temperature such as the reflux temperature of the solvent system) or using microwave irradiation. The skilled person will appreciate that certain compounds of formula IV (in particular those in which $L^1$ represents —B(OH)$_2$) are also compounds of formula I and therefore compounds of the invention. In the case where:

(I) Q represents $C_{2-8}$ alkenylene or $C_{2-8}$ heterocycloalkenylene and $X^1$ is as hereinbefore defined; or (II) Q represents a single bond and $X^1$ represents heterocycloalkenyl, and, in each case, the double bond is between the atoms that are α and β to $L^2$, the skilled person will appreciate that the double bond may migrate on formation of the compound of formula I to form a double bond that is between the atoms that are β and γ to the indole ring;

(iia) for compounds of formula I in which $X^1$ represents —C(O)N(H)C(=NR$^{9c}$)N(R$^{10d}$)R$^{9d}$, —C(O)N(H)CN or —C(O)N(H)S(O)$_2$R$^{11}$, reaction of either a compound corresponding to a compound of formula I but in which $X^1$ represents H, or a compound of formula IV in which the $L^1$ group is activated (for example as described hereinafter in respect of process (vi) and so forming, for example, an —Mg-halide or a -$L^1$ group), with a compound of formula VA,

   VA wherein R$^{za}$ represents —C(=NR$^{9c}$)N(R$^{10d}$)R$^{9d}$, —CN or —S(O)$_2$R$^{11}$, followed by quenching with a suitable proton source (e.g. water or aqueous, saturated NH$_4$Cl solution). This reaction may be performed in the presence of a suitable solvent, such as a polar aprotic solvent (e.g. tetrahydrofuran or diethyl ether), at sub-ambient temperatures (e.g. 0° C. to −78° C.) under an inert atmosphere;

(iii) for compounds of formula I in which Q represents $C_{2-8}$ heteroalkylene (optionally substituted by one or more substituents selected from G$^1$), in which the heteroatom-containing group interrupting the alkylene chain is —N(R$^{20}$)— and $X^1$ is as hereinbefore defined, or Q represents $C_{1-8}$ allylene (optionally substituted by one or more substituents selected from G$^1$) and $X^1$ is a nitrogen-containing heterocycloalkyl group substituted by $X^2$, which group is attached to Q through a nitrogen atom in that group, reaction of a compound of formula VI,

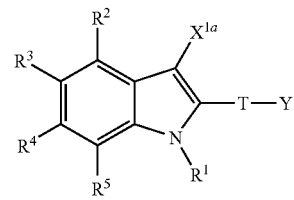   VI wherein $X^{1a}$ represents either (a) in the case of formation of a compound of formula I in which Q represents $C_{2-8}$ heteroalkylene, in which the heteroatom-containing group interrupting the alkylene chain is —N(R$^{20}$)—, a $C_{1-7}$ alkyl, group substituted by a —CHO group and optionally substituted with one or more substituents selected from G$^1$; or (b) in the case of formation of a compound of formula I in which Q represents $C_{1-8}$ allylene and $X^1$ is a nitrogen-containing heterocycloalkyl group as defined above, a $C_{1-8}$ alkyl group substituted by a $Z^1$ group in which $Z^1$ is =O and optionally substituted with one or more substituents selected from G$^1$, and R$^1$, R$^2$, R$^3$, R$^4$, R$^5$, T and Y are as hereinbefore defined under reductive amination conditions in the presence of a compound of formula VII,

R$^{23}$(R$^{24}$)NH   VII wherein either (a) R$^{24}$ represents $C_{1-7}$ alkyl, optionally substituted with one or more substituents selected from G$^1$, provided that the total number of carbon atoms in $X^{1a}$ and R$^{24}$ in combination is between 2 and 8, and R$^{23}$ represents R$^{20}$ as hereinbefore defined; or (b) R$^{23}$ and R$^{24}$ and the nitrogen atom to which they are attached together represent a nitrogen-containing heterocycloalkyl group as hereinbefore defined substituted by at least one substituent selected from $X^2$ and one or more further optional substituents selected from G$^1$ as hereinbefore defined, under conditions well known to those skilled in the art;

(iv) for compounds of formula I in which Q represents optionally substituted $C_{2-8}$ alkenylene or $C_{2-8}$ heteroalkenylene (in which a point of unsaturation is between the carbon atoms that are α and β to the indole ring), reaction of a corresponding compound of formula IV in which $L^1$ represents halo (e.g. iodo) with a compound of formula VIIIA,

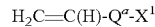   VIIIA or, depending upon the geometry of the double bond, reaction of a compound of formula VI in which $X^{1a}$ represents —CHO with either a compound of formula VIIIB,

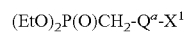   VIIIB or the like, or a compound of formula VIIIC,

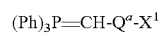   VIIIC or the like, wherein, in each case, $Q^a$ represents a single bond, $C_{1-6}$ all-ylene or $C_{1-6}$ heteroalkylene, which alkylene and heteroalkylene groups are optionally substituted with one of more substituents selected from G$^1$ and/or $Z^1$, and $X^1$, G$^1$ and $Z^1$ are as hereinbefore defined, for example, in the case of a reaction of a compound of formula IV with compound of formula VIIIA, in the presence of an appropriate catalyst (such as PdCl$_2$(PPh$_3$)$_2$), a suitable base (e.g. NaOAc and/or triethylamine) and an organic solvent (e.g. DMF) and, in the case of reaction of a compound of formula VI with either a compound of formula VIIIB, or VIIIC, under standard Horner-Wadsworth-Emmons, or Wittig, reaction conditions, respectively;

(v) for compounds of formula I in which Q represents optionally substituted, saturated $C_{2-8}$ alkylene, saturated cycloalkylene, saturated $C_{2-8}$ heteroalkylene, saturated heterocycloalkylene, $C_{2-8}$ alkenylene, cycloalkenylene, $C_{2-8}$ heteroalkenylene or heterocycloalkenylene, reduction (e.g. hydrogenation) of a corresponding compound of formula I in which Q represents optionally substituted $C_{2-8}$ alkenylene, cycloalkenylene, $C_{2-8}$ heteroalkenylene, heterocycloalkenylene, $C_{2-8}$ alkenylene, cycloalkenylene, $C_{2-8}$ heteroalkynylene or heterocycloalkynylene (as appropriate) under conditions that are known to those skilled in the art. For example, in the case where an alkynyl group is converted to a alkenyl group, in the presence of an appropriate poisoned catalyst (e.g. Lindlar's catalyst);

(vi) for compounds of formula I in which D represents a single bond, —C(O)—, —C($R^7$)($R^8$)—, $C_{2-4}$ allylene or —S(O)$_2$—, reaction of a compound of formula IX,

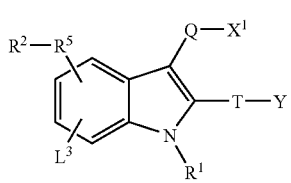

IX wherein $L^3$ represents $L^1$ or $L^2$ as hereinbefore defined, which group is attached to one or more of the carbon atoms of the benzenoid ring of the indole, $R^2$-$R^5$ represents whichever of the three other substituents on the benzenoid ring, i.e. $R^2$, $R^3$, $R^4$ and $R^5$, are already present in that ring, and Q, $X^1$, $R^1$, $R^2$, $R^3$, $R^4$, $R^5$, T and Y are as hereinbefore defined, with a compound of formula X, E-$D^a$-$L^4$    X wherein $D^a$ represents a single bond, —C(O)—, —C($R^7$)($R^8$)—, $C_{2-4}$ alkylene or —S(O)$_2$—, $L^4$ represents $L^1$ (when $L^3$ is $L^2$) or $L^2$ (when $L^3$ is $L^1$), and $L^1$, $L^2$, E, $R^7$ and $R^8$ are as hereinbefore defined. For example, when $D^a$ represents a single bond, —C(O)— or $C_{2-4}$ alkylene, the reaction may be performed for example under similar conditions to those described hereinbefore in respect of process step (ii) above. Further, when $D^a$ represents —C(O)—, —C($R^7$)($R^8$)—, $C_{2-4}$ alkylene or —S(O)$_2$—, the reaction may be performed by first activating the compound of formula IX. The skilled person will appreciate that compounds of formula IX may be activated when $L^3$ represents halo, by:

(I) forming the corresponding Grignard reagent under standard conditions known to those skilled in the art (e.g. employing magnesium or a suitable reagent such as a mixture of $C_{1-6}$ alkyl-Mg-halide and $ZnCl_2$ or LiCl), followed by reaction with a compound of formula X, optionally in the presence of a catalyst (e.g. $FeCl_3$) under conditions known to those skilled in the art; or (II) forming the corresponding lithiated compound under halogen-lithium exchange reaction conditions known to those skilled in the art (e.g. employing n-BuLi or t-BuLi in the presence of a suitable solvent (e.g. a polar aprotic solvent such as THF)), followed by reaction with a compound of formula X.

The skilled person will also appreciate that the magnesium of the Grignard reagent or the lithium of the lithiated species may be exchanged to a different metal (i.e. a transmetallation reaction may be performed), for example to zinc (e.g. using $ZnCl_2$) and the intermediate so formed may then be subjected to reaction with a compound of formula X under conditions known to those skilled in the art, for example such as those described hereinbefore in respect of process (ii) above;

(vii) for compounds of formula I in which D represents —S—, —O— or $C_{2-4}$ alkynylene in which the triple bond is adjacent to E, reaction of a compound of formula IX as hereinbefore defined in which $L^3$ represents $L^2$ as hereinbefore defined (for example —B(OH)$_2$) with a compound of formula XI, E-$D^b$-H    XI wherein $D^b$ represents —S—, —O— or $C_{2-4}$ alkynylene in which the triple bond is adjacent to E and E is as hereinbefore defined. Such reactions may be performed under similar conditions to those described hereinbefore in respect of process step (ii) above, for example in the presence of a suitable catalyst system, such as Cu(OAc)$_2$, a suitable base, such as triethylamine or pyridine, and an appropriate organic solvent, such as DMF or dichloromethane;

(viii) for compounds of formula I in which D represents —S(O)— or —S(O)$_2$—, oxidation of a corresponding compound of formula I in which D represents —S— under appropriate oxidation conditions, which will be known to those skilled in the art;

(ix) for compounds of formula I in which D represents —O— or —S—, reaction of a compound of formula XII,

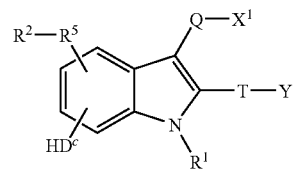

XII wherein the -$D^c$-H group is attached to one or more of the carbon atoms of the benzenoid ring of the indole, $D^c$ represents —O— or —S—, and Q, $X^1$, $R^1$, $R^2$-$R^5$, T and Y are as hereinbefore defined, with a compound of formula XIII,

E-$L^2$    XIII wherein $L^2$ is as hereinbefore defined (for example —B(OH)$_2$, chloro, bromo or iodo) and E is as hereinbefore defined, under conditions such as those described hereinbefore in respect of process step (ii) above;

(x) for compounds of formula I in which T and Y are as hereinbefore defined, provided that when Y represents —C(O)O$R^{9a}$, S(O)$_3R^{9e}$, —P(O)(O$R^{9f}$)$_2$, —P(O)(O$R^{9g}$)N($R^{10h}$)$R^{9h}$, —P(O)(N($R^{10i}$)$R^{9i}$)$_2$, —B(O$R^{9y}$)$_2$ or —S(O)$_2$N($R^{10z}$)$R^{9z}$, $R^{9a}$, $R^{9e}$ to $R^{9i}$, $R^{9y}$, $R^{9z}$, $R^{10h}$, $R^{10i}$ and $R^{10z}$ are other than H, reaction of a compound of formula XIV,

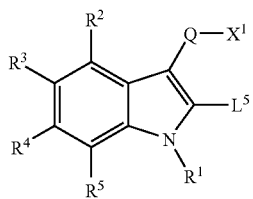

wherein L$^5$ represents an appropriate alkali metal group (e.g. sodium, potassium or, especially, lithium), a —Mg-halide, a zinc-based group or a suitable leaving group such as halo or —B(OH)$_2$, or a protected derivative thereof, and Q, X$^1$, R$^1$, R$^2$, R$^3$, R$^4$ and R$^5$ are as hereinbefore defined, with a compound of formula XV, $$L^6\text{-}T\text{-}Y^a \qquad XV$$

wherein Y$^a$ represents Y, provided that when Y represents —C(O)OR$^{9a}$, —S(O)$_3$R$^{9e}$, —P(O)(OR$^{9f}$)$_2$, —P(O)(OR$^{9g}$)N(R$^{10h}$)R$^{9h}$, —P(O)(N(R$^{10i}$)R$^{9i}$)$_2$, —B(OR$^{9y}$)$_2$ or —S(O)$_2$N(R$^{10z}$)R$^{9z}$, R$^{9a}$, R$^{9e}$ to R$^{9i}$, R$^{9y}$, R$^{9z}$, R$^{10h}$, R$^{10i}$ and R$^{10z}$ are other than H, L$^6$ represents a suitable leaving group known to those skilled in the art, such as halo (especially chloro or bromo), for example when Y$^a$ represents —C(O)OR$^{9a}$ or —S(O)$_3$R$^{9e}$, or C$_{1-3}$ alkoxy, for example when Y$^a$ represents —B(OR$^{9y}$)$_2$, and T is as hereinbefore defined. The reaction may be performed under similar reaction conditions to those described hereinbefore in respect of process (vi) above, followed by (if necessary) deprotection under standard conditions. The skilled person will appreciate that compounds of formula XIV in which L$^5$ represents —B(OH)$_2$ are also compounds of formula I. The skilled person will also appreciate that L$^5$ and L$^6$ (when they both represent leaving groups) will be mutually compatible in a similar manner to the L$^1$ and L$^2$ groups described hereinbefore in process step (ii) above;

(xi) for compounds of formula I in which T represents a single bond, Y represents —C(O)OR$^{9a}$ and R$^{9a}$ represents H, reaction of a compound of formula XIV as hereinbefore defined in which L$^5$ represents either:
(I) an alkali metal (for example, such as one defined in respect of process step (x) above); or
(II) —Mg-halide,
with carbon dioxide, followed by acidification under standard conditions known to those skilled in the art, for example, in the presence of aqueous hydrochloric acid;

(xii) for compounds of formula I in which T represents a single bond and Y represents —C(O)OR$^{9a}$, reaction of a corresponding compound of formula XIV in which L$^5$ is a suitable leaving group known to those skilled in the art (such as a sulfonate group (e.g. a triflate) or, preferably, a halo (e.g. bromo or iodo) group) with CO (or a reagent that is a suitable source of CO (e.g. Mo(CO)$_6$ or Co$_2$(CO)$_8$)), in the presence of a compound of formula XVA, $$R^{9a}OH \qquad XVA$$

wherein R$^{9a}$ is as hereinbefore defined, and an appropriate catalyst system (e.g. a palladium catalyst such as one described hereinbefore in respect of process step (ii)) under conditions known to those skilled in the art;

(xiii) for compounds of formula I in which T represents a single bond, Y represents —B(OR$^{9y}$)$_2$ and R$^{9y}$ represents H, reaction of a compound of formula XIV as hereinbefore defined with boronic acid or a protected derivative thereof (e.g. bis(pinacolato)diboron or triethyl borate), followed by (if necessary) deprotection under standard conditions;

(xiv) for compounds of formula I in which T represents a single bond and Y represents —S(O)$_3$R$^{9e}$, reaction of a compound of formula XIV as hereinbefore defined with:
(A) for such compounds in which R$^{9e}$ represents H, either SO$_3$ (or a suitable source of SO$_3$ such as a SO$_3$*pyridine or SO$_3$*Et$_3$N complex) or with SO$_2$ followed by treatment with N-chlorosuccinimide and then hydrolysis. Alternatively, a compound of formula XIV may be reacted with a protected sulfide, followed by deprotection and oxidation, or a compound of formula XIV may be reacted with chlorosulfonic acid (ClS(O)$_2$OH) followed by hydrolysis;
(B) for such compounds in which R$^{9e}$ is other than H, chlorosulfonic acid followed by reaction with a compound of formula XX as defined hereinafter in which R$^{9za}$ represents R$^{9e}$,
all under standard conditions;

(xv) for compounds of formula I in which T represents a single bond and Y represents

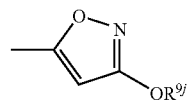

in which R$^{9j}$ represents hydrogen, reaction of a corresponding compound of formula I in which T represents a C$_2$ alkylene group substituted at the carbon atom that is attached to the indole ring system by Z$^1$, in which Z$^1$ represents =O and Y represents —C(O)OR$^{9a}$, in which R$^{9a}$ represents C$_{1-6}$ allyl with hydroxylamine or an acid addition salt thereof, for example in the presence of base (e.g. NaOH), e.g. under similar reaction conditions to those described in inter alia *J. Med. Chem.*, 43, 4930 (2000);

(xvi) for compounds of formula I in which T represents a single bond and Y represents

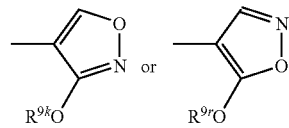

in which R$^{9k}$ and R$^{9r}$ represents hydrogen, reaction of a corresponding compound of formula I in which T represents a C$_1$ alkylene group substituted with G$^1$, in which G$^1$ represents -A$^1$-R$^{12a}$, A$^1$ represents —C(O)A$^2$, A$^2$ represents a single bond and R$^{12a}$ represents H, and Y represents —C(O)OR$^{9a}$, in which R$^{9a}$ represents methyl, or ethyl, respectively, with hydroxylamine or an acid addition salt thereof, for example in the presence of base (e.g. NaOH, or aniline, respectively) and an appropriate solvent (e.g. methanol, or water, respectively), e.g. under similar reaction conditions to those described in *J. Med. Chem.*, 44, 1051 (2001), or inter alia *J Am. Chem. Soc.*, 58, 1152 (1936), respectively;

(xvii) for compounds of formula I in which T represents a single bond and Y represents

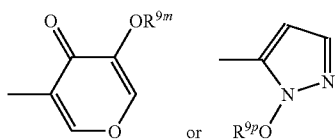

in which $R^{9m}$ and $R^{9p}$ represents hydrogen, reaction of a corresponding compound of formula I in which T represents a single bond, Y represents —B(OR$^{9y}$)$_2$ and R$^{9y}$ represents H with a compound of formula XV in which T represents a single bond, Y$^a$ represents

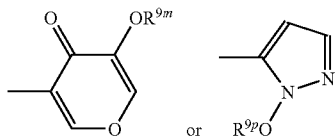

respectively, in which $R^{9m}$ and $R^{9p}$ represent hydrogen, and $L^6$ preferably represents e.g. a halo group, such as Br, or I, respectively, or a protected derivative (e.g. at the OH group with, for example, a benzyl group) of either compound, for example under reaction conditions similar to those described hereinbefore in process (ii) above and/or in *Heterocycles*, 36, 1803 (1993), or in *Bioorg. Med. Chem.*, 11, 1883 (2003), respectively, followed by (if necessary) deprotection under standard conditions;

(xviii) for compounds of formula I in which T represents a single bond and Y represents

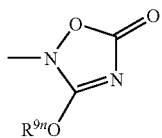

in which $R^{9n}$ represents hydrogen, reaction of a compound of formula XVI,

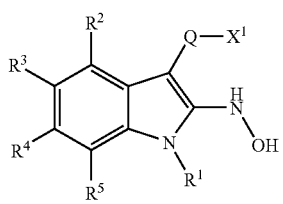

wherein Q, $X^1$, $R^1$, $R^2$, $R^3$, $R^4$ and $R^5$ are as hereinbefore defined with ethoxycarbonyl isocyanate in the presence of a suitable solvent (e.g. dichloromethane), followed by refluxing in the presence of Triton B and an alcoholic solvent (e.g. methanol), for example under similar reaction conditions to those described in *J. Het. Chets.*, 19, 971 (1982);

(xix) for compounds of formula I in which T represents a single-bond and Y represents

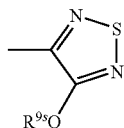

in which $R^{9s}$ represents hydrogen, reaction of a corresponding compound of formula I in which T represents a single bond and Y represents —C(O)OR$^{9a}$, in which R$^{9a}$ represents H with e.g. trimethylsilyl chloride (or the like), followed by reaction of the resultant intermediate with N$_4$S$_4$, for example under similar reaction conditions to those described in *Heterocycles*, 20, 2047 (1983);

(xx) for compounds of formula I in which T represents a single bond and Y represents

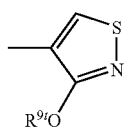

in which $R^{9t}$ represents hydrogen, reaction of a compound of formula XVII,

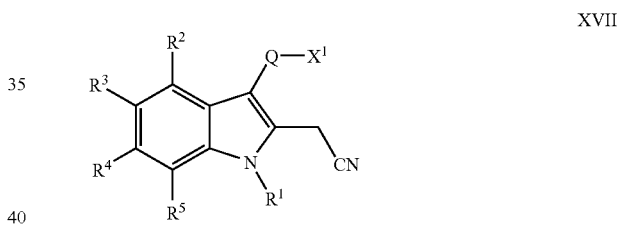

XVII wherein Q, $X^1$, $R^1$, $R^2$, $R^3$, $R^4$ and $R^5$ are as hereinbefore defined with a base (e.g. NaH) and CS$_2$ in the presence of a suitable solvent (e.g. tetrahydrofuran), oxidation of the resultant intermediate in the presence of, for example, hydrogen peroxide, and finally heating the resultant intermediate in the presence of a strong acid, such as HCl, for example under similar reaction conditions to those described in inter alia *Bioorg. Med. Chem. Lett.*, 2, 809 (1992);

(xxi) for compounds of formula I in which T represents a single bond and Y represents

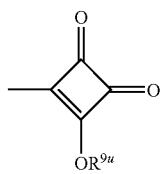

in which $R^{9u}$ represents hydrogen, reaction of a corresponding compound of formula I in which T represents C$_1$ alkylene, Y represents —C(O)OR$^{9a}$ and R$^{9a}$ represents H or, preferably, an activated (e.g. acid halide) derivative thereof with 1,1,2,2-tetraethoxyethene, for example in the presence of base (e.g. triethylamine), followed by acid (e.g. aqueous HCl), e.g. under similar reaction conditions to those described in *J. Am. Chem. Soc.*, 100, 8026 (1978);

(xxii) for compounds of formula I in which T represents a single bond and Y represents

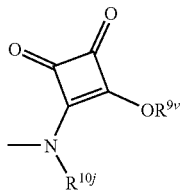

in which $R^{9v}$ and $R^{10j}$ independently represent hydrogen, reaction of a compound of formula XVI as hereinbefore defined with 3,4-dimethoxycyclobutene-1,2-dione, for example in the presence of base (e.g. KOH) and an appropriate solvent (e.g. methanol), followed by acid (e.g. aqueous HCl), e.g. under similar reaction conditions to those described in *J. Org. Chem.*, 68, 9233 (2003);

(xxiii) for compounds of formula I in which T represents a single bond and Y represents

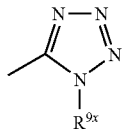

in which $R^{9x}$ represents hydrogen, reaction of a compound of formula XVIII,

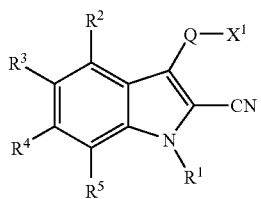

XVIII wherein Q, $X^1$, $R^1$, $R^2$, $R^3$, $R^4$ and $R^5$ are as hereinbefore defined with $NaN_3$ under standard conditions;

(xxiv) for compounds of formula I in which T represents optionally substituted $C_{2-8}$ alkenylene or $C_{2-8}$ heteroalkylene (in which a point of unsaturation is between the carbon atoms that are α and β to the indole ring), reaction of a compound of formula XIX,

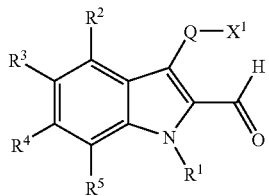

XIX wherein Q, $X^1$, $R^1$, $R^2$, $R^3$, $R^4$ and $R^5$ are as hereinbefore defined with a compound of formula XIXA,

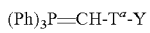

XIXA or the like (e.g. the corresponding Horner-Wadsworth-Emmons reagent), wherein $T^a$ represents a single bond or optionally substituted $C_{1-6}$ alkylene or $C_{2-6}$ heteoalkylene and Y is as hereinbefore defined, for example under standard Wittig reaction conditions, e.g. in the presence of a suitable organic solvent (e.g. DMF);

(xxv) for compounds of formula I in which T represents optionally substituted, saturated $C_{2-8}$ alkylene, saturated cycloalkylene, saturated $C_{2-8}$ heteroalkylene, saturated heterocycloalkylene, $C_{2-8}$ alkenylene, cycloalkenylene, $C_{2-8}$ heteroalkenylene or heterocycloalkenylene, reduction (e.g. hydrogenation) of a corresponding compound of formula I in which T represents optionally substituted $C_{2-8}$ alkenylene, cycloalkenylene, $C_{2-8}$ heteroalkenylene, heterocycloalkenylene, $C_{2-8}$ alkynylene, cycloalkynylene, $C_{2-8}$ heteroalkynylene or heterocycloalkynylene (as appropriate) under conditions that are known to those skilled in the art;

(xxvi) for compounds of formula I in which Y represents —C(O)OR$^{9a}$, —S(O)$_3$R$^{9e}$, —P(O)(OR$^{9f}$)$_2$, or —B(OR$^{9y}$)$_2$, in which R$^{9a}$, R$^{9e}$, R$^{9f}$ and R$^{9y}$ represent H, hydrolysis of a corresponding compound of formula I in which R$^{9a}$, R$^{9e}$, R$^{9f}$ or R$^{9y}$ (as appropriate) do not represent H, or, for compounds of formula I in which Y represents —P(O)(OR$^{9f}$)$_2$ or —S(O)$_3$R$^{9e}$, in which R$^{9f}$ and R$^{9e}$ represent H, a corresponding compound of formula I in which Y represents either —P(O)(OR$^{9g}$)N(R$^{10h}$)R$^{9h}$, —P(O)(N(R$^{10i}$)R$^{9i}$)$_2$ or —S(O)$_2$N(R$^{10z}$)R$^{9z}$ (as appropriate), all under standard conditions;

(xxvii) for compounds of formula I in which Y represents —C(O)OR$^{9a}$, —S(O)$_3$R$^{9e}$, —P(O)(OR$^{9f}$)$_2$, —P(O)(OR$^{9g}$)N(R$^{10h}$)R$^{9h}$ or —B(OR$^{9y}$)$_2$ and R$^{9a}$, R$^{9e}$, R$^{9f}$, R$^{9g}$ and R$^{9y}$ (i.e. those R$^9$ groups attached to an oxygen atom) do not represent H:

(A) esterification of a corresponding compound of formula I in which R$^{9a}$, R$^{9e}$, R$^{9f}$, R$^{9g}$ and R$^{9y}$ represent H; or (B) trans-esterification of a corresponding compound of formula I in which R$^{9a}$, R$^{9e}$, R$^{9f}$, R$^{9g}$ and R$^{9y}$ do not represent H (and do not represent the same value of the corresponding R$^{9a}$, R$^{9e}$, R$^{9f}$, R$^{9g}$ and R$^{9y}$ group in the compound of formula I to be prepared), under standard conditions in the presence of the appropriate alcohol of formula XX, R$^{9za}$OH  XX in which R$^{9za}$ represents R$^{9a}$, R$^{9e}$, R$^{9f}$, R$^{9g}$ or R$^{9y}$ provided that it does not represent H;

(xxviii) for compounds of formula I in which T represents a $C_1$ allylene group substituted with $G^1$, in which $G^1$ represents -A$^1$-R$^{12a}$, A$^1$ represents —C(O)A$^2$-, A$^2$ represents a single bond and R$^{12a}$ represents H, and Y represents —C(O)OR$^{9a}$, in which R$^{9a}$ is other than H, reaction of a corresponding compound of formula I in which the $C_1$ alkylene group that T represents is unsubstituted, with a $C_{1-6}$ allyl (e.g. ethyl) formate in the presence of a suitable base (e.g. sodium ethoxide), for example under similar conditions to those described in *Bioorg. Med. Chem. Lett.*, 13, 2709 (2003):

(xxix) for compounds of formula I in which Q and $X^1$ are as hereinbefore defined, provided that when $X^1$ or $X^2$ (as appropriate) represents —C(O)OR$^{9a}$, —C(O)N(R$^{10b}$)R$^{9b}$, —C(O)N(H)C(=NR$^{9c}$)N(R$^{10d}$)R$^{9d}$, —S(O)$_3$R$^{9e}$, —P(O)(OR$^{9f}$)$_2$, —P(O)(OR$^{9g}$)N(R$^{10h}$)R$^{9h}$, —P(O)(N(R$^{10i}$)R$^{9i}$)$_2$ or —B(OR$^{9y}$)$_2$, R$^{9a}$ to R$^{9i}$, R$^{9y}$, R$^{10b}$, R$^{10d}$, R$^{10h}$ and R$^{10i}$ are other than H, reaction of a compound of formula XXI,

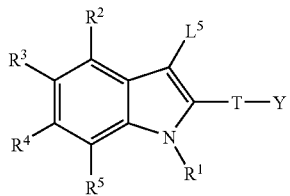

(XXI)

wherein $L^5$, T, Y, $R^1$, $R^2$, $R^3$, $R^4$ and $R^5$ are as hereinbefore defined, with a compound of formula XXII, $$L^6\text{-}Q\text{-}X^{1b} \qquad \text{XXII}$$

wherein $X^{1b}$ represents $X^1$, provided that when $X^1$ or $X^2$ (as appropriate) represents —C(O)OR$^{9a}$, —C(O)N(R$^{10b}$)R$^{9b}$, —C(O)N(H)C(=NR$^{9c}$)N(R$^{10d}$)R$^{9d}$, —S(O)$_3$R$^{9e}$, —P(O)(OR$^{9f}$)$_2$, —P(O)(OR$^{9g}$)N(R$^{10h}$)R$^{9h}$, —P(O)(N(R$^{10i}$)R$^{9i}$)$_2$ or —B(OR$^{9y}$)$_2$, $R^{9a}$ to $R^{9i}$, $R^{9y}$, $R^{10b}$, $R^{10d}$, $R^{10h}$ and $R^{10i}$ are other than H, or a protected derivative thereof, and Q and $L^6$ is as hereinbefore defined, for example under similar reaction conditions to those described hereinbefore in respect of process (ii) above, followed by (if necessary) deprotection under standard conditions;

(xxx) for compounds of formula I in which Q represents a single bond, $X^1$ represents —C(O)OR$^{9a}$ and $R^{9a}$ represents H, reaction of a compound of formula XXI in which $L^5$ represents either:
(I) an alkali metal (for example as defined in respect of process step (x) above); or
(II) —Mg-halide,
with carbon dioxide, followed by acidification under standard conditions known to those skilled in the art, for example, in the presence of aqueous hydrochloric acid;

(xxxi) for compounds of formula I in which Q represents a single bond and $X^1$ represents —C(O)OR$^{9a}$ or —C(O)N(R$^{10b}$)R$^{9b}$, reaction of a corresponding compound of formula XXI in which $L^1$ is a suitable leaving group known to those skilled in the art (such as a sulfonate group (e.g. a triflate) or, preferably, a halo (e.g. bromo or iodo) group) with CO (or a reagent that is a suitable source of CO (e.g. Mo(CO)$_6$ or Co$_2$(CO)$_8$), in the presence of a compound corresponding to a compound of formula XVA as hereinbefore defined or a compound of formula XXIII as defined hereinafter (as appropriate) and an appropriate catalyst system (e.g. a palladium catalyst such as one described hereinbefore in respect of process step (ii)) under conditions known to those skilled in the art;

(xxxii) for compounds of formula I in which Q represents a single bond, $X^1$ represents —B(OR$^{9y}$)$_2$ and $R^{9y}$ represents H, reaction of a compound of formula XXI as hereinbefore defined with boronic acid or a protected derivative thereof (e.g. bis(pinacolato)diboron or triethyl borate) and an appropriate catalyst system (e.g. a palladium catalyst such as one described hereinbefore in respect of process step (ii)) under conditions known to those skilled in the art, followed by (if necessary) deprotection under standard conditions;

(xxxiii) for compounds of formula I in which Q represents a single bond and $X^1$ represents —S(O)$_3$R$^{9e}$, reaction of a compound of formula XXI as hereinbefore defined with:
(A) for such compounds in which $R^{9e}$ represents H, either SO$_3$ (or a suitable source of SO$_3$ such as a SO$_3$*pyridine or SO$_3$*Et$_3$N complex) or with SO$_2$ followed by treatment with N-chlorosuccinimide and then hydrolysis, all under standard conditions. Alternatively, a compound of formula XXI may be reacted with a protected sulfide, followed by deprotection and oxidation, or a compound of formula XXI may be reacted with chlorosulfonic acid (ClS(O)$_2$OH) followed by hydrolysis;
(B) for such compounds in which $R^{9e}$ is other than H, chlorosulfonic acid followed by reaction with a compound of formula XX as defined hereinbefore in which $R^{9za}$ represents $R^{9e}$,
all under standard conditions;

(xxxiv) for compounds of formula I in which $X^1$ or $X^2$ (as appropriate) represents —C(O)OR$^{9a}$, —S(O)$_3$R$^{9e}$, —P(O)(OR$^{9f}$)$_2$ or —B(OR$^{9y}$)$_2$, in which $R^{9a}$, $R^{9e}$, $R^{9f}$ and $R^{9y}$ represent H, hydrolysis of a corresponding compound of formula I in which $R^{9a}$, $R^{9e}$, $R^{9f}$ or $R^{9y}$ (as appropriate) do not represent H, or, for compounds of formula I in which $X^1$ or $X^2$ (as appropriate) represents —C(O)OR$^{9a}$ a or —P(O)(OR$^{9f}$)$_2$, in which $R^{9a}$ and $R^{9f}$ represent H, a corresponding compound of formula I in which $X^1$ or $X^2$ (as appropriate) represents —C(O)N(H)S(O)$_2$R$^{11}$, —P(O)(OR$^{9g}$)N(R$^{10h}$)R$^{9h}$ or —P(O)(N(R$^{10i}$)R$^{9i}$)$_2$ (as appropriate), all under standard conditions;

(xxxv) for compounds of formula I in which $X^1$ or $X^2$ (as appropriate) represents —C(O)OR$^{9a}$, —S(O)$_3$R$^{9e}$, —P(O)(OR$^{9f}$)$_2$, —P(O)(OR$^{9g}$)N(R$^{10h}$)R$^{9h}$ or —B(OR$^{9y}$)$_2$ and $R^{9a}$, $R^{9e}$, $R^{9f}$, $R^{9g}$ and $R^{9y}$ (i.e. those $R^9$ groups attached to an oxygen atom) do not represent H:
(A) esterification of a corresponding compound of formula I in which $R^{9a}$, $R^{9e}$, $R^{9f}$, $R^{9g}$ and $R^{9y}$ represent H; or
(B) trans-esterification of a corresponding compound of formula I in which $R^{9a}$, $R^{9e}$, $R^{9f}$, $R^{9g}$ and $R^{9y}$ do not represent H (and do not represent the same value of the corresponding $R^{9a}$, $R^{9e}$, $R^{9f}$, $R^{9g}$ and $R^{9y}$ group in the compound of formula I to be prepared),
under standard conditions in the presence of the appropriate alcohol of formula XX as hereinbefore defined;

(xxxvi) for compounds of formula I in which Q represents a $C_1$ alkylene group substituted with $G^1$, in which $G^1$ represents -A$^1$-R$^{12a}$, $A^1$ represents —C(O)A$^2$-, $A^2$ represents a single bond and $R^{12a}$ represents H, and $X^1$ represents —C(O)OR$^{9a}$, in which $R^{9a}$ is other than H, reaction of a corresponding compound of formula I in which the C, allylene group that Q represents is unsubstituted, with a $C_{1-6}$ allyl (e.g. ethyl) formate in the presence of a suitable base (e.g. sodium ethoxide), for example under similar conditions to those described in *Bioorg. Med. Chem. Lett.*, 13, 2709 (2003);

(xxxvii) for compounds of formula I in which $X^1$ or $X^2$ (as appropriate) represents —C(O)N(R$^{10b}$)R$^{9b}$, —C(O)N(H)C(=NR$^{9c}$)N(R$^{10d}$)R$^{9d}$, —C(O)N(H)CN or —C(O)N(H)S(O)$_2$R$^{11}$ reaction of a corresponding compound of formula I in which $X^1$ or $X^2$ represents —C(O)OR$^{9a}$ with a compound of formula XXIII, $$R^{25}(R^{26})NH \qquad \text{XXIII}$$

wherein $R^{25}$ and $R^{26}$ represent, in the case of a compound of formula I in which $X^1$ or $X^2$ (as appropriate) represents:
(1) —C(O)N(R$^{10b}$)R$^{9b}$, $R^{9b}$ and $R^{10b}$;
(2) —C(O)N(H)C(=NR$^{9c}$)N(R$^{10d}$)R$^{9d}$, —C(=NR$^{9c}$)N(R$^{10d}$)R$^{9d}$ and H;
(3) —C(O)N(H)CN, —CN and H; or
(4) —C(O)N(H)S(O)$_2$R$^{11}$, —S(O)$_2$R$^{11}$ and H,
respectively, and $R^{9b}$ to $R^{9d}$, $R^{10b}$, $R^{10d}$ and $R^{11}$ are as hereinbefore defined under standard conditions. For example, the reaction may be performed in the presence of a suitable coupling reagent ((e.g. 1,1'-carbonyldiimidazole, N,N'-dicyclohexylcarbodiimide, 1-(3-dimethylaminopropyl)-3-ethylcarbodiimide (or hydrochloride thereof), N,N'-disuccinimidyl carbonate, benzotriazol-1-yloxytris(dimethylamino)phosphonium hexafluorophosphate, 2-(1H-benzotriazol-1-yl)-1,1,3,3-tetramethyluronium hexafluorophosphate, benzotriazol-1-yloxytrispyrrolidinophosphonium hexafluorophosphate, bromo-tris-pyrrolidinophosphonium hexafluorophosphate, 2-(1H-benzotriazol-1-yl)-1,1,3,3-tetramethyluronium tetrafluorocarbonate, 1-cyclohexylcarbodiimide-3-propyloxymethyl polystyrene, O-(7-azabenzotriazol-1-yl)-N,N,N',N'-tetramethyluronium hexafluorophosphate or O-benzotriazol-1-yl-N,N,N'N'-tetramethyluronium tetrafluoroborate), and/or a suitable base (e.g. sodium hydride, sodium bicarbonate, potassium carbonate, pyrrolidinopyridine, pyridine, triethylamine, tributylamine, trimethylamine, dimethylaminopyridine, diisopropylamine, diisopropylethylamine, 1,8-diazabicyclo[5.4.0]undec-7-ene, sodium hydroxide, N-ethyldiisopropylamine, N-(methylpolystyrene)-4-(methylamino)pyridine, potassium bis(trimethylsilyl)-amide, sodium bis(trimethylsilyl)amide, potassium tert-butoxide, lithium diisopropylamide, lithium 2,2,6,6-tetramethylpiperidine, butyllithium (e.g. n-, s- or t-butyllithium) or mixtures thereof) and an appropriate solvent (e.g. tetrahydrofuran, pyridine, toluene, dichloromethane, chloroform, acetonitrile, dimethylformamide, dimethylsulfoxide, water, triethylamine or mixtures thereof). Alternatively an azodicarboxylate may be employed under Mitsunobo conditions known to those skilled in the art. The skilled person will also appreciate that it may be convenient or necessary to first convert the acid or ester compound of formula I to a corresponding acid halide prior to reaction with the compound of formula XXIII. Such conversions may be performed in the presence of a suitable reagent (e.g. oxalyl chloride, thionyl chloride, etc) optionally in the presence of an appropriate solvent (e.g. dichloromethane, THF, toluene or benzene) and a suitable catalyst (e.g. DMF), resulting in the formation of the respective acyl chloride. The skilled person will appreciate that when compounds of formula XXIII are liquid in nature, they may serve as both solvent and reactant in this reaction. An alternative way of performing this step for compounds of formula I in which $X^1$ or $X^2$ represents —C(O)N($R^{10b}$)$R^{9b}$, includes the reaction of a compound of formula I in which $X^1$ or $X^2$ (as appropriate) represents —C(O)O$R^{9a}$ and $R^{9a}$ is other than H (e.g. ethyl) with a compound of formula XXIII, in the presence of, e.g. trimethylaluminium, for example in an inert atmosphere and in the presence of a suitable solvent (e.g. dichloromethane).

Compounds of formula II may be prepared by:
(a) reaction of a compound of formula XXIV,

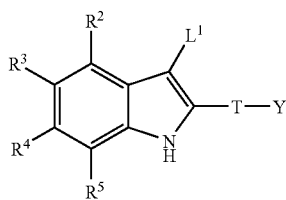

XXIV wherein $L^1$, $R^2$, $R^3$, $R^4$, $R^5$, T and Y are as hereinbefore defined, with, a compound of formula V as hereinbefore defined, for example under reaction conditions similar to those described hereinbefore in respect of preparation of compounds of formula I (process (ii)) above;

(bi) for compounds of formula II in which $X^1$ represents —C(O)N(H)C(=N$R^{9c}$)N($R^{10d}$)$R^{9d}$, —C(O)N(H)CN or —C(O)N(H)S(O)$_2R^{11}$, reaction of either a compound of formula II (or a protected derivative thereof) in which $X^1$ represents H, or a compound of formula XXIV (or a protected derivative thereof) in which the $L^1$ group is activated (for example as described hereinbefore), with a compound of formula VA, as hereinbefore defined, for example under conditions such as those described hereinbefore in respect of preparation of compounds of formula I (process (iia) above);

(bii) for compounds of formula II in which Q represents $C_{2-8}$ heteroalkylene (optionally substituted by one or more substituents selected from $G^1$), in which the heteroatom-containing group interrupting the alkylene chain is —N($R^{20}$)— and $X^1$ is as hereinbefore defined, or Q represents $C_{1-8}$ alkylene (optionally substituted by one or more substituents selected from $G^1$) and $X^1$ is a nitrogen-containing heterocycloalkyl group substituted by $X^2$, which group is attached to Q through a nitrogen atom in that group, reaction of a compound of formula XXV,

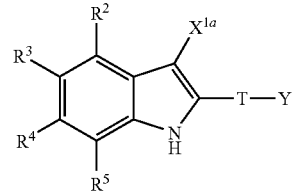

XXV wherein $X^{1a}$, $R^2$, $R^3$, $R^4$, $R^5$, T and Y are as hereinbefore defined by reductive amination in the presence of a compound of formula VII as hereinbefore defined;

(c) for compounds of formula II in which Q represents optionally substituted $C_{2-8}$ alkenylene or $C_{2-8}$ heteroalkenylene (in which a point of unsaturation is between the carbon atoms that are α and β to the indole ring), reaction of a corresponding compound of formula XXIV in which $L^1$ represents halo (e.g. iodo) with a compound of formula VIIIA, or a compound of formula XXV in which $X^{1a}$ represents —CHO with a compound of formula VIIIB or a compound of formula VIIIC as hereinbefore defined, for example under reaction conditions similar to those described hereinbefore in respect of preparation of compounds of formula I (process (iv)) above);

(d) for compounds of formula II in which Q represents optionally substituted, saturated $C_{2-8}$ allylene, saturated cycloalkylene, saturated $C_{2-8}$ heteroalkylene, saturated heterocycloalkylene, $C_{2-8}$ alkenylene, cycloalkenylene, $C_{2-8}$ heteroalkenylene or heterocycloalkenylene, reduction (e.g. hydrogenation) of a corresponding compound of formula II in which Q represents optionally substituted $C_{2-8}$ alkenylene, cycloalkenylene, $C_{2-8}$ heteroalkenylene, heterocycloalkenylene, $C_{2-8}$ alkynylene, cycloalkynylene, $C_{2-8}$ heteroalkynylene or heterocycloalkynylene (as appropriate) under conditions that are known to those skilled in the art;

(e) for compounds of formula II in which D represents a single bond, —C(O)—, —C($R^7$)($R^8$)—, $C_{2-8}$ alkylene or —S(O)$_2$—, reaction of a compound of formula XXVI,

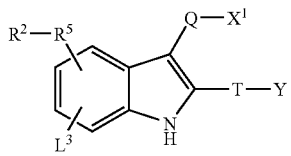

XXVI wherein Q, $X^1$, $L^3$, $R^2$-$R^5$, T and Y are as hereinbefore defined with a compound of formula X as hereinbefore defined, for example under reaction conditions similar to those described hereinbefore in respect of preparation of compounds of formula I (process (vi)) above;

(f) for compounds of formula II in which D represents —S—, —O— or $C_{2-4}$ alkynylene in which the triple bond is adjacent to E, reaction of a compound of formula XXVI as hereinbefore defined in which $L^3$ represents $L^2$ as hereinbefore defined (for example —B(OH)$_2$) with a compound of formula XI as hereinbefore defined, for example under reaction conditions similar to those described hereinbefore in respect of preparation of compounds of formula I (process (vii)) above;

(g) for compounds of formula II in which D represents —S(O)— or —S(O)$_2$—, oxidation of a corresponding compound of formula II in which D represents —S—;

(h) for compounds of formula II in which D represents —O— or —S—, reaction of a compound of formula XXVII,

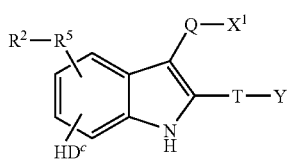

XXVII wherein $D^c$, Q, $X^1$, $R^2$-$R^5$, T and Y are as hereinbefore defined, with a compound of formula XIII as hereinbefore defined, for example under reaction conditions similar to those described hereinbefore in respect of preparation of compounds of formula I (process (ii)) above;

(i) for compounds of formula II in which T and Y are as hereinbefore defined, provided that when Y represents —C(O)$OR^{9a}$, —S(O)$_3R^{9e}$, —P(O)($OR^{9f}$)$_2$, —P(O)($OR^{9g}$)N($R^{10h}$)$R^{9h}$, —P(O)(N($R^{10i}$)$R^{9i}$)$_2$, —B($OR^{9y}$)$_2$ or —S(O)$_2$N($R^{10z}$)$R^{9z}$, $R^{9a}$, $R^{9e}$ to $R^{9i}$, $R^{9y}$, $R^{9z}$, $R^{10h}$, $R^{10i}$ and $R^{10z}$ are other than H, reaction of a compound of formula XXVIII,

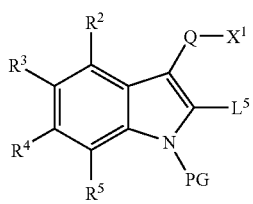

XXVIII wherein PG represents a suitable protecting group, such as —S(O)$_2$Ph, —C(O)O$^-$, —C(O)OtBu or —C(O)N(Et)$_2$) and $L^5$, Q, $X^1$, $R^2$, $R^3$, $R^4$ and $R^5$ are as hereinbefore defined, with a compound of formula XV as hereinbefore defined, for example under similar coupling conditions to those described hereinbefore in respect of process (x) above, followed by deprotection of the resultant compound under standard conditions;

(j) for compounds of formula II in which T represents a single bond, Y represents —C(O)$OR^{9a}$ and $R^{9a}$ represent H, reaction of a compound of formula XXIII in which $L^5$ represents an alkali metal, or —Mg-halide, with carbon dioxide, followed by acidification, for example under conditions such as those described in respect of preparation of compounds of formula I (process (xi)) above;

(k) for compounds of formula II in which T represents a single bond and Y represents —C(O)$OR^{9a}$, reaction of a corresponding compound of formula XXVIII in which $L^5$ is a suitable leaving group known to those skilled in the art (such as a sulfonate group (e.g. a triflate) or, preferably, a halo (e.g. bromo or iodo) group) with CO (or a reagent that is a suitable source of CO), in the presence of a compound of formula XVA as hereinbefore defined, or water, and an appropriate catalyst system under conditions such as those described hereinbefore;

(l) for compounds of formula II in which T represents a single bond, Y represents —B($OR^{9y}$)$_2$ and $R^{9y}$ represents H, reaction of a compound of formula XXVIII as hereinbefore defined with boronic acid or a protected derivative thereof (e.g. bis(pinacolato)diboron or triethyl borate), followed by deprotection of the resultant compound under standard conditions;

(m) for compounds of formula II in which T represents a single bond and Y represents —S(O)$_3R^{9e}$, reaction of a compound of formula XXVIII as hereinbefore defined with:
(A) for such compounds in which $R^{9e}$ represents H, either SO$_3$ (or a suitable source of SO$_3$ such as a SO$_3$*pyridine or SO$_3$*Et$_3$N complex) or with SO$_2$ followed by treatment with N-chlorosuccinimide and then hydrolysis;
(B) for such compounds in which $R^{9e}$ is other than H, chlorosulfonic acid followed by reaction with a compound of formula XX as defined hereinbefore in which $R^{9za}$ represents $R^{9e}$,
all under standard conditions such as those described hereinbefore in respect of preparation of compounds of formula I (process (xiv) above);

(n) for compounds of formula II in which T represents a single bond and Y represents

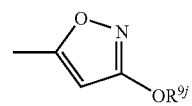

in which $R^{9j}$ represents hydrogen, reaction of a corresponding compound of formula II in which T represents a $C_2$ alkylene group substituted at the carbon atom that is attached to the indole ring system by $Z^1$, in which $Z^1$ represents =O and Y represents —C(O)$OR^{9a}$, in which $R^{9a}$ represents $C_{1-6}$ alkyl with hydroxylamine or an acid addition salt thereof, for example under reaction conditions similar to those described hereinbefore in respect of preparation of compounds of formula I (process (xv)) above;
(o) for compounds of formula II in which T represents a single bond and Y represents

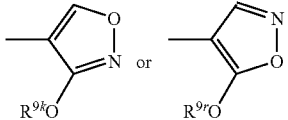

in which $R^{9k}$ and $R^{9r}$ represent hydrogen in each case, reaction of a corresponding compound of formula II in which T represents a $C_1$ alkylene group substituted with $G^1$, in which $G^1$ represents $-A^1-R^{12a}$, $A^1$ represents $—C(O)A^2-$, $A^2$ represents a single bond and $R^{12a}$ represents H, and Y represents $—C(O)OR^{9a}$, in which $R^{9a}$ represents methyl, or ethyl, respectively, with hydroxylamine or an acid addition salt thereof, for example under reaction conditions similar to those described hereinbefore in respect of preparation of compounds of formula I (process (xvi)) above;
(p) for compounds of formula II in which T represents a single bond and Y represents

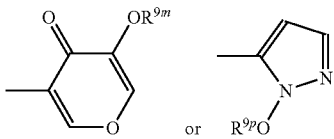

in which $R^{9m}$ and $R^{9p}$ represent hydrogen in each case, reaction of a corresponding compound of formula II in which T represents a single bond, Y represents $—B(OR^{9y})_2$ and $R^{9y}$ represents H with a compound of formula XV in which T represents a single bond, $Y^a$ represents

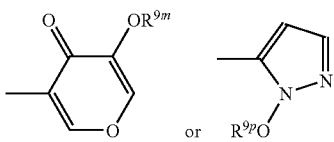

in which $R^{9m}$ and $R^{9p}$ represent hydrogen in each case, and $L^6$ preferably represents e.g. a halo group, such as Br, or I, respectively, or a protected derivative (e.g. at the OH group with, for example, a benzyl group) of either compound, for example under reaction conditions similar to those described hereinbefore in respect of preparation of compounds of formula I (process (xvii)) above;
(q) for compounds of formula II in which T represents a single bond and Y represents

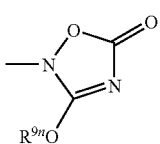

in which $R^{9n}$ represents hydrogen, reaction of a compound of formula XXIX,

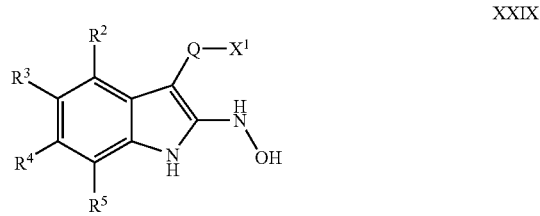

XXIX wherein Q, $X^1$, $R^1$, $R^2$, $R^3$, $R^4$ and $R^5$ are as hereinbefore defined with ethoxycarbonyl isocyanate, for example under reaction conditions similar to those described hereinbefore in respect of preparation of compounds of formula I (process (xviii)) above;
(r) for compounds of formula II in which T represents a single bond and Y represents

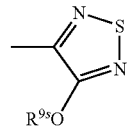

in which $R^{9s}$ represents hydrogen, reaction of a corresponding compound of formula II in which T represents a single bond and Y represents $—C(O)OR^{9a}$, in which $R^{9a}$ represents H with e.g. trimethylsilyl chloride (or the like), followed by reaction of the resultant intermediate with $N_4S_4$, for example under reaction conditions similar to those described hereinbefore in respect of preparation of compounds of formula I (process (xix)) above;
(s) for compounds of formula II in which T represents a single bond and Y represents

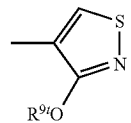

in which $R^{9t}$ represents hydrogen, reaction of a compound of formula XXX,

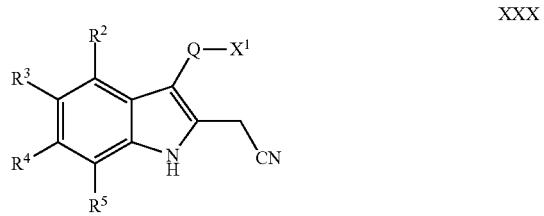

XXX wherein Q, $X^1$, $R^2$, $R^3$, $R^4$ and $R^5$ are as hereinbefore defined with NaH and $CS_2$ the presence of a suitable solvent (e.g. tetrahydrofuran), oxidation of the resultant intermediate in the presence of, for example, hydrogen peroxide, and finally heating the resultant intermediate in the presence of a strong acid, such as HCl, for example under reaction conditions similar to those described hereinbefore in respect of preparation of compounds of formula I (process (xx)) above;

(t) for compounds of formula II in which T represents a single bond and Y represents

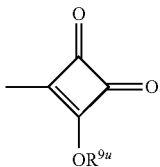

in which $R^{9u}$ represents hydrogen, reaction of a corresponding compound of formula II in which T represents $C_1$ alkylene, Y represents —C(O)OR$^{9a}$ and R$^{9a}$ represents H or, preferably, an activated (e.g. acid halide) derivative thereof with 1,1,2,2-tetraethoxyethene, for example under reaction conditions similar to those described hereinbefore in respect of preparation of compounds of formula I (process (xxi)) above;

(u) for compounds of formula II in which T represents a single bond and Y represents

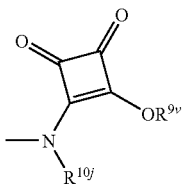

in which $R^{9v}$ and $R^{10j}$ independently represent hydrogen, reaction of a compound of formula XXIX as hereinbefore defined with 3,4-dimethoxycyclobutene-1,2-dione, for example under reaction conditions similar to those described hereinbefore in respect of preparation of compounds of formula I (process (xxii)) above;

(v) for compounds of formula II in which T represents a single bond and Y represents

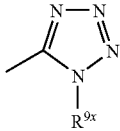

in which $R^{9x}$ represents hydrogen, reaction of a compound of formula XXXI,

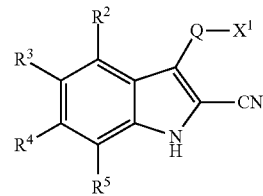

XXXI wherein Q, $X^1$, $R^2$, $R^3$, $R^4$ and $R^5$ are as hereinbefore defined with NaN$_3$ under standard conditions;

(w) for compounds of formula II in which T represents optionally substituted $C_{2-8}$ alkenylene or $C_{2-8}$ heteroalkylene (in which a point of unsaturation is between the carbon atoms that are α and β to the indole ring), reaction of a corresponding compound of formula XXXII,

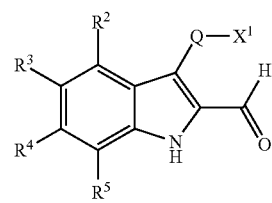

XXXII wherein Q, $X^1$, $R^2$, $R^3$, $R^4$ and $R^5$ are as hereinbefore defined with a compound of formula XIXA as hereinbefore defined, under standard Wittig reaction conditions;

(x) for compounds of formula II in which T represents optionally substituted, saturated $C_{2-8}$ alkylene, saturated cycloalkylene, saturated $C_{2-8}$ heteroalkylene, saturated heterocycloalkylene, $C_{2-8}$ alkenylene, cycloalkenylene, $C_{2-8}$ heteroalkenylene or heterocycloalkenylene, reduction (e.g. hydrogenation) of a corresponding compound of formula II in which T represents optionally substituted $C_{2-8}$ alkenylene, cycloalkenylene, $C_{2-8}$ heteroalkenylene, heterocycloalkenylene, $C_{2-8}$ alkynylene, cycloalkynylene, $C_{2-8}$ heteroalkynylene or heterocycloalkynylene (as appropriate);

(y) for compounds of formula II in which Y represents —C(O)OR$^{9a}$, —S(O)$_3$R$^{9e}$, —P(O)(OR$^{9f}$)$_2$, or —B(OR$^{9y}$)$_2$, in which R$^{9a}$, R$^{9e}$, R$^{9f}$ and R$^{9y}$ represent H, hydrolysis of a corresponding compound of formula II in which R$^{9a}$, R$^{9e}$, R$^{9f}$ or R$^{9y}$ (as appropriate) do not represent H, or, for compounds of formula II in which Y represents —P(O)(OR$^{9f}$)$_2$ or —S(O)$_3$R$^{9e}$, in which R$^{9f}$ and R$^{9e}$ represent H, a corresponding compound of formula II in which Y represents either —P(O)(OR$^{9g}$)N(R$^{10h}$)R$^{9h}$, —P(O)(N(R$^{10i}$)R$^{9i}$)$_2$ or —S(O)$_2$N(R$^{10z}$)R$^{9z}$ (as appropriate);

(z) for compounds of formula II in which Y represents —C(O)OR$^{9a}$, —S(O)$_3$R$^{9e}$, —P(O)(OR$^{9f}$)$_2$, —P(O)(OR$^{9g}$)N(R$^{10h}$)R$^{9h}$ or —B(OR$^{9y}$)$_2$ and R$^{9a}$, R$^{9e}$, R$^{9f}$, R$^{9g}$ and R$^{9y}$ (i.e. those R$^9$ groups attached to an oxygen atom) do not represent H:

(A) esterification of a corresponding compound of formula II in which R$^{9a}$, R$^{9e}$, R$^{9f}$, R$^{9g}$ and R$^{9y}$ represent H; or (B) trans-esterification of a corresponding compound of formula II in which R$^{9a}$, R$^{9e}$, R$^{9f}$, R$^{9g}$ and R$^{9y}$ do not represent H (and do not represent the same value of the corresponding $R^{9a}$, $R^{9e}$, $R^{9f}$, $R^{9g}$ and $R^{9y}$ group in the compound of formula II to be prepared), under standard conditions in the presence of the appropriate alcohol of formula XX as hereinbefore defined;

(aa) for compounds of formula I in which T represents a $C_1$ alkylene group substituted with $G^1$, in which $G^1$ represents $-A^1-R^{12a}$, $A^1$ represents $—C(O)A^2-$, $A^2$ represents a single bond and $R^{12a}$ represents H, and Y represents $—C(O)OR^{9a}$, in which $R^{9a}$ is other than H, reaction of a corresponding compound of formula II in which the $C_1$ alkylene group that T represents is unsubstituted with a $C_{1-6}$ alkyl formate in the presence of a suitable base; or (ab) for compounds of formula II in which Q and $X^1$ are as hereinbefore defined, provided that when $X^1$ or $X^2$ (as appropriate) represents $—C(O)OR^{9a}$, $—C(O)N(R^{10b})R^{9b}$, $—C(O)N(H)C(=NR^{9c})N(R^{10d})R^{9d}$, $—S(O)_3R^{9e}$, $—P(O)(OR^{9f})_2$, $—P(O)(OR^{9g})N(R^{10h})R^{9h}$, $—P(O)(N(R^{10i})R^{9i})_2$ or $—B(OR^{9y})_2$, $R^{9a}$ to $R^{9i}$, $R^{9y}$, $R^{10b}$, $R^{10d}$, $R^{10h}$ and $R^{10i}$ are other than H, reaction of a compound of formula XXIII,

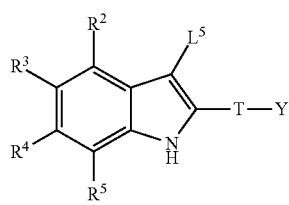

XXXIII wherein $L^5$, T, Y, $R^2$, $R^3$, $R^4$ and $R^5$ are as hereinbefore defined, with a compound of formula XXII as hereinbefore defined, or a protected derivative thereof, for example under reaction conditions similar to those described hereinbefore in respect of preparation of compounds of formula I (process (ii)) above, followed by (if necessary) deprotection under standard conditions;

(ac) for compounds of formula II in which Q represents a single bond, $X^1$ represents $—C(O)OR^{9a}$ and $R^{9a}$ represents H, reaction of a compound of formula XXXIII in which $L^5$ represents either an alkali metal or $—Mg$-halide with carbon dioxide, followed by acidification;

(ad) for compounds of formula II in which Q represents a single bond and $X^1$ represents $—C(O)OR^{9a}$ or $—C(O)N(R^{10b})R^{9b}$, reaction of a corresponding compound of formula XXXIII in which $L^5$ is a suitable leaving group with CO in the presence of a compound of formula XVA or XXIII as hereinbefore defined, for example under conditions such as those described in respect of process (xxxi) above;

(ae) for compounds of formula II in which Q represents a single bond, $X^1$ represents $—B(OR^{9y})_2$ and $R^{9y}$ represents H, reaction of a compound of formula XXXIII as hereinbefore defined with boronic acid or a protected derivative thereof (e.g. bis(pinacolato)diboron or triethyl borate), for example under conditions such as those described in respect of process (xxxii) above, followed by (if necessary) deprotection under standard conditions;

(af) for compounds of formula II in which Q represents a single bond and $X^1$ represents $—S(O)_3R^{9e}$, reaction of a compound of formula XXXIII as hereinbefore defined with:

(A) for such compounds in which $R^{9e}$ represents H, either $SO_3$ (or a suitable source of $SO_3$ such as a $SO_3$*pyridine or $SO_3$*$Et_3N$ complex) or with $SO_2$ followed by treatment with N-chlorosuccinimide and then hydrolysis;

(B) for such compounds in which $R^{9e}$ is other than H, chlorosulfonic acid followed by reaction with a compound of formula XX as defined hereinbefore in which $R^{9za}$ represents $R^{9e}$, all under standard conditions such as those described hereinbefore in respect of preparation of compounds of formula I (process (xxxiii) above);

(ag) for compounds of formula II in which $X^1$ or $X^2$ (as appropriate) represents $—C(O)OR^{9a}$, $S(O)_3R^{9e}$, $—P(O)(OR^{9f})_2$ or $—B(OR^{9y})_2$, in which $R^{9a}$, $R^{9e}$, $R^{9f}$ and $R^{9y}$ represent H, hydrolysis of a corresponding compound of formula II in which $R^{9a}$, $R^{9e}$, $R^{9f}$ or $R^{9y}$ (as appropriate) do not represent H, or for compounds of formula II in which $X^1$ or $X^2$ (as appropriate) represents $—C(O)OR^{9a}$ a or $—P(O)(OR^{9f})_2$, in which $R^{9a}$ and $R^{9f}$ represent H, a corresponding compound of formula II in which $X^1$ or $X^2$ (as appropriate) represents $—C(O)N(H)S(O)_2R^{11}$, $—P(O)(OR^{9g})N(R^{10h})R^{9h}$ or $—P(O)(N(R^{10i})R^{9i})_2$ (as appropriate);

(ah) for compounds of formula II in which $X^1$ or $X^2$ (as appropriate) represents $—C(O)OR^{9a}$, $—S(O)_3R^{9e}$, $—P(O)(OR^{9f})_2$, $—P(O)(OR^{9g})N(R^{10h})R^{9h}$ or $—B(OR^{9y})_2$ and $R^{9a}$, $R^{9e}$, $R^{9f}$, $R^{9g}$ and $R^{9y}$ (i.e. those $R^9$ groups attached to an oxygen atom) do not represent H:

(A) esterification of a corresponding compound of formula II in which $R^{9a}$, $R^{9e}$, $R^{9f}$, $R^{9g}$ and $R^{9y}$ represent H; or (B) trans-esterification of a corresponding compound of formula II in which $R^{9a}$, $R^{9e}$, $R^{9f}$, $R^{9g}$ and $R^{9y}$ do not represent H (and do not represent the same value of the corresponding $R^{9a}$, $R^{9e}$, $R^{9f}$, $R^{9g}$ and $R^{9y}$ group in the compound of formula II to be prepared), under standard conditions in the presence of the appropriate alcohol of formula XX as hereinbefore defined;

(ai) for compounds of formula II in which Q represents a $C_1$ alkylene group substituted with $G^1$, in which $G^1$ represents $-A^1-R^{12a}$, $A^1$ represents $—C(O)A^2-$, $A^2$ represents a single bond and $R^{12a}$ represents H, and $X^1$ represents $—C(O)OR^{9a}$, in which $R^{9a}$ is other than H, reaction of a corresponding compound of formula II in which the $C_1$ alkylene group that Q represents is unsubstituted with $C_{1-6}$ alkyl formate in the presence of a suitable base;

(aj) for compounds of formula II in which $X^1$ or $X^2$ (as appropriate) represents $—C(O)N(R^{10b})R^{9b}$, $—C(O)N(H)C(=NR^{9c})N(R^{10d})R^{9d}$, $—C(O)N(H)CN$ or $—C(O)N(H)S(O)_2R^{11}$ reaction of a corresponding compound of formula II in which $X^1$ represents $—C(O)OR^{9a}$ with a compound of formula XXIII as hereinbefore defined.

Compounds of formula IV may be prepared as follows:

(a) Reaction of a compound of formula XXIV as hereinbefore defined with a compound of formula XXXIV, $R^1L^2$      XXXV wherein $R^1$ and $L^2$ are as hereinbefore defined or a compound of formula III as hereinbefore defined, for example under reaction conditions similar to those described hereinbefore in respect of preparation of compounds of formula I (processes (ii) and (i), respectively) above;

(b) for compounds of formula IV in which $L^1$ represents halo, reaction of a compound of formula XXXV,

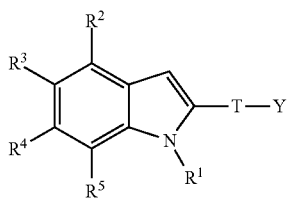

wherein $R^1$, $R^2$, $R^3$, $R^4$, $R^5$, T and Y are as hereinbefore defined with a reagent or mixture of reagents known to be a source of halide atoms. For example, for bromide atoms, N-bromosuccinimide, bromine or 1,2-dibromotetrachloroethane may be employed, for iodide atoms, iodine, diiodoethane, diiodotetrachloroethane or a mixture of NaI or KI and N-chlorosuccinimide may be employed, for chloride atoms, N-chlorosuccinimide may be employed and for fluoride atoms, 1-(chloromethyl)-4-fluoro-1,4-diazoniabicyclo[2.2.2]octane bis(tetrafluoroborate), 1-fluoropyridinium triflate, xenon difluoride, $CF_3OF$ or perchloryl fluoride may be employed. This reaction may be carried out in a suitable solvent (e.g. acetone, benzene or dioxane) under conditions known to the skilled person; or (c) for compounds of formula IV wherein $L^1$ represents a sulfonate group, reaction of a compound of formula XXXVI,

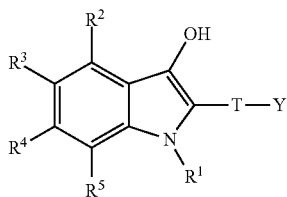

wherein $R^1$, $R^2$, $R^3$, $R^4$, $R^5$, T and Y are as hereinbefore defined with an appropriate reagent for the conversion of the hydroxyl group to the sulfonate group (e.g. tosyl chloride, mesyl chloride, triflic anhydride and the like) under conditions known to those skilled in the art.

Compounds of formula VI may be prepared by:
(a) for compounds of formula VI in which D represents a single bond, —C(O)—, —C($R^7$)($R^8$)—, $C_{2-4}$ alkylene or —S(O)$_2$—, reaction of a compound of formula XXXVII,

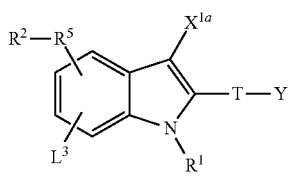

wherein $X^{1a}$, $L^3$, $R^1$, $R^2$-$R^5$, T and Y are as hereinbefore defined ($L^3$ in particular may represent halo, such as bromo) with a compound of formula X as hereinbefore defined (in which $L^4$ may in particular represent —B(OH)$_2$), for example under reaction conditions similar to those described hereinbefore in respect of preparation of compounds of formula I (process (vi)) above;

(b) reaction of a compound of formula XXV as hereinbefore defined with a compound of formula III as hereinbefore defined, for example under reaction conditions similar to those described hereinbefore in respect of preparation of compounds of formula I (process (i)) above; or (c) for compounds of formula VI in which $X^{1a}$ represents —CHO, reaction of a corresponding compound of formula XXXV as hereinbefore defined with a mixture of DMF and, for example, oxalyl chloride, phosgene or P(O)Cl$_3$ (or the like) in an appropriate solvent system (e.g. DMF or dichloromethane).

Compounds of formula IX may be prepared by reaction of a compound of formula XXVI as hereinbefore defined, with a compound of formula III as hereinbefore defined, for example under reaction conditions similar to those described hereinbefore in respect of preparation of compounds of formula I (process (i)) above.

Compounds of formula IX in which $L^3$ represents $L^2$ may be prepared by reaction of a compound of formula IX in which $L^3$ represents $L^1$, with an appropriate reagent for the conversion of the $L^1$ group to the $L^2$ group. This conversion may be performed by methods known to those skilled in the arts for example, compounds of formula IX, in which $L^3$ is 4,4,5,5-tetramethyl-1,3,2-dioxaborolan-2-yl may be prepared by reaction of the reagent bis(pinacolato)diboron with a compound of formula IX in which $L^3$ represents $L^1$, for example under reaction conditions similar to those described hereinbefore in respect of preparation of compounds of formula I (process (ii)) above).

Compounds of formulae XIV, XXI, XXVIII and XXXIII, in which $L^5$ represents an appropriate alkali metal, such as lithium may be prepared by reaction of, in the case of a compound of formula XIV, or XXVIII, a compound of formula XXXVIII,

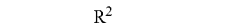

or, in the case of a compound of formula XXI, or XXXIII, a compound of formula XXXIX,

XXXIX wherein, in both cases, $R^z$ represents $R^1$ (in the case of compounds of formulae XIV and XXI) or PG (in the case of compounds of formulae XXVIII and XXXII), and PG, Q, $X^1$, T, Y, $R^1$, $R^2$, $R^3$, $R^4$ and $R^5$ are as hereinbefore defined, with an appropriate base, such lithium diisopropylamide or BuLi under standard conditions. Compounds of formulae XIV, XXI, XXVIII and XXXIII in which L⁵ represents another group (such as a zinc-based leaving group or halo) may be prepared by an appropriate exchange reaction that will be well known to those skilled in the art. For example, compounds of formulae XIV, XXI, XXVIII and XXXIII in which L⁵ represents —Mg-halide may be prepared from a corresponding compound of formula XIV, XXI, XXVIII or XXXIII (as appropriate) in which L⁵ represents halo, for example under conditions such as those described hereinbefore in respect of process step (vi). Compounds of formulae XIV, XXI, XXVIII and XXXII in which L⁵ represents a group such as a zinc-based leaving group, halo or a boronic acid may be prepared by reacting a corresponding compound of formula XIV, XXI, XXVIII or XXXIII in which L⁵ represents an alkali metal with an appropriate reagent for introduction of the relevant group, for example by a metal exchange reaction (e.g. a Zn transmetallation), by reaction with a suitable reagent for the introduction of a halo group (for example, a reagent described hereinbefore in respect of preparation of compounds of formula IV (process step (b)), for the introduction of a boronic acid group, reaction with, for example, boronic acid or a protected derivative thereof (e.g. bis(pinacolato)diboron or triethyl borate). All of these reactions may be followed by (if necessary) deprotection under standard conditions;

Compounds of formulae XVII and XXX, and XIX and XII, may be prepared by reduction of a corresponding compound of formula I, or of formula II, respectively, in which T represents a single bond and Y represents —C(O)OR⁹ᵃ, to the corresponding primary alcohol (using e.g. LiAlH₄), followed by reaction of the relevant resultant intermediate with, in the case of preparation of a compound of formula XVII or XXX, SOCl₂, MeSOCl₂ or bromine followed by a suitable source of cyanide ions (e.g. NaCN or KCN) or, in the case of preparation of a compound of formula XIX or XXXII, oxidation to the aldehyde in the presence of a suitable oxidising agent, such as MnO₂, in all cases under reaction conditions that will be well known to those skilled in the art. In the case of the latter, the skilled person will appreciate that an appropriate reagent for the reduction of the ester group directly to the aldehyde may be employed (e.g. DIBAL).

Compounds of formulae XVIII and XXXI may be prepared by conversion of a corresponding compound of formula I, or of formula II, respectively in which T represents a single bond and Y represents —C(O)OR⁹ᵃ, to the corresponding primary amide (e.g. when R⁹ᵃ is H, by reaction with SOCl₂ followed by ammonia or, when R⁹ᵃ is other than H, by reaction with ammonia), followed by dehydration of the resultant intermediate in the presence of a suitable dehydrating agent, such as POCl₃, in all cases under reaction conditions that will be well known to those skilled in the art.

Compounds of formula XXV may be prepared by standard techniques. For example compounds of formula XXIV in which D represents a single bond, —C(O)—, —C(R⁷)(R⁸)—, C₂₋₄ alkylene or —S(O)₂— may be prepared by reaction of a compound of formula XL,

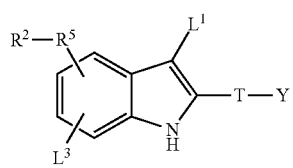

XL wherein L¹, L³, R²-R⁵ T and Y are as hereinbefore defined with a compound of formula X as hereinbefore defined, for example under reaction conditions similar to those described hereinbefore in respect of preparation of compounds of formula I (process (vi)) above.

Compounds of formulae III, V, VA, VII, VIIIA, VIIIB, VIIIC, X, XI, XII, XIII, XV, XVA, XVI, XIXA, XX, XXII, XXIII, XXV, XXVI, XXVII, XXIX, XXXIV, XXXV, XXXVI, XXXVII, XXXVIII, XXXIX and XL are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991.

Indoles of formulae II, IV, VI, IX, XII, XIV, XVI, XVII, XVIII, XIX, XXI, XXIV, XXV, XXVI, XXVII, XXVIII, XXIX, XXX, XXXI, XXXII, XXXIII, XXXV, XXXVI, XXXVII, XXVIII, XIX and XL may also be prepared with reference to a standard heterocyclic chemistry textbook (e.g. "*Heterocyclic Chemistry*" by J. A. Joule, K. Mills and G. F. Smith, 3ʳᵈ edition, published by Chapman & Hall or "*Comprehensive Heterocyclic Chemistry II*" by A. R. Katritzky, C. W. Rees and E. F. V. Scriven, Pergamon Press, 1996) and/or made according to the following general procedures.

For example, compounds of formulae II, XXVI and XXVII may be prepared by reaction of a compound of formula XLI,

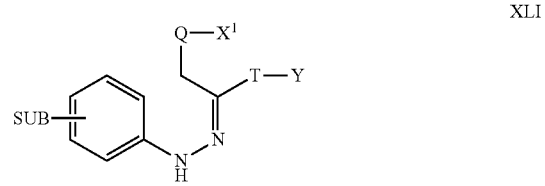

XLI wherein SUB represents the substitution pattern that is present in the relevant compound to be formed (in this case, the compound of formula II, XXVI or XXIII, respectively) and Q, X¹, T and Y are as hereinbefore defined, under Fischer indole synthesis conditions known to the person skilled in the art.

Compounds of formula II and XXVI may alternatively be prepared by reaction of a compound of formula XLII,

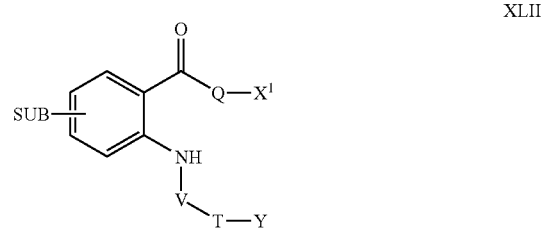

XLII wherein V represents either —C(O)— or —CH₂—, and Q, SUB, X¹, T and Y are as hereinbefore defined. When V represents —C(O)—, the intramolecular cyclisation may be induced by a reducing agent such as TiCl₃/C₈K, TiCl₄/Zn or SmI₂ under conditions known to the skilled person, for example, at room temperature in the presence of a polar aprotic solvent (such as THF). When V represents —CH₂—, the reaction may be performed in the presence of base under intramolecular condensation reaction conditions known to the skilled person.

Compounds of formula XXVII in which $D^c$ represents O and the —OH group is at the 5-position (i.e. $R^3$), $R^2$, $R^4$ and $R^5$ all represent H and Q represents a single bond, may be prepared by way of Nenitzescu indole synthesis by reaction of a compound of formula XLIII,

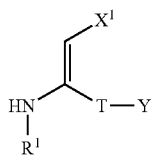

XLIII or a tautomer thereof, wherein $X^1$ is as hereinbefore defined, and preferably —C(O)OR$^{9a}$, and T, Y, $R^1$ and $R^{9a}$ are as hereinbefore defined with benzoquinone under conditions that are known to those skilled in the art.

Compounds of formula XXXIX may be prepared by reaction of a compound of formula XLIV,

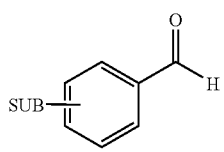

XLIV wherein SUB is as hereinbefore defined with a compound of formula XLV,

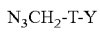 XLV wherein T is as hereinbefore defined and preferably a single bond or optionally substituted arylene or heteroarylene, and Y is as hereinbefore defined and, when T represents a single bond, preferably represents —C(O)OR$^{9a}$ in which R$^{9a}$ preferably does not represent hydrogen, under conditions known to the person skilled in the art (i.e. conditions to induce a condensation reaction, followed by a thermally induced cyclisation), followed by protection at the 1 (N)-position.

Compounds of formula XLI may be prepared by:

(a) reaction of a compound of formula XLVI,

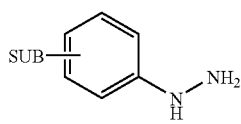

XLVI wherein SUB is as hereinbefore defined with a compound of formula XLVII,

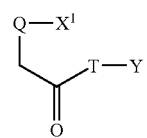

XLVII wherein Q, $X^1$, T and Y are as hereinbefore defined under condensation conditions known to the skilled person;

(b) reaction of a compound of formula XLVIII,

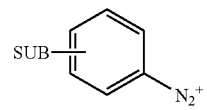

XLVIII wherein SUB is as hereinbefore defined with a compound of formula XLIX,

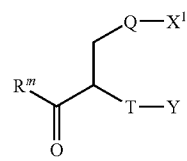

XLIX wherein R$^m$ represents OH, O—C$_{1-6}$ alkyl or C$_{1-6}$ alkyl and Q, $X^1$, T and Y are as hereinbefore defined, for example under Japp-Klingemann conditions known to the skilled person.

Compounds of formula XLII may be prepared by reaction of a compound of L,

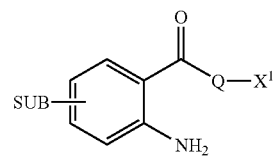

L wherein SUB, Q and $X^1$ are as hereinbefore defined with a compound of formula LI,

 LI wherein T, Y and V are as hereinbefore defined, under standard coupling conditions.

Compounds of formulae XLIII, XLIV, XLV, XLVI, XLVII, XLVIII, XLIX, L and LI are either commercially available, are known in the literature, or may be obtained either by analogy with the processes described herein, or by conventional synthetic procedures, in accordance with standard techniques, from available starting materials using appropriate reagents and reaction conditions. In this respect, the skilled reader may refer to inter alia "*Comprehensive Organic Synthesis*" by B. M. Trost and I. Fleming, Pergamon Press, 1991.

The substituents $X^1$, T, Y, $R^1$, $R^2$, $R^3$, $R^4$, $R^5$ and Q in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, and etherifications. The precursor groups can be changed to a different such group, or to the groups defined in formula I, at any time during the reaction sequence. For example, in cases where Y represents —C(O)OR$^{9a}$ and R$^{9a}$ does not initially represent hydrogen (so providing an ester functional group), the skilled person will appreciate that at any stage during the synthesis (e.g. the final step), the relevant substituent may be hydrolysed to form a carboxylic acid functional group (in which case R$^{9a}$ will be hydrogen). In this respect, the skilled person may also refer to "*Comprehensive Organic Functional Group Transformations*" by A. R. Katritzky, O. Meth-Cohn and C. W. Rees, Pergamon Press, 1995.

Compounds of the invention may be isolated from their reaction mixtures using conventional techniques.

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are -well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3$^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention for use as a pharmaceutical.

Although compounds of the invention may possess pharmacological activity as such certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

By "prodrug of a compound of the invention", we include compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention (including, but not limited to, compounds of formula I in which R$^{9a}$ is other than hydrogen) may possess no or minimal pharmacological activity as such, but may be administered parenterally or orally, and thereafter be metabolised in the body to form compounds of the invention that possess pharmacological activity as such (including, but not limited to, corresponding compounds of formula I, in which R$^{9a}$ represents hydrogen). Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity.

Compounds of the invention are particularly useful because they may inhibit the activity of a member of the MAPEG family.

Compounds of the invention are particularly useful because they may inhibit (for example selectively) the activity of prostaglandin E synthases (and particularly microsomal prostaglandin E synthase-1 (mPGES-1)), i.e. they prevent the action of mPGES-1 or a complex of which the mPGES-1 enzyme forms a part, and/or may elicit a mPGES-1 modulating effect, for example as may be demonstrated in the test described below. Compounds of the invention may thus be useful in the treatment of those conditions in which inhibition of a PGES, and particularly mPGES-1, is required.

Compounds of the invention may inhibit the activity of leukotriene C$_4$ (LTC$_4$), for example as may be shown in a test such as that described in *Eur. J. Biochem.*, 208, 725-734 (1992), and may thus be useful in the treatment of those conditions in which inhibition of LTC$_4$ is required. Compounds of the invention may also inhibit the activity of 5-lipoxygenase-activating protein (FLAP), for example as may be shown in a test such as that described in *Mol. Pharmacol.*, 41, 873-879 (1992).

Compounds of the invention are thus expected to be useful in the treatment of inflammation.

The term "inflammation" will be understood by those skilled in the art to include any condition characterised by a localised or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white blood cells, loss of function and/or any other symptoms known to be associated with inflammatory conditions.

The term "inflammation" will thus also be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Accordingly, compounds of the invention may be useful in the treatment of asthma, chronic obstructive pulmonary disease, pulmonary fibrosis, inflammatory bowel disease, irritable bowel syndrome, inflammatory pain, fever, migraine, headache, low back pain, fibromyalgia, myofascial disorders, viral infections (e.g. influenza, common cold, herpes zoster, hepatitis C and AIDS), bacterial infections, fungal infections, dysmenorrhea, burns, surgical or dental procedures, malignancies (e.g. breast cancer, colon cancer, and prostate cancer), hyperprostaglandin E syndrome, classic Bartter syndrome, atherosclerosis, gout, arthritis, osteoarthritis, juvenile arthritis, rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, neurodegenerative disorders such as Alzheimer's disease and multiple sclerosis, autoimmune diseases, allergic disorders, rhinitis, ulcers, coronary heart disease, sarcoidosis and any other disease with an inflammatory component.

Compounds of the invention may also have effects that are not linked to inflammatory mechanisms, such as in the reduction of bone loss in a subject. Conditions that may be mentioned in this regard include osteoporosis, osteoarthritis, Paget's disease and/or periodontal diseases. Compounds the invention may thus also be useful in increasing bone mineral density, as well as the reduction in incidence and/or healing of fractures, in subjects.

Compounds of the invention are indicated both in the therapeutic and/or prophylactic treatment of the above-mentioned conditions.

According to a further aspect of the present invention, there is provided a method of treatment of a disease which is associated with, and/or which can be modulated by inhibition of, a member of the MAPEG family such as a PGES (e.g. mPGES-1), $LTC_4$ and/or FLAP and/or a method of treatment of a disease in which inhibition of the activity of a member of the MAPEG family such as PGES (and particularly mPGES-1), $LTC_4$ and/or FLAP is desired and/or required (e.g. inflammation), which method comprises administration of a therapeutically effective amount of a compound of the invention, as hereinbefore defined, to a patient suffering from, or susceptible to, such a condition.

"Patients" include mammalian (including human) patients.

The term "effective amount" refers to an amount of a compound, which confers a therapeutic effect on the treated patient. The effect may be objective (i.e. measurable by some test or marker) or subjective (i.e. the subject gives an indication of or feels an effect).

Compounds of the invention will normally be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent or carrier.

Compounds of the invention may also be combined with other therapeutic agents that are useful in the treatment of inflammation (e.g. NSAIDs and coxibs).

According to a further aspect of the invention, there is provided a combination product comprising:
(A) a compound of the invention, as hereinbefore defined; and
(B) another therapeutic agent that is useful in the treatment of inflammation, wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention as hereinbefore defined, another therapeutic agent that is useful in the treatment of inflammation, and a pharmaceutically-acceptable adjuvant, diluent or carrier; and
(2) a kit of parts comprising components:
(a) a pharmaceutical formulation including a compound of the invention, as hereinbefore defined, in admixture with a pharmaceutically-acceptable adjuvant, diluent or carrier; and
(b) a pharmaceutical formulation including another therapeutic agent that is useful in the treatment of inflammation in admixture with a pharmaceutically-acceptable adjuvant, diluent or carrier, which components (a) and (b) are each provided in a form that is suitable for administration in conjunction with the other.

Compounds of the invention may be administered at varying doses. Oral, pulmonary and topical dosages may range from between about 0.01 mg/g of body weight per day (mg/kg/day) to about 100 mg/kg/day, preferably about 0.01 to about 10 mg/kg/day, and more preferably about 0.1 to about 5.0 mg/kg/day. For e.g. oral administration, the compositions typically contain between about 0.01 mg to about 500 mg, and preferably between about 1 mg to about 100 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily.

In any event, the physician, or the skilled person, will be able to determine the actual dosage which will be most suitable for an individual patient, which is likely to vary with the rout-e of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited and such are within the scope of this invention.

Compounds of the invention may have the advantage that they are effective, and preferably selective, inhibitors of a member of MAPEG family, e.g. inhibitors of prostaglandin E synthases (PGES) and particularly microsomal prostaglandin E synthase-1 (mPGES-1). The compounds of the invention may reduce the formation of the specific arachidonic acid metabolite $PGE_2$ without reducing the formation of other COX generated arachidonic acid metabolites, and thus may not give rise to the associated side-effects mentioned hereinbefore.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

Biological Test

In the assay mPGES-1 catalyses the reaction where the substrate $PGH_2$ is converted to $PGE_2$. mPGES-1 is expressed in *E. coli* and the membrane fraction is dissolved in 20 mM NaPi-buffer pH 8.0 and stored at −80° C. In the assay mPGES-1 is dissolved in 0.1M KPi-buffer pH 7.35 with 2.5 mM glutathione. The stop solution consists of $H_2O$/MeCN (7/3), containing $FeCl_2$ (25 mM) and HCl (0.15 M). The assay is performed at room temperature in 96-well plates. Analysis of the amount of $PGE_2$ is performed with reversed phase HPLC (Waters 2795 equipped with a 3.9×150 mm C18 column). The mobile phase consists of $H_2O$/MeCN (7/3), containing TFA (0.056%), and absorbance is measured at 195 nm with a Waters 2487 UV-detector.

The following is added chronologically to each well:
1. 100 µL mPGES-1 in KPi-buffer with glutathione. Total protein concentration: 0.02 mg/mL.
2. 1 µL inhibitor in DMSO. Incubation of the plate at room temperature for 25 minutes.
3. 4 µL of a 0.25 mM $PGH_2$ solution. Incubation of the plate at room temperature for 60 seconds.
4. 1100 µL stop solution.

180 µL per sample is analyzed with HPLC.

EXAMPLES

The invention is illustrated by way of the following examples, in which the following abbreviations may be employed:
cy cyclohexyl
dba dibenzylideneacetone
DIBAL diisobutylaluminium hydride
DMAP 4,4-dimethylaminopyridine
DMF dimethylformamide
DMSO dimethylsulfoxide
DPEphos bis-(2-diphenylphosphinophenyl)ether
EtOAc ethyl acetate
HPLC High Pressure Liquid Chromatography
MeCN acetonitrile
MS mass spectrum
NMR nuclear magnetic resonance
rt room temperature
TMEDA N,N,N',N'-tetramethylethylendiamine
TFA trifluoroacetic acid
THF tetrahydrofuran
xantphos 9,9-dimethyl-4,5-bis(diphenylphosphino)-xanthene Starting materials and chemical reagents specified in the syntheses described below are commercially available from, e.g. Sigma-Aldrich Fine Chemicals.

Example 1

2-Carboxymethyl-1-(4-diethylaminophenyl)-5-(4-trifluoromethylphenoxy)indole-3-carboxylic acid (a) 3-(4-Diethylaminophenylamino)-pent-2-enedioic acid diethyl ester A mixture of N,N-diethyl-1,4-phenylenediamine (7.1 g, 42.8 mmol), 1,3-acetone-dicarboxylic acid diethyl ester (7.8 mL, 42.8 mmol), a catalytic amount of p-toluenesulfonic acid and $CHCl_3$ (50 mL) was heated at reflux or 6 h while the water was removed with a Dean-Stark-trap. The mixture was concentrated and the sub-title compound was used in the subsequent step without further purification.

(b) 1-(4-Diethylaminophenyl)-2-ethoxycarbonylmethyl-5-hydroxyindole-3-carboxylic acid ethyl ester A mixture of 3-(4-diethylaminophenylamino)pent-2-enedioic acid diethyl ester (11.9 g, 34.2 mmol, see step (a) above), 1,4-benzoquinone (4.62 g, 42.8 mmol) and anhydrous MeCN (70 mL) was stirred at 70° C. for 2 d and at 4° C. for 1 d. The solid was collected and recrystallized from MeCN. Yield 4.5 g (30%).

(c) 1-(4-Diethylaminophenyl)-2-ethoxycarbonylmethyl-5-(4-trifluoromethylphenoxy)indole-3-carboxylic acid ethyl ester A mixture of 1-(4-diethylaminophenyl)-2-ethoxycarbonylmethyl-5-hydroxyindole-3-carboxylic acid ethyl ester (200 mg, 0.46 mmol, see step (b) above), $Cu(OAc)_2$ (83 mg, 0.46 mmol), 4-trifluoromethylbenzeneboronic acid (129 mg, 0.68 mmol), pyridine (55 µL, 0.68 mmol), $Et_3N$ (94 µL, 0.68 mmol), molecular sieves 4 Å and anhydrous $CH_2Cl_2$ (10 mL) was stirred at rt for 2 d, filtered, concentrated and purified by chromatography to give the sub-title compound. Yield 150 mg, 56%.

(d) 2-Carboxymethyl-1-(4-diethylaminophenyl)-5-(4-trifluoromethylphenoxy)indole-3-carboxylic acid A mixture of 1-(4-diethylaminophenyl)-2-ethoxycarbonylmethyl-5-(4-trifluoromethylphenoxy)indole-3-carboxylic acid ethyl ester (150 mg, 0.26 mmol, see step (c) above), NaOH (aq, 2 M, 2 mL) and dioxane (2 µL) was stirred at 120° C. for 6 h, cooled and acidified with HCl (aq, 1 M) to pH 4 and extracted with EtOAc. The combined extracts were washed with water and brine, dried ($Na_2SO_4$), concentrated and purified by chromatography to give the title compound as a gray powder. Yield 90 mg (66%), mp 234-236° C.

200 MHz $^1$H-NMR (DMSO-$d_6$), δ: 1.09-1.29 (m, 6H); 3.23-3.61 (m, 4H); 3.85 (s, 1H); 6.81 (d, J=8.3 Hz, 2H); 6.95 (dd, J=8.8 and 2.1 Hz, 1H); 7.02-7.27 (m, 5H); 7.69 (d, J=8.3 Hz, 2H); 7.80 (d, 1H).

Example 2

2-Carboxymethyl-1-(4-chlorophenyl)-5-(4-trifluoromethylphenoxy)indole-3-carboxylic acid (a) 3-(4-Chlorophenylamino)pent-2-enedioic acid diethyl ester The sub-title compound was prepared in accordance with step (a) Example 1 from 4-chloroaniline.

(b) 1-(4-Chlorophenyl)-2-ethoxycarbonylmethyl-5-hydroxyindole-3-carboxylic acid ethyl ester The sub-title compound was prepared in accordance with step (b) Example 1 from 3-(4-chloroaminophenylamino)pent-2-enedioic acid diethyl ester (42.8 mmol, see step (a) Example 2). Yield 2.8 g (16%).

(c) 1-(4-Chlorophenyl)-2-ethoxycarbonylmethyl-5-(4-trifluoromethylphenoxy)indole-3-carboxylic acid ethyl ester The sub-title compound was prepared in accordance with step (c) Example 1 from 1-(4-chlorophenyl)-2-ethoxycarbonylmethyl-5-hydroxyindole-3-carboxylic acid ethyl ester (185 mg, 0.46 mmol, see step (b) Example 2) and 4-trifluoromethylbenzeneboronic acid (129 mg, 0.68 mmol). Yield 145 mg (58%).

(d) 2-Carboxymethyl-1-(4-chlorophenyl)-5-(4-trifluoromethylphenoxy)-1H-indole-3-carboxylic acid A mixture of 1-(4-chlorophenyl)-2-ethoxycarbonylmethyl-5-(4-trifluoromethylphenoxy)indole-3-carboxylic acid ethyl ester (140 mg, 0.25 mmol, see step (c) Example 2), NaOH (aq, 2M, 2 mL) and dioxane (2 mL) were heated at 120° C. for 4.5 h, cooled, diluted with $H_2O$, acidified to pH 2 with HCl (aq, 1 M) and extracted with EtOAc. The combined extracts were washed with brine, dried ($Na_2SO_4$) and concentrated. The residue was treated with $CH_2Cl_2$ (2 mL) to give the title compound as a white solid which was recrystallised from $CH_2Cl_2$/EtOH (9:1). Yield 45 mg (37%), mp 974-276° C.

200 MHz $^1$H-NMR (DMSO-$d_6$), δ: 4.01 (s, 2H); 6.96-7.22 (m, 4H); 7.51 (d, J=8.2 Hz, 2H); 7.63-7.88 (m, 5H); 12.3-13.0 (br s, 2H).

Example 3

2-Carboxymethyl-1-phenyl-5-(4-trifluoromethylphenoxy)indole-3-carboxylic acid (a) 3-Phenylaminopent-2-enedioic acid diethyl ester The sub-title compound was prepared in accordance with step (a) Example 1 from aniline.

(b) 2-Ethoxycarbonylmethyl-5-hydroxy-1-phenylindole-3-carboxylic acid ethyl ester The sub-title compound was prepared in accordance with step (b) Example 1 from 3-phenylaminopent-2-enedioic acid diethyl ester (30 mmol, see step (a) Example 3) Yield 0.92 g (8%).

(c) 2-Ethoxycarbonylmethyl-1-phenyl-5-(4-trifluoromethylphenoxy)indole-3-carboxylic acid ethyl ester The sub-title compound was prepared in accordance with step (c) Example 1 from 2-ethoxycarbonylmethyl-5-hydroxy-1-phenylindole-3-carboxylic acid ethyl ester (170 mg, 0.46 mmol, see step (b) Example 3) and 4-trifluoromethylphenylboronic acid (129 mg, 0.68 mmol). Yield 150 mg (64%).

(d) 2-Carboxymethyl-1-phenyl-5-(4-trifluoromethylphenoxy)indole-3-carboxylic acid The title compound was prepared in accordance with step (d) Example 2 from 2-ethoxycarbonylmethyl-1-phenyl-5-(4-trifluoromethylphenoxy)indole-3-carboxylic acid ethyl ester (130 mg, 0.25 mmol, see step (c) Example 3). The compound was purified by recrystallisation from $CH_2Cl_2$/EtOH (9:1). Yield 45 mg (39%), mp 255-257° C.

mp 200 MHz $^1$H-NMR (DMSO-$d_6$), δ: 3.99 (s, 2H); 6.97-7.07 (m, 2H); 7.11 (d, J=8.3 Hz, 2H); 7.41-7.52 (m, 2H); 7.59-7.75 (m, 5H); 7.79 (d, J=1.7 Hz, 1H); 12.45-12.6 (br s, 2H).

Example 4

2-Carboxymethyl-1-(4-methoxyphenyl)-5-(4-trifluoromethylphenoxy)indole-3-carboxylic acid (a) 3-(4-Methoxyphenylamino)pent-2-enedioic acid diethyl ester The sub-title compound was prepared in accordance with step (a) Example 1 from p-anisidine.

(b) 2-Ethoxycarbonylmethyl-5-hydroxy-1-(4-methoxyphenyl)indole-3-carboxylic acid ethyl ester The sub-title compound was prepared in accordance with step (b) Example 1 from 3-(4-methoxyphenylamino)pent-2-enedioic acid diethyl ester (3.00 g, 9.8 mmol, see step (a) Example 4). Yield 1.55 g (41%).

(c) 1-(4-Methoxyphenyl)-2-ethoxycarbonylmethyl-5-(4-trifluoromethylphenoxy)indole-3-carboxylic acid ethyl ester The sub-title compound was prepared in accordance with step (c) Example 1 from 2-ethoxycarbonylmethyl-5-hydroxy-1-(4-methoxyphenyl)indole-3-carboxylic acid ethyl ester (176 mg, 0.46 mmol, see step (b) Example 4) and 4-trifluoromethylphenylboronic acid (129 mg, 0.68 mmol) Yield 140 mg (56%).

(d) 2-Carboxymethyl-1-(4-methoxyphenyl)-5-(4-trifluoromethylphenoxy)indole-3-carboxylic acid The title compound was prepared in accordance with step (d) Example 2 from 1-(4-methoxyphenyl)-2-ethoxycarbonylmethyl-5-(4-trifluoromethylphenoxy)indole-3-carboxylic acid ethyl ester (125 mg 0.23 mmol, see step (c) Example 4). Yield 72 mg (64%), mp 248-250° C.

200 MHz $^1$H-NMR (DMSO-$d_6$), δ: 3.86 (s, 3H); 3.97 (s, 2H); 6.95-7.06 (m, 2H); 7.10 (d, J=8.5 Hz; 2H); 7.14-7.25 (m, 2H); 7.38 (d, J=8.7 Hz; 2H); 7.69 (d, J=8.5 Hz; 2H); 7.77 (d, 1H): 12.3-12.7 (br s, 2H).

Example 5

2-Carboxymethyl-1-(3-methoxyphenyl-5-(4-trifluoromethylphenoxy)indole-3-carboxylic acid (a) 3-(3-Methoxyphenylamino)pent-2-enedioic acid diethyl ester The sub-title compound was prepared in accordance with step (a) Example 1 from m-anisidine.

(b) 2-Ethoxycarbonylmethyl-1-(3-methoxyphenyl)-5-hydroxyindole-3-carboxylic acid ethyl ester The sub-title compound was prepared in accordance with step (b) Example 1 from 3-(3-methoxy-phenylamino)pent-2-enedioic acid diethyl ester (30 mmol, see step (a) Example 5). Yield 875 mg (8%).

(c) 2-Ethoxycarbonylmethyl-1-(3-methoxyphenyl)-5-(4-trifluoromethylphenoxy)indole-3-carboxylic acid ethyl ester The sub-title compound was prepared in accordance with step (c) Example 1 from 2-ethoxycarbonylmethyl-5-hydroxy-1-(3-methoxyphenyl)indole-3-carboxylic acid ethyl ester (183 mg, 0.46 mmol, see step (b) Example 5) and 4-trifluoromethylphenylboronic acid (129 mg, 0.68 mmol). Yield 170 mg (68%).

(d) 9-Carboxymethyl-1-(3-methoxyphenyl-5-(4-trifluoromethylphenoxy)indole-3-carboxylic acid The title compound was prepared in accordance with step (d) Example 2 from 2-ethoxycarbonylmethyl-1-(3-methoxyphenyl)-5-(4-trifluoromethylphenoxy)indole-3-carboxylic acid ethyl ester (125 mg, 0.23 mmol, see step (c) Example 5). Yield 80 mg (53%), mp 237-239° C.

200 MHz $^1$H-NMR (DMSO-$d_6$), δ: 3.81 (s, 3H); 3.90-4.03 (m, 2H); 5.76 (s, 1H); 6.96-7.24 (m, 7H); 7.56 (t, J=8.2 Hz; 1H); 7.70 (d, J=8.2 Hz, 2H); 7.78 (d, J=2.0 Hz, 1H); 12.3-13.0 (br s, 1H).

Example 6

1-(Benzo[1,3]dioxol-5-yl)-2-carboxymethyl-5-(4-trifluoromethylphenoxy)indole-3-carboxylic acid (a) 3-(Benzo[1,3]dioxol-5-ylamino)pent-2-enedioic acid diethyl ester The sub-title compound was prepared in accordance with step (a) Example 1 from benzo[1,3]dioxol-5-ylamine.

(b) 1-Benzo[31]dioxol-5-yl-2-ethoxycarbonylmethyl-5-hydroxyindole-3-carboxylic acid ethyl ester The sub-title compound was prepared in accordance with step (b) Example 1 from 3-(benzo[1,3]dioxol-5-ylamino)pent-2-enedioic acid diethyl ester (30 mmol, see step (a) Example 6). Yield 2.36 g (19%).

(c) 1-(Benzo[1,3]dioxol-5-yl)-2-ethoxycarbonylmethyl-5-(4-trifluoromethylphenoxy)indole-3-carboxylic acid ethyl ester The sub-title compound was prepared in accordance with step (c) Example 1 from 1-(benzo[1,3]dioxol-5-yl)-2-ethoxycarbonylmethyl-5-hydroxyindole-3-carboxylic acid ethyl ester (189 mg, 0.46 mmol, see step (b) Example 6) and 4-trifluoromethylphenylboronic acid (129 mg, 0.68 mmol). Yield 175 mg, 68%.

(d) 1-(Benzo[1,3]dioxol-5-yl)-2-carboxymethyl-5-(4-trifluoromethylphenoxy)indole-3-carboxylic acid The title compound was prepared in accordance with step (d) Example 2 from 1-(benzo[1,3]dioxol-5-yl)-2-ethoxycarbonylmethyl-5-(4-trifluoromethylphenoxy)indole-3-carboxylic acid ethyl ester (170 mg, 0.3 mmol, see step (c) Example 6). Yield 132 mg (88%).

200 MHz $^1$H-NMR (DMSO-$d_6$), δ: 4.00 (s, 2H); 6.19 (s, 2H); 6.92 (dd, J=8.2 and 1.9 Hz, 1H); 6.97-7.06 (m, 2H); 706-7.19 (m, 4H); 7.64-7.74 (m, 2H); 7.76 (d, J=2.0 Hz, 1H); 12.40-12.6 (br s, 2H).

Example 7

2-Carboxymethyl-1-(4-carboxymethylphenyl)-5-(4-trifluoromethylphenoxy)indole-3-carboxylic acid (a) 3-(4-Ethoxycarbonylmethylphenylamino)pent-2-enedioic acid diethyl ester The sub-title compound was prepared in accordance with step (a) Example 1 from ethyl-4-aminophenylacetate (3.00 g, 16.7 mmol).

(b) 2-Carboxymethyl-1-(4-carboxymethylphenyl)-5-hydroxyindole-3-carboxylic acid ethyl ester The sub-title compound was prepared in accordance with step (b) Example 1 from 3-(4-ethoxycarbonylmethylphenylamino)pent-2-enedioic acid diethyl ester (16.7 mmol, see step (a) Example 7). Yield 540 mg (5.4%).

(c) 2-Carboxymethyl-1-(4-carboxymethylphenyl)-5-(4-trifluoromethylphenoxy)indole-3-carboxylic acid ethyl ester The sub-title compound was prepared in accordance with step (c) Example 1 from 2-carboxymethyl-1-(4-carboxymethyl-phenyl)-5-hydroxyindole-3-carboxylic acid ethyl ester (235 mg, 0.5 mmol, see step (b) Example 7) and 4-trifluoromethylphenylboronic acid (143 mg, 0.75 mmol). Yield 122 mg, 41%.

(d) 2-Carboxymethyl-1-(4-carboxymethylphenyl)-5-(4-trifluoromethylphenoxy)indole-3-carboxylic acid The title compound was prepared in accordance with step (d) Example 1 from 2-carboxymethyl-1-(4-carboxymethylphenyl)-5-(4-trifluoromethylphenoxy)indole-3-carboxylic acid ethyl ester (120 mg, 0.2 mmol, see step (c) Example 7). Yield 105 mg (98%).

200 MHz $^1$H-NMR (DMSO-$d_6$), δ: 3.75 (s, 2H); 4.00 (s, 2H); 6.88-7.27 (m, 4H); 7.29-7.88 (m, 7H); 12.2-12.9 (br s, 3H).

Example 8

2-Carboxymethyl-1-(3-chlorophenyl)-5-(4-trifluoromethylphenoxy )indole-3-carboxylic acid (a) 3-(3-Chlorophenylamino)pent-2-enedioic acid diethyl ester The sub-title compound was prepared in accordance with step (a) Example 1 from 3-chloroaniline.

(b) 1-(3-Chlorophenyl)-2-ethoxycarbonylmethyl-5-hydroxyindole-3-carboxylic acid ethyl ester The sub-title compound was prepared in accordance with step (b) Example 1 from 3-(3-chlorophenylamino)pent-2-enedioic acid diethyl ester (30 mmol, see step (a) Example 8). Yield 425 mg (3.5%).

(c) 1-(3-Chlorophenyl)-2-ethoxycarbonylmethyl-5-(4-trifluoromethylphenoxy)indole-3-carboxylic acid ethyl ester The sub-title compound was prepared in accordance with step (c) Example 1 from 1-(3-chlorophenyl)-2-ethoxycarbonylmethyl-5-hydroxyindole-3-carboxylic acid ethyl ester (141 mg, 0.35 mmol, see step (b) Example 8) and 4-trifluoromethylphenylboronic acid (100 mg, 0.53 mmol). Yield 120 mg (63%).

(d) 2-Carboxymethyl-1-(3-chlorophenyl)-5-(4-trifluoromethylphenoxy)indole-3-carboxylic acid The title compound was prepared in accordance with step (d) Example 1 from 1-(3-chlorophenyl)-2-ethoxycarbonylmethyl-5-(4-trifluoromethylphenoxy)indole-3-carboxylic acid ethyl ester (115 mg, 0.21 mmol, see step (c) Example 8). Yield 78 mg (68%), mp 236-238° C.

200 MHz $^1$H-NMR (DMSO-$d_6$), δ: 4.02 (s, 2H); 7.03 (dd, J=8.8, 2.1 Hz, 1H); 7.07-7.18 (m, 3H); 7.43-7.54 (m, 1H); 7.59-7.74 (m, 5H); 7.78 (d, J=2.1 Hz, 1H); 12.2-13.0 (br s, 2H).

Example 9

9-Carboxymethyl-1-(4-trifluoromethoxyphenyl)-5-(4-trifluoromethylphenoxy)indole-3-carboxylic acid (a) 3-(4-Trifluoromethoxyphenylamino)pent-2-enedioic acid diethyl ester The sub-title compound was prepared in accordance with step (a) Example 1 from 4-trifluoromethoxyaniline.

(b) 2-Ethoxycarbonylmethyl-5-hydroxy-1-(4-trifluoromethoxyphenyl)indole-3-carboxylic acid ethyl ester The sub-title compound was prepared in accordance with step (b) Example 1 from 3-(4-trifluoromethoxyphenylamino)pent-2-enedioic acid diethyl ester (8.90 g, 24.6 mmol. Yield 3.1 g (31%).

(c) 2-Ethoxycarbonylmethyl-1-(4-trifluoromethoxyphenyl)-5-(4-trifluoromethylphenoxy)indole-3-carboxylic acid ethyl ester The sub-title compound was prepared in accordance with step (c) Example 1 from 2-ethoxycarbonylmethyl-5-hydroxy-1-(4-trifluoromethoxyphenyl)indole-3-carboxylic acid ethyl ester (158 mg, 0.35 mmol, see step (b) Example 9) and 4-trifluoromethylphenylboronic acid. Yield 135 mg (65%).

(d) 2-Carboxymethyl-1-(4-trifluoromethoxyphenyl)-5-(4-trifluoromethylphenoxy)indole-3-carboxylic acid The title compound was prepared in accordance with step (d) Example 2 from 2-ethoxycarbonylmethyl-1-(4-trifluoromethoxyphenyl)-5-(4-trifluoromethylphenoxy)indole-3-carboxylic acid ethyl ester (130 mg, 0.22 mmol, see step (c) Example 9). Yield 85 mg (60%) mp 257-259° C.

200 MHz $^1$H-NMR (DMSO-$d_6$), δ: 4.04 (s, 2H); 7.03 (dd, J=8.9 and 2.1 Hz, 1H); 7.07-7.17 (m, 3H); 7.53-7.75 (m, 6H); 7.79 (d, J=2.1 Hz; 1H); 12.4-12.75 (br s, 2H).

Example 10

2-Carboxymethyl-1-(4-isopropylphenyl)-5-(4-trifluoromethylphenoxy)indole-3-carboxylic acid (a) 3-(4-Isopropylphenylamino)pent-2-enedioic acid diethyl ester The sub-title compound was prepared in accordance with step (a) Example 1 from cumidine.

(b) 2-Ethoxycarbonylmethyl-1-(4-isopropylphenyl)-5-hydroxyindole-3-carboxylic acid ethyl ester The sub-title compound was prepared in accordance with step (b) Example 1 from 3-(4-isopropylphenylamino)pent-2-enedioic acid diethyl ester (30 mmol, see step (a) Example 10). Yield 3.6 g (29%).

(c) 2-Ethoxycarbonylmethyl-1-(4-isopropylphenyl)-5-(4-trifluoromethylphenoxy)indole-3-carboxylic acid ethyl ester The sub-title compound was prepared in accordance with step (c) Example 1 from 2-ethoxycarbonylmethyl-1-(4-isopropylphenyl)-5-hydroxyindole-3-carboxylic acid ethyl ester (143 mg, 0.35 mmol, see step (b) Example 10) and 4-trifluoromethylphenylboronic acid (100 mg, 0.53 mmol). Yield 110 mg (57%).

(d) 2-Carboxymethyl-1-(4-isopropylphenyl)-5-(4-trifluoromethylphenoxy)indole-3-carboxylic acid The title compound was prepared in accordance with step (d) Example 2 from 2-ethoxycarbonylmethyl-1-(4-isopropylphenyl)-5-(4-trifluoromethylphenoxy)indole-3-carboxylic acid ethyl ester (110 mg, 0.19 mmol, see step (c) Example 10. Yield 78 mg (82%), mp 250-252° C.

200 MHz $^1$H-NMR (DMSO-$d_6$), δ: 1.29 (d, J=7.0 Hz, 6H); 3.04 (heptet, J=7.0 Hz, 1H); 3.97 (s, 2H); 7.00 (dd, J=8.9 and 2.0 Hz, 1H); 7.04-7.17 (m, 3H); 7.32-7.43 (m, 2H); 7.47-7.59 (m, 2H); 7.64-7.75 (m, 2H); 7.78 (d, J=2.0 Hz; 1H); 12.3-12.7 (br s, 2H).

Example 11

2-Carboxymethyl-1-(2-methoxyphenyl-5-(4-trifluoromethylphenoxy)indole-3-carboxylic acid (a) 3-(2-Methoxyphenylamino)pent-2-enedioic acid diethyl ester The sub-title compound was prepared in accordance with step (a) Example 1 from o-anisidine.

(b) 2-Ethoxycarbonylmethyl-1-(2-methoxyphenyl)-5-hydroxyindole-3-carboxylic acid ethyl ester The sub-title compound was prepared in accordance with step (b) Example 1 from 3-(2-methoxyphenylamino)pent-2-enedioic acid diethyl ester (30 mmol, see step (a) Example 11). Yield 1.4 g (12%).

(c) 2-Ethoxycarbonylmethyl-1-(2-methoxyphenyl)-5-(4-trifluoromethylphenoxy)indole-3-carboxylic acid ethyl ester The sub-title compound was prepared in accordance with step (c) Example 1 from 2-ethoxycarbonylmethyl-1-(2-methoxyphenyl)-5-hydroxyindole-3-carboxylic acid ethyl ester (139 mg, 0.35 mmol, see step (b) Example 11) and 4-trifluoromethylphenylboronic acid (100 mg, 0.53 mmol). Yield 120 mg (63%).

(d) 9-Carboxymethyl-1-(2-methoxyphenyl-5-(4-trifluoromethylphenoxy )indole-3-carboxylic acid The title compound was prepared in accordance with step (d) Example 2 from 2-ethoxycarbonylmethyl-1-(2-methoxyphenyl)-5-(4-trifluoromethylphenoxy)indole-3-carboxylic acid ethyl ester (82 mg, 0.23 mmol, see step (c) Example 11). Yield 82 mg (77%), mp 237-239° C.

200 MHz $^1$H-NMR (DMSO-$d_6$), δ: 3.55 (d, J=17.2 Hz, 1H); 3.73 (s, 3H); 4.21 (d, J=17.2 Hz; 1H); 6.92 (d, J=8.8 Hz, 1H); 6.99 (dd, J=8.8 Hz, 2.1 Hz, 1H); 7.07-7.16 (m, 2H); 7.20 (dd, J=7.4 Hz, 1H); 7.30-7.40 (m, 2H); 7.56-7.74 (m, 3H); 7.76 (d, J=1.8 Hz, 1H) 12.3-12.7 (br s, 2H).

Example 12

2-Carboxymethyl-1-(4-isopropoxyphenyl)-5-(4-trifluoromethylphenoxy)indole-3-carboxylic acid ethyl ester (a) 3-(4-Isopropoxyphenylamino)pent-2-enedioic acid diethyl ester The sub-title compound was prepared in accordance with step (a) Example 1 from 4-isopropoxyaniline.

(b) 2-Ethoxycarbonylmethyl-5-hydroxy-1-(4-isopropoxyphenyl)indole-3-carboxylic acid ethyl ester The sub-title compound was prepared in accordance with step (b) Example 1 from 3-(4-isopropoxyphenylamino)pent-2-enedioic acid diethyl ester (30 mmol, see step (a) Example 12). Yield 3.8 g (33%).

(c) 2-Ethoxycarbonylmethyl-1-(4-isopropoxyphenyl)-5-(4-trifluoromethylphenoxy)indole-3-carboxylic acid ethyl ester The sub-title compound was prepared in accordance with step (c) Example 1 from 2-ethoxycarbonylmethyl-5-hydroxy-1-(4-isopropoxyphenyl)indole-3-carboxylic acid ethyl ester (250 mg, 0.59 mmol and 4-trifluoromethylphenylboronic acid (167 mg, 0.88 mmol) and was used in the subsequent step without purification.

(d) 2-Carboxymethyl-1-(4-isopropoxyphenyl)-5-(4-trifluoromethylphenoxy)indole-3-carboxylic acid ethyl ester The title compound was prepared in accordance with step (d) Example 2 from 2-ethoxycarbonylmethyl-1-(4-isopropoxyphenyl)-5-(4-trifluoromethylphenoxy)indole-3-carboxylic acid ethyl ester (265 mg, 0.47 mmol; see step (c) above), NaOH (aq, 2 M, 2.5 mL) and EtOH (15 mL). Yield 176 mg (70%), mp 158° C.

200 MHz $^1$H NMR spectrum: (DMSO-$d_6$), δ: 1.40 (t, J=7.1 Hz, 3H); 1.41 (d, J=6.0 Hz, 6H); 3.98 (s, 2H); 4.46 (q, J=7.1 Hz, 21); 4.64 (heptet, J=6.0 Hz, 1H); 6.90-7.11 (m, 6H); 7.24-7.32 (m, 2H); 7.51-7.61 (m, 2H); 7.77 (dd, J=2.1 Hz, 1H); 10.5-11.4 (br s, 1H).

Example 13

2-Carboxymethyl-1-(5-methoxypyridin-2-yl)-5-(4-trifluoromethylphenoxy)indole-3-carboxylic acid (a) 3-(5-Methoxypyridin-2-ylamino)pent-2-enedioic acid diethyl ester The sub-title compound was prepared in accordance with step (a) Example 1 from 5-methoxypyridin-2-ylamine.

(b) 2-Ethoxycarbonylmethyl-5-hydroxy-1-(5-methoxypyridin-2-yl)indole-3-carboxylic acid ethyl ester The sub-title compound was prepared in accordance with step (b) Example 2 from 3-(5-methoxypyridin-2-ylamino)pent-2-enedioic acid diethyl ester (30 mmol, see step (a) Example 13). Yield 560 mg (5%).

(c) 2-Ethoxycarbonylmethyl-1-(5-methoxypyridin-2-yl)-5-(4-trifluoromethylphenoxy)indole-3-carboxylic acid ethyl ester The sub-title compound was prepared in accordance with step (c) Example 1 from 2-ethoxycarbonylmethyl-5-hydroxy-1-(5-methoxypyridin-2-yl)indole-3-carboxylic acid ethyl ester (139 mg, 0.35 mmol, see step (b) Example 13) and 4-trifluoromethylphenylboronic acid (100 mg, 0.53 mmol). Yield 110 mg (58%).

(d) 2-Carboxymethyl-1-(5-methoxypyridin-2-3 μl)-5-(4-trifluoromethylphenoxy)indole-3-carboxylic acid The title compound was prepared in accordance with step (d) Example 2 from 2-ethoxycarbonylmethyl-1-(5-methoxypyridin-2-yl)-5-(4-trifluoromethylphenoxy)indole-3-carboxylic acid ethyl ester (100 mg, 0.18 mmol, see step (c) Example 13). Yield 72 mg (82%), mp 237-239° C.

200 MHz $^1$H-NMR (DMSO-$d_6$), δ: 3.96 (s, 3H); 4.04 (s, 2H); 7.02 (dd, J=8.9, 2.1 Hz, 1H); 7.06-7.17 (m, 4H); 7.65-7.75 (m, 2H); 7.78 (d, J=2.1 Hz; 1H); 7.82 (dd, J=8.9, 2.6 Hz, 1H); 8.29 (d, J=2.6 Hz, 1H); 12.3-12.8 (br s, 2H).

Example 14

2-Carboxymethyl-1-(−9-ethylcarbazol-3-yl)-5-(4-trifluoromethylphenoxy)indole-3-carboxylic acid (a) 3-(9-Ethylcarbazol-3-ylamino)pent-2-enedioic acid diethyl ester The sub-title compound was prepared in accordance with step (a) Example 1 from 3-amino-9-ethylcarbazole.

(b) 2-Ethoxycarbonylmethyl-1-(9-ethylcarbazol-3-yl)-5-hydroxyindole-3-carboxylic acid ethyl ester The sub-title compound was prepared in accordance with step (b) Example 1 from 3-(9-ethylcarbazol-3-ylamino)pent-2-enedioic acid diethyl ester. Yield 1.52 g (16%).

(c) 2-Ethoxycarbonylmethyl-1-(9-ethylcarbazol-3-yl)-5-(4-trifluoromethylphenoxy)indole-3-carboxylic acid ethyl ester The sub-title compound was prepared in accordance with step (c) Example 1 from 2-ethoxycarbonylmethyl-1-(9-ethylcarbazol-3-yl)-5-hydroxyindole-3-carboxylic acid ethyl ester (170 mg, 0.35 mmol, see step (b) Example 14) and 4-trifluoromethylphenylboronic acid (100 mg, 0.53 mmol. Yield 130 mg (60%).

(d) 2-Carboxymethyl-1-(9-ethylcarbazol-3-yl)-5-(4-trifluoromethylphenoxy)indole-3-carboxylic acid The title compound was prepared in accordance with step (d) Example 2 from 2-ethoxycarbonylmethyl-1-(9-ethylcarbazol-3-yl)-5-(4-trifluoromethylphenoxy)indole-3-carboxylic acid ethyl ester (130 mg, 0.21 mmol, see step (c) Example 14). Yield 82 mg (68%, mp 243-245° C.

200 MHz $^1$H-NMR (DMSO-$d_6$), δ: 1.40 (t, J=6.8 Hz, 3H); 3.89-4.15 (m, 2H); 4.46-4.64 (m, 2H); 6.98 (dd, J=8.9, 2.1 Hz, 1H); 7.04-7.18 (m, 3H); 7.19-7.34 (m, 1H); 7.39-7.61 (m, 2H); 7.63-7.77 (m, 3H); 7.78-7.99 (m, 2H); 8.20 (d, J=7.6 Hz, 1H); 8.30 (d, J=1.8 Hz, 1H); 1.3-13.0 (br s, 2H).

Example 15

2-Carboxymethyl-1-(4-morpholin-4-yl-phenyl)-5-(4-trifluoromethylphenoxy)indole-3-carboxylic acid (a) 3-(4-Morpholin-4-yl-phenylamino)pent-2-ene-dioic acid diethyl ester The sub-title compound was prepared in accordance with step (a) Example 1 from 4-morpholinoaniline.

(b) 2-Ethoxycarbonylmethyl-5-hydroxy-1-(4-morpholin-4-yl-phenyl)indole-3-carboxylic acid ethyl ester The sub-title compound was prepared in accordance with step (b) Example 1 from 3-(4-morpholin-4-yl-phenylamino)pent-2-enedioic acid diethyl ester (7.24 g, 20 mmol, see step (a) Example 15). Yield 4.50 g (50%).

(c) 2-Ethoxycarbonylmethyl-1-(4-morpholin-4-ylphenyl)-5-(4-trifluoromethylphenoxy)indole-3-carboxylic acid ethyl ester The sub-title compound was prepared in accordance with step (c) Example 1 from 2-ethoxycarbonylmethyl-5-hydroxy-1-(4-morpholin-4-yl-phenyl)indole-3-carboxylic acid ethyl ester (158 mg, 0.35 mmol, see step (b) Example 15) and 4-trifluoromethylphenylboronic acid (100 mg, 0.53 mmol). Yield 120 mg (57%).

(d) 2-Carboxymethyl-1-(4-morpholin-4-ylphenyl)-5-(4-trifluoromethylphenoxy)indole-3-carboxylic acid The title compound was prepared in accordance with step (d) Example 2 from 2-ethoxycarbonylmethyl-1-(4-morpholin-4-yl-phenyl)-5-(4-trifluoromethylphenoxy)indole-3-carboxylic acid ethyl ester (120 mg, 0.2 mmol, see step (c) Example 15). Yield 72 mg (67%), mp 257-259° C.

200 MHz $^1$H-NMR (DMSO-$d_6$), δ: 3.18-3.30 (m, 4H); 3.71-3.84 (m, 4H); 3.97 (s, 2H); 6.99 (dd, J=8.9, 2.1 Hz, 1H); 7.03-7.21 (m, 5H); 7.22-7.34 (m, 2H); 7.65-7.74 (m, 2H); 7.76 (d, J=1.9 Hz, 1H); 12.3-12.6 (br s, 2H).

Example 16

2-Carboxymethyl-1-(4-dimethylaminophenyl)-5-(4-trifluoromethylphenoxy)indole-3-carboxylic acid (a) 3-(4-Dimethylaminophenyl)pent-2-enedioic acid diethyl ester The sub-title compound was prepared in accordance with step (a) Example 1 from N,N-dimethyl-1,4-phenylenediamine.

(b) 1-(4-Dimethylaminophenyl)-2-ethoxycarbonylmethyl-5-hydroxyindole-3-carboxylic acid ethyl ester The sub-title compound was prepared in accordance with step (b) Example 1 from 3-(4-dimethylaminophenyl)pent-2-enedioic acid diethyl ester (30 mmol, see step (a) Example 16. Yield 1.21 g (9.4%).

(c) 1-(4-Dimethylaminophenyl)-2-ethoxycarbonylmethyl-5-(4-trifluoromethylphenoxy)indole-3-carboxylic acid ethyl ester The sub-title compound was prepared in accordance with step (c) Example 1 from 1-(4-dimethylaminophenyl)-2-ethoxycarbonylmethyl-5-hydroxyindole-3-carboxylic acid ethyl ester (144 mg, 0.35 mmol, see step (b) Example 16) and 4-trifluoromethylphenylboronic acid (100 mg, 0.53 mmol). Yield 70 mg (35%).

(d) 2-Carboxymethyl-1-(4-dimethylaminophenyl)-5-(4-trifluoromethylphenoxy)indole-3-carboxylic acid The title compound was prepared in accordance with step (d) Example 2 from 1-(4-dimethylaminophenyl)-2-ethoxycarbonylmethyl-5-(4-trifluoromethylphenoxy)indole-3-carboxylic acid ethyl ester (70 mg, 0.13 mmol, see step (c) Example 16). Yield 42 mg (65%), mp 235-237° C.

200 MHz $^1$H-NMR (DMSO-$d_6$), δ: 3.01 (s, 6H); 3.95 (s, 2H), 6.82-6.94 (m, 2H); 6.98 (dd, J=8.8 Hz, 1H); 7.02-7.15 (m, 3H); 7.16-7.26 (m, 2H); 7.65-7.73 (m, 2H); 7.76 (d, 1H); 12.3-12.6 (br s, 2H).

Example 17

2-Carboxymethyl-1-(4-piperidin-4-ylphenyl)-5-(4-trifluoromethylphenoxy)indole-3-carboxylic acid (a) 3-(4-Piperidin-4-ylphenylamino)pent-2-enedioic acid diethyl ester The sub-title compound was prepared in accordance with step (a) Example 1 from 4-piperidinoaniline.

(b) 2-Ethoxycarbonylmethyl-5-hydroxy-1-(4-piperidin-4-ylphenyl)indole-3-carboxylic acid ethyl ester The sub-title compound was prepared in accordance with step (b) Example 1 from 3-(4-piperidin-4-yl-phenylamino)pent-2-enedioic acid diethyl ester (28.4 mmol, see step (a) Example 17). Yield 2.43 g (15%).

(c) 2-Ethoxycarbonylmethyl-1-(4-piperidin-4-ylphenyl)-5-(4-trifluoromethylphenoxy)indole-3-carboxylic acid ethyl ester The sub-title compound was prepared in accordance with step (c) Example 1 from 2-ethoxycarbonylmethyl-5-hydroxy-1-(4-piperidin-4-ylphenyl)indole-3-carboxylic acid ethyl ester (203 mg, 0.45 mmol, see step (b) Example 17) and 4-trifluoromethylphenylboronic acid. Yield 160 mg (60%).

(d) 2-Carboxymethyl-1-(4-piperidin-4-ylphenyl)-5-(4-trifluoromethylphenoxy)indole-3-carboxylic acid The title compound was prepared in accordance with step (d) Example 2 from 2-ethoxycarbonylmethyl-1-(4-piperidin-4-ylphenyl)-5-(4-trifluoromethylphenoxy)indole-3-carboxylic acid ethyl ester (160 mg, 0.27 mmol, see step (c) Example 17). Yield 82 mg (56%), mp 256-258° C.

200 MHz $^1$H-NMR (DMSO-$d_6$), δ: 1.50-1.74 (m, 6H); 3.18-3.38 (m, 4H, overlapped with DMSO); 3.96 (s, 2H); 6.99 (dd, J=8.9 and 2.1 Hz, 1H); 7.03-7.17 (m, 5H); 7.18-7.28 (m, 2H); 7.65-7.74 (m, 2H); 7.76 (d, J=1.9 Hz, 1H); 12.3-12.7 (br s, 2H).

Example 18

2-Carboxymethyl-5-(7-chloroquinolin-4-yloxy)-1-(4-trifluoromethoxyphenyl)indole-3-carboxylic acid

(a) 5-(7-Chloroquinolin-4-yloxy)-2-ethoxycarbonylmethyl-1-(4-trifluoromethoxy phenyl)indole-3-carboxylic acid ethyl ester A mixture of 2-ethoxycarbonylmethyl-5-hydroxy-1-(4-trifluoromethoxyphenyl)indole-3-carboxylic acid ethyl ester (100 mg, 0.22 mmol; see step (b) Example 9), 4,7-dichloroquinoline (66 mg, 0.33 mmol), $K_2CO_3$ (60 mg, 0.43 mmol) and DMF (2 mL) was stirred at 100-110° C. for 3 h, cooled, diluted with $H_2O$ (20 mL) and extracted with $Et_2O$ (30 mL). The extract was washed with $H_2O$, dried ($Na_2SO_4$, concentrated and purified by chromatography to give the title compound. Yield 48 mg (36%).

(b) 2-Carboxymethyl-5-(7-chloroquinolin-4-yloxy)-1-(4-trifluoromethoxyphenyl)indole-3-carboxylic acid A mixture of 5-(7-chloroquinolin-4-yloxy)-2-ethoxycarbonylmethyl-1-(4-trifluoromethoxyphenyl)indole-3-carboxylic acid ethyl ester (40 mg, 0.065 mmol, see step (a) above), NaOH (50 mg), water (1 mL) and EtOH (1 mL) was heated at reflux for 1 h. The EtOH was removed in vacuo and the mixture was acidified with HCl (aq, 1 M) to pH 4. The solid was filtered off to give the title compound. Yield 33 mg (91%).

200 MHz $^1$H-NMR (DMSO-$d_6$), δ: 4.08 (s, 2H); 6.77 (d, J=5.8 Hz, 1H); 7.21 (s, 2H); 7.59-7.75 (m, 4H); 7.83 (dd, J=1.7 Hz, 9.0 Hz, 1H); 7.98 (s, 1H); 8.22 (d, J=1.7 Hz, 1H); 8.53 (d, J=9.0 Hz, 1H); 8.82 (d, J=5.8 Hz, 1H); 11.5-14.0 (br s, 2H).

Example 19

1-(4-Isopropoxyphenyl)-5-(5-trifluoromethylpyridin-2-yloxy)indole-2,3-dicarboxylic acid

(a) 5-Hydroxy-1-(4-isopropoxyphenyl)-indole-2,3-dicarboxylic acid dimethyl ester The sub-title compound was prepared from N-(4-isopropoxyphenyl)aminofumaric acid dimethyl ester (1.57 g, 5.40 mmol), p-benzoquinone (0.60 g, 5.6 mmol) and $BF_3$ etherate (0.83 m L, 5.8 mmol), see procedure in GDR No. 61800 (1967). Yield 1.40 g (71%).

(b) 1-(4-Isopropoxyphenyl)-5-(5-trifluoromethylpyridin-2-yloxy)indole-2,3-dicarboxylic acid dimethyl ester The sub-title compound was prepared in accordance with step (a) Example 18 from 5-hydroxyindole-1-(4-isopropoxyphenyl)-2,3-dicarboxylic acid dimethyl ester (104 mg, 0.27 mmol, see (a) above) and 2-chloro-5-trifluoromethylpyridine (74 mg, 0.41 mmol). Yield 100 mg (70%).

(c) 1-(4-Isopropoxyphenyl)-5-(5-trifluoromethylpyridin-2-yloxy)-indole-2,3-dicarboxylic acid The sub-title compound was prepared in accordance with step (b) Example 18 from 1-(4-isopropoxyphenyl)-5-(5-trifluoromethylpyridin-2-yloxy)indole-2,3-dicarboxylic acid dimethyl ester (90 mg, 0.17 mmol), see step (a) Example 19). Yield 50 mg (59%).

200 MHz $^1$H-NMR (DMSO-$d_6$), δ: 1.32 (d, J=5.9 Hz, 6H); 3.0-5.0 (br s, 2H); 4.70 (heptet. J=5.9 Hz, 1H); 7.02-7.17 (m, 4H); 7.24 (d, J=8.8 Hz, 1H); 7.30-7.40 (m, 2H); 7.92 (s, 1H); 8.22 (dd, J=2.4, 8.8 Hz, 1H); 8.54 (s 1H).

Example 20

1-(4-Isopropoxyphenyl)-5-(3-carbamoylpyridin-2-yloxy)indole-2,3-dicarboxylic acid

(a) 5-(3-Carbamoylpyridin-2-yloxy)-1-(4-isopropoxyphenyl)indole-2,3-dicarboxylic acid dimethyl ester The sub-title compound was prepared in accordance with step (a) Example 18 from 5-hydroxy-1-(4-isopropoxyphenyl)-indole-2,3-dicarboxylic acid dimethyl ester (100 mg, 0.26 mmol, see (a) Example 19) and 2-chloro-3-carbamoylpyridine (100 mg, 0.63 mmol). Yield 70 mg (54%).

(b) 5-(3-Carbamoylpyridin-2-yloxy)-1-(4-isopropoxyphenyl)indole-2,3-dicarboxylic acid The title compound was prepared in accordance with step (b) Example 18 from 5-(3-carbamoylpyridin-2-yloxy)-1-(4-isopropoxyphenyl)indole-2,3-dicarboxylic acid dimethyl ester (70 mg, 0.14 mmol, see step (a) above). Yield 49 mg (74%), mp 236-238° C.

200 MHz $^1$H-NMR (DMSO-$d_6$), δ: 1.32 (d, J=6.0 Hz, 6H); 3.0-4.5 (br s, 2H); 4.71 (m, 1H); 7.05-7.15 (m, 4H); 7.19 (dd, J=7.2, 5.1 Hz, 1H); 7.32-7.44 (m, 2H); 7.78 (d, 1H); 7.89 (br s, 2H); 8.11-8.14 (m, 1H); 8.16 (dd, J=5.2, 1.8 Hz, 1H).

Example 21

2-Carboxymethyl-5-(5-chloromethylpyridin-2-yloxy)-1-(4-trifluoromethoxyphenyl)indole-3-carboxylic acid ethyl ester a) 5-(5-Chloromethylpyridin-2-yloxy)-2-ethoxycarbonylmethyl-1-(4-trifluoromethoxyphenyl)indole-3-carboxylic acid ethyl ester $K_2CO_3$ (138 mg, 1.0 mmol), 2-chloro-5-chloromethylpyridine (32 mg, 0.2 mmol) and 18-crown-6 (5 mg) were added to a mixture of 2-ethoxycarbonylmethyl-5-hydroxy-1-(4-trifluoromethoxyphenyl)indole-3-carboxylic acid ethyl ester (90 mg, 0.2 mmol, see step (b) Example 9) and DMF (5 mL). The mixture was stirred for 48 h at 70° C., cooled, diluted with EtOAc, filtered through Celite®, concentrated and purified by chromatography. Yield 60 mg (520%).

b) 2-Carboxymethyl-5-(5-chloromethylpyridin-2-yloxy-1-(4-trifluoromethoxyphenyl)indole-3-carboxylic acid ethyl ester NaOH (17 mg, 0.43 mmol) in water (5 mL) was slowly added to 5-(5-chloromethylpyridin-2-yloxy)-2-ethoxycarbonylmethyl-1-(4-trifluoromethoxyphenyl)indole-3-carboxylic acid ethyl ester (50 mg, 0.086 mmol, see step (a) above) in EtOH (15 mL). The mixture was stirred at rt for 48 h, neutralized by addition of HCl (aq), concentrated and purified by preparative TLC. Yield 35 mg (74%), mp 168-170° C.
$^1$H NMR spectrum: (200 MHz, CDCl$_3$), δ: 1.46 (t, J=7.1 Hz, 3H); 3.96 (s, 2H); 4.48 (q, J=7.1 Hz, 2H); 5.15 (s, 2H); 6.86-7.00 (m, 2H); 7.36 (d, J=8.3 Hz, 1H); 7.37-7.52 (m, 5H); 7.65 (d, 1H); 7.79 (dd, J=8.3 Hz, 1H); 8.50 (s, 1H).

Example 22

2-Carboxymethyl-5-(5-chloromethylpyridin-2-yloxy)-1-(4-isopropoxyphenyl)indole-3-carboxylic acid ethyl ester a) 5-(5-Chloromethylpyridin-2-yloxy)-2-ethoxycarbonylmethyl-1-(4-isopropoxyphenyl)indole-3-carboxylic acid ethyl ester The sub-title compound was prepared in accordance with step (a) Example 21 from 2-ethoxycarbonylmethyl-5-hydroxy-1-(4-isopropoxyphenyl)indole-3-carboxylic acid ethyl ester (106 mg, 0.25 mmol, see step (b) Example 12) and 2-chloro-5-chloromethylpyridine (41 mg, 0.25 mmol). Yield 90 mg (66%).

b) 2-Carboxymethyl-5-(5-chloromethylpyridin-2-yloxy)-1-(4-isopropoxyphenyl)indole-3-carboxylic acid ethyl ester The title compound was prepared in accordance with step (b) Example 21 from 5-(5-chloromethylpyridin-2-yloxy)-2-ethoxycarbonylmethyl-1-(4-isopropoxyphenyl)indole-3-carboxylic acid ethyl ester (90 mg, 0.16 mmol, see step (a) above). Yield 61 mg (71%), mp 153-155° C.
$^1$H NR spectrum: (200 MHz, CDCl$_3$), δ: 1.40 (d, J=6.0 Hz, 6H); 1.45 (t, J=7.0 Hz, 3H); 3.96 (s, 2H); 4.46 (q, J=7.0 Hz, 2H); 4.62 (heptet, J=6.0 Hz, 1H); 5.14 (s, 2H); 6.88 (dd, J=8.9, 2.3 Hz, 1H); 6.96 (d, J=8.9 Hz, 1H); 6.92-7.07 (m, 2H); 7.20-7.30 (m, 2H, overlapped with CHCl$_3$); 7.36 (d, J=8.1 Hz, 1H); 7.65 (d, J=1.9 Hz, 1H); 7.80 (dd, J=8.1, 1.9 Hz, 1H); 8.50 (s, 1H); 9.8-11.4 (br s, 1H).

Example 23

2-Carboxylmethyl-5-(5-chloromethylpyridin-2-yloxy)-1-(4-isopropoxyphenyl)indole-3-carboxylic acid NaOH (400 mg, 10 mmol) in H$_2$O (10 mL) was slowly added to 2-carboxymethyl-5-(5-chloromethylpyridin-2-yloxy)-1-(4-isopropoxyphenyl) indole-3-carboxylic acid ethyl ester (40 mg, 0.076 mmol, see step (b) Example 22) in EtOH (10 mL). The mixture was stirred for 48 h at 50° C., neutralized with HCl (aq), concentrated and purified by chromatography. Yield 26 mg (69%), mp 167-169° C.
200 MHz $^1$H NMR spectrum (DMSO-d$_6$), δ: 1.33 (d, J=6.0 Hz, 6H); 3.89 (s, 2H); 4.71 (heptet, J=6.0 Hz, 1H); 5.19 (s, 2H); 6.88 (d, 2H); 7.06-7.17 (m, 2H); 7.23-7.34 (m, 2H); 7.55 (d, J=8.2 Hz, 1H); 7.70 (s, 1H); 7.98 (dd, J=8.3, 2.3 Hz, 1H); 8.55 (d, J=1.9 Hz, 1H); 12.2-13.8 (br s, 2H).

Example 24

2-Carboxymethyl-1-(4-trifluoromethoxyphenyl)-5-(5-trifluoromethyl-2-pyridinyloxy)indole-3-carboxylic acid (a) 2-Ethoxycarbonylmethyl-1-(4-trifluoromethoxyphenyl)-5-(5-trifluoromethyl-2-pyridinyloxy)indole-3-carboxylic acid ethyl ester The sub-title compound was prepared in accordance with step (a) Example 21 from 1-(4-trifluoromethoxyphenyl)-2-ethoxycarbonylmethyl-5-hydroxyindole-3'-carboxylic acid ethyl ester (140 mg, 0.31 mmol, see step (b) Example 9) and 2-chloro-5-(trifluoromethyl)pyridine (112 mg, 0.62 mmol). Yield 87 mg (47%).

(b) 2-Carboxymethyl-1-(4-trifluoromethoxyphenyl)-5-(5-trifluoromethyl-2-pyridinyloxy)indole-3-carboxylic acid A mixture of 1-(4-trifluoromethoxyphenyl)-2-ethoxycarbonylmethyl-5-(5-trifluoromethyl-2-pyridinyloxy)indole-3-carboxylic acid ethyl ester (80 mg, 0.13 mmol, see step (a) above), NaOH (aq, 1 M, 1.1 mL), EtOH (0.5 mL) and THF (0.5 mL) was stirred at 100° C. for 9 h, cooled, diluted with H$_2$O and acidified to pH 5 with citric acid (aq, 1 M). The precipitate was collected, washed with H$_2$O and Et$_2$O to give the title compound, 30 mg (42%), mp 203° C.
200 MHz $^1$H-NMR spectrum (DMSO-d$_6$), δ: 3.81 (s, 2H); 6.95-7.11 (m, 2H); 7.22 (d, J=9.2 Hz, 1H); 7.56-7.73 (m, 4H); 7.82 (d, J=2.1 Hz, 1H); 8.21 (dd, J=2.1 Hz and 8.7 Hz, 1H); 8.50-8.58 (m, 1H).

Example 25

2-Carboxymethyl-1-(4-isopropoxyphenyl)-5-(5-trifluoromethyl-2-pyridinyloxy)indole-3-carboxylic acid ethyl ester (a) 1-(4-Isopropoxyhenyl)-2-ethoxycarbonylmethyl-5-(5-trifluoromethyl-2-pyridinyloxy)indole-3-carboxylic acid ethyl ester The sub-title compound was prepared in accordance with step (a) Example 21 from 1-(4-isopropoxyphenyl)-2-ethoxycarbonylmethyl-5-hydroxyindole-3-carboxylic acid ethyl ester (250 mg, 0.59 mmol) and 2-chloro-5-(trifluoromethyl)pyridine (160 mg, 0.88 mmol). Yield 269 mg (80%).

(b) 2-Carboxymethyl-1-(4-isopropoxyphenyl)-5-(5-trifluoromethyl-2-pyridinyloxy)indole-3-carboxylic acid ethyl ester A mixture of 1-(4-isopropoxyphenyl)-2-ethoxycarbonylmethyl-5-(5-trifluoromethyl-2-pyridinyloxy)indole-3-carboxylic acid ethyl ester (260 mg, 0.46 mmol, see step (a) above), NaOH (aq, 1 M, 1.4 mL) and EtOH (2 mL) was stirred at 50° C. for 2.5 h, cooled, diluted with H₂O (4 mL), washed with EtOAc and acidified to pH 5 with citric acid (aq, 1 M) and extracted with EtOAc. The organic layer was washed with brine, dried (Na₂SO₄), concentrated and purified by chromatography. Yield 144 mg (58%).

200 MHz ¹H-NMR spectrum (CDCl₃), δ: 1.40 (d, J=6.0 Hz, 6H); 1.42 (t, J=7.1 Hz, 3H); 3.99 (s, 2H); 4.45 (q, J=7.1 Hz, 2H); 4.63 (heptet, J=6.1 Hz, 1H); 6.94-7.13 (m, 5H); 7.20-7.32 (m, 2H); 7.83-7.93 (m, 2H); 8.44 (s, 1H).

Example 26

2-Carboxymethyl-1-(4-isopropoxyphenyl)-5-(5-trifluoromethyl-2-pyridinyloxy)indole-3-carboxylic acid The title compound was prepared by heating 2-carboxymethyl-1-(4-isopropoxyphenyl)-5-(5-trifluoromethyl-2-pyridinyloxy)indole-3-carboxylic acid ethyl ester (140 mg, 0.26 mmol, see step (b) Example 25), NaOH (aq. 2 M, 0.6 mL) and EtOH (1 mL) at 90° C. for 7 h. Yield 124 mg (92%), nip 202° C.

200 MHz ¹H-NMR spectrum (DMSO-d₆), δ: 1.33 (d, J=5.9 Hz, 6H); 3.98 (s, 2H); 4.73 (heptet, J=5.9 Hz, 1H); 7.02 (s, 2H); 7.10-7.19 (m, 2H); 7.22 (d, J=8.9 Hz, 1H); 7.29-7.40 (m, 2H); 7.79 (s, 1H); 8.20 (dd, J=8.8 Hz and 2.0 Hz, 1H); 8.53 (s, 1H); 12.50 (s, 2H).

Example 27

2-Ethoxycarbonylmethyl-1-(4-isopropoxyphenyl)-5-(5-trifluoromethyl-2-pyridinyloxy)indole-3-carboxylic acid A mixture of 2-carboxymethyl-1-(4-isopropoxyphenyl)-5-(5-trifluoromethyl-2-pyridinyloxy)indole-3-carboxylic acid (85 mg, 0.16 mmol, see Example 26), EtOH (0.8 mL) and HCl (1 M in EtOH, 0.1 mL) was heated at reflux for 20 min, concentrated, diluted with water, neutralized with NaHCO₃ (aq, sat) and extracted with EtOAc. The organic layer was washed with brine, dried (Na₂SO₄), concentrated and purified by chromatography to give the title compound. Yield 45 mg (52%), mp 202° C.

200 MHz ¹H-NMR spectrum (DMSO-d₆), δ: 1.19 (t, J=7.1 Hz, 3H); 1.40 (d, J=6.1 Hz, 6H); 4.07 (s, 2H); 4.11 (q, J=7.1 Hz, 2H); 4.62 (heptet, J=6.1 Hz, 1H); 6.94-7.12 (m, 5H); 7.21-7.32 (m, 2H); 7.88 (dd, J=8.8 Hz and 2.4 Hz, 1H); 8.01 (d, J=2.0 Hz, 1H); 8.45 (d, 1H).

Example 28

2-Carboxymethyl-5-(3-cyano-6-methyl-2-pyridinyloxy) 1-(4-isopropoxyphenyl)indole-3-carboxylic acid ethyl ester (a) 2-Ethoxycarbonylmethyl-5-(3-cyano-6-methyl-2-pyridinyloxy)-1-(4-isopropoxyphenyl)indole-3-carboxylic acid ethyl ester The sub-title compound was prepared in accordance with step (a) Example 24 from 2-ethoxycarbonylmethyl-5-hydroxy-1-(4-isopropoxyphenyl)-indole-3-carboxylic acid ethyl ester (250 mg, 0.59 mmol, see (b) Example 12) and 2-chloro-6-methylnicotinonitrile (135 mg, 0.88 mmol). Yield 280 mg (88%).

(b) 2)-Carboxymethyl-5-(3-cyano-6-methyl-2-pyridinyloxy)-1-(4-isopropoxyphenyl)indole-3-carboxylic acid ethyl ester 2-Ethoxycarbonylmethyl-5-(3-cyano-6-methyl-2-pyridinyloxy)-1-(4-isopropoxyphenyl)-indole-3-carboxylic acid ethyl ester (275 mg, 0.51 mmol, see step (a) above), 1 M NaOH (aq, 1 M, 1.52 mL) and EtOH (3 mL) was heated at 50° C. for 1 h. The title compound was isolated as described before. Yield 203 mg (77%), mp 179° C.

200 MHz ¹H-NMR spectrum (DMSO-d₆), δ: 1.31 (t, J=7.2 Hz, 3H); 1.33 (d, J=6.0 Hz, 6H); 2.31 (s, 3H); 3.95 (s, 2H); 4.30 (q, J=7.2 Hz, 2H); 4.73 (heptet, J=6.0 Hz, 1H); 7.04 (d, 2H); 7.10-7.20 (m, 3H); 7.30-7.40 (m, 2H); 7.82 (t, 1H); 8.27 (d, J=7.8 Hz, 1H); 12.2-13.2 (br s, 1H).

Example 29

2-Carboxymethyl-5-(3-carboxy-6-methyl-2-pyridinyl-oxy)-1-(4-isopropoxyphenyl)indole-3-carboxylic acid (a) 2-Ethoxycarbonylmethyl-1-(4-isopropoxyphenyl)-5-(3-methoxycarbonyl-6-methyl-2-pyridinyloxy)indole-3-carboxylic acid ethyl ester The sub-title compound was prepared in accordance with step (a) Example 24 from 2-ethoxycarbonylmethyl-5-hydroxy-1-(4-isopropoxyphenyl)-indole-3-carboxylic acid ethyl ester (250 mg, 0.59 mmol, see (b) Example 12), K₂CO₃ (244 mg, 1.77 mmol), 2-chloro-6-methylnicotinic acid methyl ester (163 mg, 0.88 mmol), 18-crown-6 (16 mg, 0.06 mmol) and DMF (2 mL). The reaction mixture was heated at 90° C. for 4 d and worked-up as described before. Yield 80 mg (32%).

(b) 2-Carboxymethyl-5-(3-carboxy-6-methyl-2-pyridinyl-oxy)-1-(4-isopropoxyphenyl)indole-3-carboxylic acid The title compound was prepared in accordance with Example 3 from 2-ethoxycarbonylmethyl-1-(4-isopropoxyphenyl)-5-(3-methoxycarbonyl-6-methyl-2-pyridinyloxy)indole-3-carboxylic acid ethyl ester (60 mg, 0.10 mmol, see step (a) Example 29) Yield 20 mg (40%), mp 179° C.

200 MHz ¹H-NMR spectrum (DMSO-d₆), δ: 1.33 (d, J=5.9 Hz, 6H); 2.26 (s, 3H); 3.87 (s, 2H); 4.73 (heptet, J=5.9 Hz, 1H); 6.90 (dd, J=8.9, 2.1 Hz, 1H); 6.97 (d, J=8.9 Hz, 1H); 7.04 (d, J=7.7 Hz, 1H); 7.10-7.19 (m, 2H); 7.30-7.39 (m, 2H); 7.71 (d, J=2.0 Hz, 1H); 8.12 (d, J=7.7 Hz, 1H); 12.3-13.5 (br s, 3H).

Example 30

5-(3-Aminocarbonyl-6-methyl-2-pyridin-yloxy)-2-carboxymethyl 1-(4-isopropoxyphenyl)indole-3-carboxylic acid The title compound was prepared in accordance with step (b) Example 24 from (2-carboxymethyl-5-(3-cyano-6-methyl-2-pyridinyloxy)-1-(4-isopropoxyphenyl)indole-3-carboxylic acid ethyl ester (184 mg, 0.36 mmol, see step (b) Example 28), NaOH (aq, 2 M, 0.9 mL) and EtOH (1.5 mL). The mixture was heated at 80° C. for 4 h and the title compound was isolated as described before. Yield 40 mg (22%), mp 196° C.

200 MHz ¹H-NMR spectrum (DMSO-d₆), δ: 1.34 (d, J=5.9 Hz, 6H); 2.24 (s, 3H); 3.72 (s, 2H); 4.73 (heptet, J=5.9 Hz, 1H); 6.95 (s, 2H); 7.094 (d, J=7.8 Hz, 1H); 7.09-7.20 (m, 2H); 7.29-7.40 (m, 2H); 7.66-7.80 (m, 2H); 7.82 (s, 1H); 8.10 (d, J=7.8 Hz, 1H).

Example 31

2-Carboxymethyl-1-(4-isopropoxyphenyl)-5-(4-trifluorometoxyphenoxy)indole-3-carboxylic acid (a) 2-Ethoxycarbonylmethyl-1-(4-isopropoxyphenyl)-5-(4-trifluoromethoxyphen-oxy)indole-3-carboxylic acid ethyl ester The sub-title compound was prepared in accordance with step (c) Example 1 from 2-ethoxycarbonylmethyl-5-hydroxy-1-(4-isopropoxyphenyl)-indole-3-carboxylic acid ethyl ester (212 mg, 0.50 mmol, see step (b) Example 12) and 4-trifluoromethoxyphenylboronic acid (154 mg, 0.75 mmol). Yield 156 mg (53%).

(b) 9-Carboxymethyl-1-(4-isopropoxyphenyl)-5-(4-trifluorometoxyphenoxy)indole-3-carboxylic acid A mixture of 2-ethoxycarbonylmethyl-1-(4-isopropoxyphenyl)-5-(4-trifluoro-methoxyphenoxy)indole-3-carboxylic acid ethyl ester (150 mg, 0.26 mmol, see step (a) above), NaOH (aq, 2 M, 1.0 mL) and dioxane (0.5 mL) was heated at reflux for 6 h. The title compound was isolated in accordance with step (d) Example 1. Yield 87 mg (63%), mp 210° C.

200 MHz $^1$H-NMR spectrum (DMSO-$d_6$), δ: 1.33 (d, J=6.0 Hz, 6H); 3.96 (s, 2H); 4.73 (heptet, J=6.0 Hz, 1H); 6.96 (dd, J=8.8, 2.0 Hz, 1H); 7.00-7.09 (m, 3H); 7.10-7.20 (m, 2H); 7.28-7.40 (m, 4H); 7.72 (d, J=2.0 Hz, 1H); 12.2-12.8 (br s, 2H).

Example 32

2-Carboxymethyl-1-(4-isopropoxyphenyl)-5-(3-trifluorometoxyphenoxy)indole-3-carboxylic acid (a) 2-Ethoxycarbonylmethyl-1-(4-isopropoxyphenyl)-5-(3-trifluoromethoxyphen-oxy)indole-3-carboxylic acid ethyl ester The sub-title compound was prepared in accordance with step (a) Example 24 from 1-(4-isopropoxyphenyl)-2-ethoxycarbonylmethyl-5-hydroxyindole-3-carboxylic acid ethyl ester (212 mg, 0.50 mmol, see (b) Example 12) and 3-trifluoromethoxyphenylboronic acid. Yield 142 mg (48%).

(b) 2-Carboxymethyl-1-(4-isopropoxyphenyl)-5-(3-trifluorometoxyphenoxy)indole-3-carboxylic acid The title compound was prepared in accordance with step (b) Example 24 from 2-ethoxycarbonylmethyl-1-(4-isopropoxyphenyl)-5-(3-trifluoromethoxyphenoxy)indole-3-carboxylic acid ethyl ester (140 mg, 0.24 mmol, see step (a) above Yield 38 mg (30%), mp 197° C.

200 MHz $^1$H-NMR spectrum (DMSO-$d_6$), δ: 1.33 (d, J=5.9 Hz, 6H); 3.85 (s, 2H); 4.72 (heptet, J=5.9 Hz, 1H); 6.90-7.10 (m, 5H); 7.10-7.19 (m, 2H); 7.28-7.39 (m, 2H); 7.40-7.52 (m, 1H); 7.75 (d, J=1.9 Hz, 1H); 11.7-14.6 (br s, 2H).

Example 33

Carboxymethyl-5-(3-carboxyphenoxy)-1-(4-isopropoxyphenyl)indole-3-carboxylic acid (a) 2-Ethoxycarbonylmethyl-1-(4-isopropoxyphenyl)-5-(3-etoxycarbonylphenoxy)indole-3-carboxylic acid ethyl ester The sub-title compound was prepared in accordance with step (a) Example 24 from 2-ethoxycarbonylmethyl-5-hydroxy-1-(4-isopropoxyphenyl)indole-3-carboxylic acid ethyl ester (212 mg, 0.50 mmol, see (b) Example 12) and 3-(etoxycarbonyl)phenylboronic acid (145 mg, 0.75 mmol). Yield 162 mg, 56%.

(b) 2-Carboxymethyl-1-(4-isopropoxyphenyl)-5-(3-carboxyphenoxy)indole-3'-carboxylic acid The title compound was prepared in accordance with step (b) Example 24 from 2-ethoxycarbonylmethyl-1-(4-isopropoxyphenyl)-5-(3-etoxycarbonylphenoxy)indole-3-carboxylic acid ethyl ester (160 mg, 0.28 mmol, see step (a) above). Yield 90 mg (66%), mp 236° C.

200 MHz $^1$H-NMR spectrum (DMSO-$d_6$), δ: 1.33 (d, J=6.0 Hz, 6H); 3.97 (s, 2H); 4.72 (heptet, J=6.0 Hz, 1H); 6.97 (dd, J=8.9, 2.0 Hz, 1H); 7.04 (d, J=8.9 Hz, 1H); 7.08-7.19 (m, 2H); 7.27 (ddd, J=8.1, 2.4 Hz, 1H); 7.31-7.41 (m, 3H); 7.48 (t, J=7.9 Hz, 1H); 7.60-7.68 (m, 1H); 7.72 (d, J=2.0 Hz, 1H); 12.4-12.8 (br s, 3H).

Example 34

2-Carboxymethyl-1-(4-methoxyphenyl)-5-(3-trifluoromethylphenoxy)indole-3-carboxylic acid (a) 2-Ethoxycarbonylmethyl-1-(4-methoxyphenyl)-5-(3-trifluoromethylphenoxy)indole-3-carboxylic acid ethyl ester The sub-title compound was prepared in accordance with step (a) Example 24 from 2-ethoxycarbonylmethyl-1-(4-methoxyphenyl)-5-hydroxyindole-3-carboxylic acid ethyl ester (153 mg, 0.40 mmol, see (b) Example 4) and 3-trifluoromethylphenylboronic acid (114 mg, 0.60 mmol). Yield 166 mg (77%).

(b) 2-Carboxymethyl-1-(4-methoxyphenyl)-5-(3-trifluoromethylphenoxy)indole-3-carboxylic acid The title compound was prepared in accordance with step (b) Example 24 from 2-ethoxycarbonylmethyl-1-(4-methoxyphenyl)-5-(3-trifluoromethylphenoxy)indole-3-carboxylic acid ethyl ester (160 mg, 0.30 mmol, see step (a) above). Yield 96 mg (66%), mp 210° C.

200 MHz $^1$H-NMR spectrum (DMSO-$d_6$), δ: 3.86 (s, 3H); 3.97 (s, 2H); 6.96-7.08 (m, 2H); 7.14-7.30 (m, 4H); 7.34-7.47 (m, 3H); 7.53-7.64 (m, 1H); 7.75 (d, J=1.6 Hz, 1H); 12.1-12.7 (br s, 2-H).

Example 35

2-Carboxymethyl)-5-(4-isopropoxyphenoxy)-1-(4-methoxyphenylindole-3-carboxylic acid

(a) 2-Ethoxycarbonylmethyl-5-(4-isopropoxyphenoxy)-1-(4-methoxyphenyl)indole-3-carboxylic acid ethyl ester The sub-title compound was prepared in accordance with step (a) Example 24 from 2-ethoxycarbonylmethyl-5-hydroxy-1-(4-methoxyphenyl)indole-3-carboxylic acid ethyl ester (153 mg, 0.40 mmol and 4-isopropoxyphenylboronic acid (108 mg, 0.60 mmol). Yield 111 mg, 52%.

(b) 2-Carboxymethyl-5-(4-isopropoxyphenoxy)-1-(4-methoxyphenyl)indole-3-carboxylic acid The title compound was prepared in accordance with step (b) Example 24 from 2-ethoxycarbonylmethyl-5-(4-isopropoxyphenoxy) 1-(4-methoxyphenyl)indole-3-carboxylic acid ethyl ester (100 mg, 0.19 mmol, see step (a) above). Yield 70 mg (77%), mp 226° C.

200 MHz $^1$H-NMR spectrum (DMSO-$d_6$), δ: 1.25 (d, J=6.0 Hz, 6H); 3.86 (s, 3H); 3.93 (s, 2H); 4.52 (heptet. J=6.0 Hz, 1H); 6.84-6.99 (m, 6H); 7.11-7.22 (m, 2H); 7.29-7.40 (m, 2H); 7.61 (d, J=1.8 Hz, 1H); 11.9-12.7 (br s, 2H).

Example 36

2-Carboxymethyl-1-(4-methoxyphenyl)-5-(4-methylsulfonylphenoxy)indole-3-carboxylic acid

(a) 2-Ethoxycarbonylmethyl-1-(4-methoxyphenyl)-5-(4-methylsulfonylphenoxy)indole-3-carboxylic acid ethyl ester The sub-title compound was prepared in accordance with step (a) Example 24 from 2-ethoxycarbonylmethyl-5-hydroxy-1-(4-methoxyphenyl)indole-3-carboxylic acid ethyl ester (153 mg, 0.40 mmol, see (b) Example 4), Cu(OAc)$_2$ (73 mg, 0.40 mmol) and 4-(methylsulfonyl)phenylboronic acid (120 mg, 0.60 mmol). Yield 171 mg (77%).

(b) 2-Carboxymethyl-1-(4-methoxyphenyl)-5-(4-methylsulfonylphenoxy)indole-3-carboxylic acid The title compound was prepared in accordance with step (b) Example 24 from 2-ethoxycarbonylmethyl-1-(4-methoxyphenyl)-5-(4-methylsulfonylphenoxy)indole-3-carboxylic acid ethyl ester (165 mg, 0.30 mmol, see step (a) above). Yield 100 mg (67%), mp 222° C.

200 MHz $^1$H-NMR spectrum (DMSO-$d_6$), δ: 3.18 (s, 3H); 3.86 (s, 3H); 3.98 (s, 2H); 6.97-7.06 (m, 2H); 7.08-7.24 (m, 4H); 7.33-7.42 (m, 2H); 7.78 (d, J=1.8 Hz, 1H); 7.83-7.92 (m, 2H); 12.1-12.8 (br s, 2H).

Example 37

5-[3,5-Bis(trifluoromethyl)phenoxy]-2-carboxymethyl-1-(4-methoxyphenyl) indole-3-carboxylic acid

(a) 5-[3,5-Bis(trifluoromethyl)phenoxy]-2-ethoxycarbonylmethyl-1-(4-methoxyphenyl)indole-3-carboxylic acid ethyl ester The sub-title compound was prepared in accordance with step (a) Example 24 from 2-ethoxycarbonylmethyl-5-hydroxy-1-(4-methoxyphenyl)indole-3-carboxylic acid ethyl ester (153 mg, 0.40 mmol, see (b) Example 4) and 3,5-bis(trifluoromethyl)phenylboronic acid (155 mg, 0.60 mmol). Yield 106 mg, 43%.

(b) 5-[3,5-Bis(trifluoromethyl)phenoxy]-2-carboxymethyl-1-(4-methoxyphenyl indole-3-carboxylic acid The title compound was prepared in accordance with step (b) Example 24 from 5-[3,5-bis(trifluoromethyl)phenoxy]-2-ethoxycarbonylmethyl-1-(4-methoxyphenyl)indole-3-carboxylic acid ethyl ester (100 mg, 0.16 mmol, see step (a) above). Yield 80 mg, (90%), mp 232° C.

200 MHz $^1$H-NMR spectrum (DMSO-$d_6$), δ: 3.86 (s, 3H); 3.99 (s, 2H); 7.07 (s, 2H); 7.13-7.24 (m, 2H); 7.34-7.45 (m, 2H); 7.59 (s, 2H); 7.76-7.86 (I 2H); 12.1-12.9 (br s, 2H).

Example 38

1-(4-tert-Butylphenyl)-2-carboxymethyl-5-(5-carboxypyridin-2-yloxy)-6-chloro-indole-3-carboxylic acid

(a) 3-(4-tert-Butylphenylamino)pent-2-enedioic acid diethyl ester

The sub-title compound was prepared in accordance with step (a) Example 1 from 4-tert butylaniline.

(b) 1-(4-tert-Butylphenyl)-6-chloro-2-ethoxycarbonylmethyl-5-hydroxyindole-3-carboxylic acid ethyl ester The sub-title compound was prepared in accordance with step (b) Example 1 from 3-(4-tert-butylphenylamino)pent-2-enedioic acid diethyl ester (6.2 g, 18.6 mmol, see step (a) above) and 2-chloro-1,4-benzoquinone (3.1 g, 22 mmol). Yield 266 mg (3%).

(c) 1-(4-tert-Butylphenyl)-6-chloro-5-(5-dimethylcarbamoyl-pyridin-2-yloxy)-2-ethoxycarbonylmethylindole-3-carboxylic acid ethyl ester 1-(4-tert-Butylphenyl)-6-chloro-2-ethoxycarbonylmethyl-5-hydroxyindole-3-carboxylic acid ethyl ester (120 mg, 0.26 mmol, see step (b) above), 6-chloro-N,N-dimethylnicotinamide (72 mg, 0.39 mmol), K$_2$CO$_3$ (181 mg, 1.31 mmol) and DMF (3 mL) was heated at 115° C. for 96 h and filtered through Celite®. The solids were washed with EtOAc and the combined filtrates concentrated and purified by chromatography to give the sub-title compound. Yield 48 mg (78%).

(d) 1-(4-tert-Butylphenyl)-2-carboxymethyl-5-(5-carboxypyridin-2-yloxy)-6-chloroindole-3-carboxylic acid A mixture of 1-(4-tert-butylphenyl)-6-chloro-5-(5-dimethylcarbamoyl-pyridin-2-yloxy)-2-ethoxycarbonylmethylindole-3-carboxylic acid ethyl ester (124 mg, 4.07 mmol; see step (c) above), NaOH (aq, 2 M, 1.0 mL) and dioxane (2.0 mL) was heated at reflux for 48 h, cooled, acidified to pH 2 with HCl (aq, 1 M) and extracted with EtOAc. The combined extracts were washed with H$_2$O and brine, dried (Na$_2$SO$_4$), concentrated and purified by chromatography to give the title compound. Yield 40 mg (36%), mp 223-235° C.

200 MHz $^1$H NMR spectrum: (DMSO-d$_6$), δ: 1.38 (s, 9H); 3.63 (br s, 2H); 7.07 (s, 1H); 7.15 (d, J=8.8 Hz, 1H); 7.37-7.46 (m, 2H); 7.62-7.71 (m, 2H); 7.94 (s, 1H); 8.28 (dd, J=8.6, 2.2 Hz, 1H); 8.60 (d, J=2.2 Hz, 1H).

Example 39

2-Carboxymethyl-5-(5-carboxypyridin-2-yl)oxy-1-(4-diethylaminophenyl)indole-3-carboxylic acid (a) 1-(4-Diethylaminophenyl)-5-(5-dimethylcarbamoylpyridin-2-yloxy)-2-ethoxycarbonylmethylindole-3-carboxylic acid ethyl ester The title compound was prepared in accordance with step (c) Example 38 from 1-(4-diethylaminophenyl)-2-ethoxycarbonylmethyl-5-hydroxyindole-3-carboxylic acid ethyl ester (120 mg, 0.28 mmol, see step (b) Example 1) and 6-chloro-N,N-dimethyl-nicotinamide (78 mg, 0.42 mmol). Yield 79 mg (48%).

(b) 2-Carboxymethyl-5-(5-carboxypyridin-2-yl)oxy-1-(4-diethylaminophenyl)indole-3-carboxylic acid The title compound was prepared in accordance with step (d) Example 38 from 1-(4-diethylaminophenyl)-5-(5-dimethylcarbamoylpyridin-2-yloxy)-2-ethoxycarbonylmethyl-indole-3-carboxylic acid ethyl ester (79 mg, 0.135 mmol, see step (a) above). Yield 16 mg (23%).

200 MHz $^1$H NMR spectrum: (DMSO-d$_6$), δ: 1.15 (t, J=6.9 Hz, 6H); 3.42 (q, J=6.9 Hz, 4H); 3.92 (s, 2H); 6.82 (d, J=8.8 Hz, 2H); 6.96-7.11 (m, 3H); 7.12-7.22 (m, 2H); 7.76 (d, J=2.0 Hz, 1H); 8.25 (dd, J=8.6, 2.4 Hz, 1H); 8.64 (d, J=2.4 Hz, 1H).

Example 40

5-(5-Aminopyridin-2-yloxy)-2-carboxymethyl-1-(4-isopropoxyphenyl)indole-3-carboxylic acid ethyl ester (a) 2-Ethoxycarbonylmethyl-1-(4-isopropoxyphenyl)-5-(5-nitropyridin-2-yloxy)indole-3-carboxylic acid ethyl ester The sub-title compound was prepared in accordance with step (c) Example 38 from 2-ethoxycarbonylmethyl-5-hydroxy-1-(4-isopropoxyphenyl)indole-3-carboxylic acid ethyl ester (150 mg, 0.35 mmol, see (b) Example 12) and 2-chloro-5-nitropyridin (67 mg, 0.42 mmol). Yield 187 mg (98%).

(b) 5-(5-Aminopyridin-9-yloxy)-2-ethoxycarbonylmethyl-1-(4-isopropoxyphenyl)indole-3-carboxylic acid ethyl ester 2-Ethoxycarbonylmethyl-1-(4-isopropoxyphenyl)-5-(5-nitropyridin-2-yloxy)indole-3-carboxylic acid ethyl ester (175 mg, 0.32 mmol; see step (a) above) in MeOH (10 mL) was hydrogenated at ambient temperature and pressure over Pd—C (10%, 60 mg) for 0.5 h. The mixture was filtered through Celite® and the solids washed with EtOAc. The combined liquids were concentrated to give the sub-title compound. Yield 157 mg 95%).

(c) 5-(5-Aminopyridin-2-yloxy)-2-carboxymethyl-1-(4-isopropoxyphenyl)indole-3-carboxylic acid ethyl ester A mixture of 5-(5-aminopyridin-2-yloxy)-2-ethoxycarbonylmethyl-1-(4-isopropoxyphenyl)indole-3-carboxylic acid ethyl ester (185 mg, 0.36 mmol; see step (b) above), NaOH (aq, 2 M, 2 mL) and EtOH (15 mL) was stirred at rt for 20 h, acidified to pH 2 with HCl (aq, 1 M) and extracted with EtOAc. The combined extracts were washed with H$_2$O and brine, dried (Na$_2$SO$_4$), concentrated and purified by chromatography to give the sub-title compound. Yield 130 mg (74%).

200 MHz $^1$H NMR spectrum: (DMSO-d$_6$), δ: 1.28 (t, J=7.1 Hz, 3H); 1.33 (d, J=6.0 Hz, 6H); 3.92 (s, 2H); 4.26 (q, J=7.1 Hz, 2H); 4.72 (septet, J=6.0 Hz, 1H); 6.76 (d, J=8.6 Hz, 1H); 6.87 (dd, J=8.8, 2.1 Hz, 1H) 6.95 (d, J=8.8 Hz, 1H); 7.05-7.20 (m, 3H); 7.26-7.36 (m, 2H); 7.54 (d, J=2.8 Hz, 1H); 7.60 (d, J=2.1 Hz, 1H).

Example 41

5-(5-Aminopyridin-2-yloxy)-1-(4-isopropoxyphenyl)indole-2,3-dicarboxylic acid 3-methyl ester (a) 1-(4-isopropoxyphenyl)-5-(5-nitropyridin-2-yloxy)indole-2,3-dicarboxylic acid dimethyl ester The title compound was prepared in accordance with step (c) Example 38 from 5-hydroxy-1-(4-isopropoxyphenyl)indole-2,3-dicarboxylic acid dimethyl ester (150 mg, 0.39 mmol, see (b) Example 12) and 2-chloro-5-nitropyridin (75 mg, 0.47 mmol). Yield 169 mg (86%).

(b) 5-(5-Aminopyridin-2-yloxy)-1-(4-isopropoxyphenyl)indole-2,3-dicarb-oxylic acid dimethyl ester The title compound was prepared in accordance with step (b) Example 40 from 1-(4-isopropoxyphenyl)-5-(5-nitropyridin-2-yloxy)indole-2,3-dicarboxylic acid dimethyl ester (169 mg, 0.33 mmol, see step (a) above). Yield 140 mg (87%).

(c) 5-(5-Amino-pyridin-2-yloxy)-1-(4-isopropoxyphenyl)indole-2,3-dicarb-oxylic acid 3-methyl ester The title compound was prepared in accordance with step (d) Example 38 from 5-(5-aminopyridin-2-yloxy)-1-(4-isopropoxyphenyl)indole-2,3-dicarboxylic acid dimethyl ester (140 mg, 0.29 mmol, see step (c) above). Yield 40 mg (30%), mp 178-218° C. (dec.).

200 MHz $^1$H NMR spectrum (DMSO-d$_6$), δ: 1.31 (d, J=6.0 Hz, 6H); 3.68 (s, 3H); 4.6-5.4 (br s, 2H); 4.66 (heptet, J=6.0 Hz, 1H); 6.70 (d, J=8.7 Hz, 1H); 6.74-6.83 (m, 1H); 6.96-7.09 (m, 4H); 7.0-7.2 (br s, 1H), 7.34-7.44 (m, 2H); 7.50 (d, J=2.8 Hz, 1H); 7.55 (d, J=2.3 Hz, 1H).

Example 42

2-Carboxymethyl-1-(4-isopropoxyphenyl)-5-(3-trifluoromethylphenoxy)indole-3-carboxylic acid (a) 2-Ethoxycarbonylmethyl-1-(4-isopropoxyphenyl)-5-(3-trifluoromethylphenoxy)indole-3-carboxylic acid ethyl ester The sub-title compound was prepared in accordance with step (c) Example 1 from 2-ethoxycarbonylmethyl-5-hydroxy-1-(4-isopropoxyphenyl)indole-3-carboxylic acid ethyl ester (80 mg, 0.19 mmol, see (b) Example 12) and 3-trifluoromethylphenylboronic acid (54 mg, 0.28 mmol). Yield 53 mg (50%).

(b) 2-Carboxymethyl-1-(4-isopropoxyphenyl)-5-(3-trifluoromethylphenoxy)indole-3-carboxylic acid The title compound was prepared in accordance with step (b) Example 2 from 2-ethoxycarbonylmethyl-1-(4-isopropoxyphenyl)-5-(3-trifluoromethylphenoxy)indole-3-carboxylic acid ethyl ester (53 mg, 0.093 mmol, see step (a) above). Yield 30 mg (63%), mp 203° C. after recrystallisation from EtOH.

200 MHz $^1$H NMR spectrum (DMSO-$d_6$), δ: 1.33 (d, J=6.0 Hz, 6H); 3.95 (s, 2H); 4.72 (heptet, J=6.0 Hz, 1H); 6.93-7.05 (m, 2H); 7.06-7.18 (m, 2H); 7.19-7.47 (m, 5H); 7.57 (t, J=7.8 Hz, 1H); 7.75 (d, J=1.8 Hz, 1H); 12.3-12.6 (br s, 2H).

Example 43

2-(4-Carboxyphenyl)-1-(4-isopropoxyphenyl)-5-(4-trifluoromethylphenoxy)indole-3-carboxylic acid (a) 1-(4-Isopropoxyphenylamino)-2-methoxycarbonylvinylbenzoic acid methyl ester The sub-title compound was prepared in accordance with step (a) Example 1 from p-isopropoxyaniline and 4-methoxycarbonylbenzoyl acetic acid methyl ester.

(b) 5-Hydroxy-1-(4-isopropoxyphenyl)-2-(4-methoxycarbonylphenyl)indole-3-carboxylic acid methyl ester The sub-title compound was prepared in accordance with step (b) Example 1 from 1-(4-isopropoxyphenylamino)-2-methoxycarbonylvinylbenzoic acid methyl ester (9.1 mmol, see step (a) Example 43). Yield 0.92 g (22%).

(c) 1-(4-Isopropoxyphenyl-2-(4-methoxycarbonylphenyl)-5-(4-trifluoromethylphenoxy)indole-3-carboxylic acid methyl ester The sub-title compound was prepared in accordance with step (c) Example 1 from 5-hydroxy-1-(4-isopropoxyphenyl)-2-(4-methoxycarbonylphenyl)indole-3-carboxylic acid methyl ester (161 mg, 0.35 mmol, see step (b) Example 43) and 4-trifluoromethylphenylboronic acid (100 mg, 0.53 mmol). Yield 130 mg (62%).

(d) 2-(4-Carboxyphenyl)-1-(4-isopropoxyphenyl)-5-(4-trifluoromethylphenoxy)indole-3-carboxylic acid The title compound was prepared in accordance with step (d) Example 2 from 1-(4-isopropoxyphenyl)-2-(4-methoxycarbonylphenyl)-5-(4-trifluoromethylphenoxy)indole-3-carboxylic acid methyl ester (100 mg, 0.16 mmol, see step (c) Example 43). Yield 89 mg (72%), mp 268-270° C.

200 MHz $^1$H-NMR (DMSO-$d_6$), δ: 1.24 (d, J=6.0 Hz, 6H); 4.61 (heptet, J=6.0 Hz, 1H); 6.87-6.99 (m, 2H); 7.04-7.29 (m, 6H); 7.43-7.56 (m, 2H); 7.68-7.78 (m, 2H); 7.79-7.86 (m, 2H); 7.88 (d, J=2.1 Hz; 1H); 12.0-13.2 (br s, 2H).

Example 44

1-(4-Isopropoxyphenyl)-5-(4-trifluoromethylphenoxy)indole-2,3-dicarboxylic acid 3-methyl ester (a) 1-(4-Isopropoxyphenyl)-5-(4-trifluoromethylphenoxy)indole-2,3-dicarb-oxylic acid dimethyl ester The sub-title compound was prepared in accordance with step (c) Example 1 from 5-hydroxy-1-(4-isopropoxyphenyl)indole-2,3-dicarboxylic acid dimethyl ester (250 mg, 0.65 mmol, see step (a) Example 19) and 4-trifluoromethylphenylboronic acid. Yield 230 mg (67%).

(b) 1-(4-Isopropoxyphenyl)-5-(4-trifluoromethylphenoxy)indole-2,3-dicarboxylic acid 3-methyl ester The title compound was prepared in accordance with step (d) Example 38 from 1-(4-isopropoxyphenyl)-5-(4-trifluoromethylphenoxy)indole-2,3-dicarboxylic acid dimethyl ester (230 mg, 0.44 mmol; see step (a) above). Yield 170 mg (76%), mp 191° C. after crystallisation from EtOH.

200 MHz $^1$H NMR spectrum: (DMSO-$d_6$, HMDSO), δ: 1.32 (d, J=6.0 Hz, 6H); 3.56 (s, 3H); 4.70 (heptet, J=6.0 Hz, 1H); 7.05-7.23 (m, 6H); 7.32-7.41 (m, 2H); 7.67-7.76 (m, 2H); 7.80 (dd, J=1.8 Hz, 1H).

Example 45

5-(4-tert-Butylphenoxy)-1-(4-isopropoxyphenyl)indole-2,3-dicarboxylic acid (a) 5-(4-tert-Butylphenoxy)-1-(4-isopropoxyphenyl)indole-2,3-dicarboxylic acid dimethyl ester The sub-title compound was prepared in accordance with step (c) Example 1 from 5-hydroxy-1-(4-isopropoxyphenyl)indole-2,3-dicarboxylic acid dimethyl ester (250 mg, 0.65 mmol, see step (a) Example 19) and 4-tert-butylphenylboronic acid (175 mg, 0.98 mmol). Yield 240 mg (72%).

(b) 5-(4-tert-Butylphenoxy)-1-(4-isopropoxyphenyl)indole-2,3-dicarboxylic acid

The title compound was prepared in accordance with step (d) Example 38 from 5-(4-tert-butylphenoxy)-1-(4-isopropoxyphenyl)indole-2,3-dicarboxylic acid dimethyl ester (95 mg, 0.18 mmol; see step (a) above). Yield 35 mg (39%).

200 MHz $^1$H NMR spectrum: (DMSO-$d_6$), δ: 1.26 (s, 9H); 1.32 (d, J=6.0 Hz, 6H); 4.66 (heptet, J=6.0 Hz, 1M); 6.82-7.03 (m, 6H); 7.10-7.19 (m, 2H); 7.30-7.39 (m, 2H); 8.07 (d, J=2.3 Hz, 1H).

Example 46

5-(4-tert-Butylphenoxy)-2-carboxymethyl-1-(4-isopropoxyphenyl)indole-3-carboxylic acid (a) 5-(4-tert-Butylphenoxy-2-ethoxycarbonylmethyl-1-(4-isopropoxyphenyl)indole-3-carboxylic acid ethyl ester The sub-title compound was prepared in accordance with step (c) Example 1 from 2-ethoxycarbonylmethyl-5-hydroxy-1-(4-isopropoxyphenyl)indole-3-carboxylic acid ethyl ester (250 mg, 0.59 mmol and 4-tert-butylphenylboronic acid (157 mg, 0.88 mmol). Yield 293 mg (90%).

(b) 5-(4-tert-Butylphenoxy-2-carboxymethyl-1-(4-isopropoxyphenyl)indole-3-carboxylic acid The title compound was prepared in accordance with step (d) Example 38 from 5-(4-tert-butylphenoxy)-2-ethoxycarbonylmethyl-1-(4-isopropoxyphenyl)indole-3-carboxylic acid ethyl ester (115 mg, 0.22 mmol; see step (a) above). Yield 97 mg (89%), after recrystallisation from EtOH.

200 MHz $^1$H NMR spectrum (DMSO-$d_6$), δ: 1.26 (s, 9H); 1.32 (d, J=6.0 Hz, 6H); 3.91 (s, 2H); 4.72 (heptet, J=6.0 Hz, 1H); 6.83-7.02 (m, 4H); 7.12 (d, J=8.9 Hz, 2H); 7.26-7.42 (m, 5H); 7.68 (d, J=2.0 Hz, 1H); 12.0-12.9 (br s, 1H).

Example 47

2-Carboxymethyl-1-(4-isopropoxyphenyl)-5-(4-trifluoromethylphenoxy)indole-3-carboxylic acid The title compound was prepared in accordance with step (d) Example 1 from 2-ethoxycarbonylmethyl-1-(4-isopropoxyphenyl)-5-(4-trifluoromethylphenoxy)indole-3-carboxylic acid ethyl ester (80 mg, 0.14 mmol; see step (c) Example 12). Yield 40 mg (56%).

200 MHz $^1$H NMR spectrum: (DMSO-$d_6$), δ: 1.33 (d, J=6.0 Hz, 6H); 3.4-3.5 (br s, 1H); 3.56 (s, 2H); 4.71 (heptet, J=6.0 Hz, 1H); 6.80-7.19 (m, 6H); 7.29-7.47 (m, 2H); 7.66 (d, J=8.8 Hz, 2H); 7.78-7.86 (m, 1H); 8.31 (s, 1H).

Example 48

1-(4-Isopropoxyphenyl-5-(4-trifluoromethylphenoxy)indole-2-dicarboxylic acid The title compound was prepared in accordance with step (d) Example 1 from 1-(4-isopropoxyphenyl)-5-(4-trifluoromethylphenoxy)indole-2,3-dicarboxylic acid dimethyl ester (80 mg, 0.15 mmol; see step (a) Example 44). Yield 50 mg (67%).

200 MHz $^1$H NMR spectrum: (DMSO-$d_6$), δ: 1.33 (d, J=6.0 Hz, 6H); 4.67 (heptet, J=6.0 Hz, 1H); 6.86-7.25 (m, 8H); 7.69 (d, J=8.7 Hz, 2H); 8.18 (d, 1H); 19.77 (s, 2H).

Example 49

2-Carboxymethyl-5-(3-chlorophenoxy)-1-(4-diethylaminophenyl)indole-3-carboxylic acid

(a) 5-(3-Chlorophenoxy)-1-(4-diethylaminophenyl)-2-ethoxycarbonylmethyl-indole-3-carboxylic acid ethyl ester The sub-title compound was prepared in accordance with step (c) Example 1 from 1-(4-diethylaminophenyl)-2-ethoxycarbonylmethyl-5-hydroxyindole-3-carboxylic acid ethyl ester (150 mg, 0.34 mmol, see step (b) Example 1) and 3-chlorophenylboronic acid (110 mg, 0.68 mmol). Yield 100 mg (53%).

(b) 2-Carboxymethyl-5-(3-chlorophenoxy)-1-(4-diethylaminophenyl)indole-3-carboxylic acid A mixture of 5-(3-chlorophenoxy)-1-(4-diethylaminophenyl)-2-ethoxycarbonylmethyl-indole-3-carboxylic acid ethyl ester (100 mg, 0.18 mmol, see step (a) above), NaOH (1 M in methanol, 2 mL, 2.0 mmol), NaOH (aq, 1 M, 2 mL, 2.0 mmol) and dioxane (2 mL) was stirred at reflux for 4 h, cooled, acidified to pH 4 with HCl (aq, 1 M) and extracted with EtOAc. The combined extracts were washed with H$_2$O and brine, dried (Na$_2$SO$_4$), concentrated and purified by chromatography. Yield 50 mg (56%), mp 186-191° C.

200 MHz $^1$H-NMR (DMSO-$d_6$), δ: 1.15 (t, J=6.8 Hz, 6H); 3.41 (q, J=7.2 Hz, 4H, overlapped with DMSO and water); 3.88 (s, 2H); 6.76-6.87 (m, 2H); 6.88-7.23 (m, 7H); 7.36 (t, J=8.2 Hz, 1H); 7.71 (d, J=1.8 Hz, 1H); 11.7-13.5 (br s, 2H).

Example 50

5-(3-Chlorophenoxy)-1-(4-isopropoxyphenyl)indole-2,3-dicarboxylic acid

(a) 5-(3-Chlorophenoxy)-1-(4-isopropoxyphenyl)-indole-2,3-dicarboxylic acid dimethyl ester The sub-title compound was prepared in accordance with step (a) Example 18 from 5-hydroxyindole-1-(4-isopropoxyphenyl)-2,3-dicarboxylic acid dimethyl ester (150 mg-0.39 mmol, see step (a) Example 19) and 3-chlorophenylboronic acid (120 mg, 0.78 mmol). Yield 93 mg (49%).

(b) 5-(3-Chlorophenoxy)-1-(4-isopropoxyphenyl) indole-2,3-dicarboxylic acid

The title compound was prepared in accordance with step (d) Example 2 from 5-(3-chlorophenoxy)-1-(4-isopropoxyphenyl)-indole-2,3-dicarboxylic acid dimethyl ester (92 mg, 0.19 mmol, see step (a) above). Yield 50 mg (57%), mp 182-190° C.

200 MHz $^1$H-NMR (DMSO-$d_6$), δ: 1.32 (d, J=6.0 Hz, 6H); 4.70 (heptet, J=6.0 Hz, 1H); 6.90-6.98 (m, 1H); 6.99-7.03 (m, 1H); 7.03-7.91 (m, 5H); 7.30-7.44 (m, 3H); 7.73-7.80 (m, 1H).

Example 51

2-Carboxymethyl-5-(4-chlorophenoxy)-1-(4-(trifluoromethoxy)phenyl)indole-3-carboxylic acid

(a) 2-Carboxymethyl-5-(4-chlorophenoxy)-1-(4-(trifluoromethoxy)phenyl)indole-3-carboxylic acid ethyl ester The sub-title compound was prepared in accordance with step (c) Example 1 from 2-ethoxycarbonylmethyl-5-hydroxy-1-(4-trifluoromethoxyphenyl)indole-3-carboxylic acid ethyl ester (150 mg, 0.39 mmol, see step (b) Example 9) and 4-chlorophenylboronic acid (110 mg, 0.68 mmol). Yield 140 mg (74%).

(b) 2-Carboxymethyl-5-(4-chlorophenoxy)-1-(4-trifluoromethoxyphenyl)indole-3-carboxylic acid The title compound was prepared in accordance with step (d) Example 2 from 2-carboxymethyl-5-(4-chlorophenoxy)-1-(4-(trifluoromethoxy)phenyl)indole-3-carboxylic acid ethyl ester (140 mg, 0.25 mmol, see step (a) above). Yield 57 mg (45%), mp 198-202° C.

200 MHz $^1$H-NMR (CDCl$_3$), δ: 3.88 (s, 2H); 6.90-7.02 (m, 3H); 7.06 (d, J=8.9 Hz, 1H); 7.34-7.43 (m, 2H); 7.57-7.70 (m, 4H); 7.72 (d, J=2.0 Hz, 1H); 12.2-14.3 (br s, 2H).

Example 52

2-Carboxymethyl-5-(3-chlorophenoxy)-1-(4-trifluoromethoxyphenyl)indole-3-carboxylic acid (a) 5-(3-Chlorophenoxy)-2-ethoxycarbonylmethyl-1-(4-trifluoromethoxyphenyl)indole-3-carboxylic acid ethyl ester The sub-title compound was prepared in accordance with step (c) Example 1 from 2-ethoxycarbonylmethyl-5-hydroxy-1-(4-trifluoromethoxyphenyl)indole-3-carboxylic acid ethyl ester (150 mg, 0.34 mmol, see step (b) Example 9) and 3-chlorophenylboronic acid (10 mg, 0.68 mmol). Yield 180 mg (95%).

(b) 2-Carboxymethyl-5-(3-chlorophenoxy)-1-(4-trifluoromethoxyphenyl)indole-3-carboxylic acid The title compound was prepared in accordance with step (d) Example 2 from 5-(3-chlorophenoxy)-2-ethoxycarbonylmethyl-1-(4-trifluoromethoxyphenyl)indole-3-carboxylic acid ethyl ester (180 mg, 0.32 mmol, see step (a) above). Yield 66 mg (41%), mp 190-195° C.
200 MHz $^1$H-NMR (CDCl$_3$), δ: 3.86 (s, 2H); 6.93 (dd, J=8.0 and 2.2 Hz, 1H); 6.97-7.17 (m, 4H); 7.31-7.42 (m, 1H); 7.61-7.71 (m, 4H); 7.75 (d, J=2.2 Hz, 1H); 11.6-13.8 (br s, 2H).

Example 53

2-Carboxymethyl)-5-(3-trifluoromethoxyphenoxy)-1-(4-trifluoromethoxyphenyl)indole-3-carboxylic acid (a) 2-Ethoxycarbonylmethyl-5-(3-trifluoromethoxy)-1-(4-trifluoromethoxyphenyl)indole-3-carboxylic acid ethyl ester The sub-title compound was prepared in accordance with step (c) Example 1 from 2-ethoxycarbonylmethyl-5-hydroxy-1-(4-trifluoromethoxyphenyl)indole-3-carboxylic acid ethyl ester (150 mg, 0.34 mmol, see step (b) Example 9) and 3-trifluoromethoxyphenylboronic acid. Yield 165 mg (82%).

(b) 2-Carboxymethyl-5-(3-trifluoromethoxyphenoxy)-1-(4-trifluoromethoxyphenyl)indole-3-carboxylic acid The title compound was prepared in accordance with step (d) Example 2 from 2-ethoxycarbonylmethyl-5-(3-trifluoromethoxy)-1-(4-trifluoromethoxyphenyl)indole-3-carboxylic acid ethyl ester (165 mg, 0.28 mmol, see step (a) above). Yield 92 mg (61%), mp 188-193° C.
200 MHz $^1$H-NMR (DMSO-d$_6$), δ: 3.95 (s, 2H); 7.01 (dd, J=8.9 and 2.2 Hz, 1H); 7.10 (d, J=8.9 Hz, 1H); 7.20-7.30 (m, 2H); 7.43 (d, J=7.7 Hz, 1H); 7.56 (d, J=8.2 Hz, 1H); 7.60-7.72 (m, 4H); 7.77 (d, J=2.2 Hz, 1H); 12.0-14.1 (br s, 2H).

Example 54

2-Carboxymethyl-5-(3,4-dichlorophenoxy-1-(4-trifluoromethoxyphenyl)indole-3-carboxylic acid (a) 2-Ethoxycarbonylmethyl-5-(3,4-dichlorophenoxy)-1-(4-trifluoromethoxyphenyl)indole-3-carboxylic acid ethyl ester The sub-title compound was prepared in accordance with step (c) Example 1 from 2-ethoxycarbonylmethyl-5-hydroxy-1-(4-trifluoromethoxyphenyl)indole-3-carboxylic acid ethyl ester (150 mg, 0.34 mmol, see step (b) Example 9) and 3,4-dichlorophenylboronic acid (130 mg, 0.68 mmol). Yield 100 mg (50%).

(b) 2-Carboxymethyl-5-(3,4-dichlorophenoxy)-1-(4-trifluoroethoxyphenyl)indole-3-carboxylic acid The title compound was prepared in accordance with step (d) Example 2 from 2-ethoxycarbonylmethyl-5-(3,4-dichlorophenoxy)-1-(4-trifluoromethoxyphenyl)indole-3-carboxylic acid ethyl ester (100 mg, 0.17 mmol, see step (a) above). Yield 55 mg (60%), mp 205-210° C.
200 MHz $^1$H-NMR (DMSO-d$_6$), δ: 3.83 (s, 2H); 6.91-7.01 (m, 2H); 7.08 (d, J=8.9 Hz, 1H); 7.22 (d, J=2.4 Hz, 1H); 7.58 (d, J=8.9 Hz, 1H); 7.61-7.68 (m, 4H); 7.77 (d, J=2.2 Hz, 1H); 11.2-15.2 (br s, 2H).

Example 55

2-Carboxymethyl-5-(3,5-dichlorophenoxy)-1-(4-trifluoromethoxyphenyl)indole-3-carboxylic acid (a) 2-Ethoxycarbonylmethyl-5-(3,5-dichlorophenoxy)-1-(4-trifluoromethoxyphenyl)indole-3-carboxylic acid ethyl ester The sub-title compound was prepared in accordance with step (c) Example 1 from 2-ethoxycarbonylmethyl-5-hydroxy-1-(4-trifluoromethoxyphenyl)indole-3-carboxylic acid ethyl ester (160 mg, 0.36 mmol, see step (b) Example 9) and 3,5-dichlorobenzeneboronic acid (140 mg, 0.72 mmol). Yield 100 mg (45%).

(b) 2-Carboxymethyl-5-(3,5-dichlorophenoxy)-1-(4-trifluoromethoxyphenyl)indole-3-carboxylic acid The title compound was prepared in accordance with step (d) Example 2 from 2-ethoxycarbonylmethyl-5-(3,5-dichlorophenoxy)-1-(4-trifluoromethoxyphenyl)indole-3-carboxylic acid ethyl ester (100 mg, 0.17 mmol, see step (a) above). Yield 35 mg (38%), mp 219-223° C.
200 MHz $^1$H-NMR (DMSO-d$_6$), δ: 3.95 (s, 2H); 6.94-7.16 (m, 4H); 7.31 (s, 1H); 7.59-7.74 (m, 4H); 7.78 (s, 1H); 12.0-14.4 (br s, 2H).

Example 56

2-Carboxymethyl-5-(4-chlorophenoxy)-1-(4-isopropylphenyl)indole-3-carboxylic acid (a) 2-Ethoxycarbonylmethyl-5-(4-chlorophenoxy)-1-(4-isopropylphenyl)indole-3-carboxylic acid ethyl ester The sub-title compound was prepared in accordance with step (c) Example 1 from 2-ethoxycarbonylmethyl-5-hydroxy-1-(4-isopropylphenyl)indole-3-carboxylic acid ethyl ester (150 mg, 0.37 mmol, see step (b) Example 10) and 4-chlorophenylboronic acid (116 mg, 0.74 mmol). Yield 150 mg (79%).

(b) 2-Carboxymethyl-5-(4-chlorophenoxy)-1-(4-isopropylphenyl)indole-3-carboxylic acid The title compound was prepared in accordance with step (d) Example 2 from 2-ethoxycarbonylmethyl-5-(4-chlorophenoxy)-1-(4-isopropylphenyl)indole-3-carboxylic acid ethyl ester (150 mg, 0.29 mmol, see step (a) above). Yield 78 mg (60%), mp 174-180° C.

200 MHz $^1$H-NMR (CDCl$_3$), δ: 1.28 (d, J=6.8 Hz, 6H); 3.03 (heptet, J=6.8 Hz, 1H); 3.90 (s, 2H); 6.87-7.11 (m, 4H); 7.29-7.44 (m, 4H); 7.46-7.58 (m, 2H); 7.70 (s, 1H); 11.9-14.0 (br s, 2H).

Example 57

2-Carboxymethyl-5-(3-chlorophenoxy)-1-(4-isopropylphenyl)indole-3-carboxylic acid (a) 2-Ethoxycarbonylmethyl-5-(3-chlorophenoxy)-1-(4-isopropylphenyl)indole-3-carboxylic acid ethyl ester The sub-title compound was prepared in accordance with step (c) Example 1 from 2-ethoxycarbonylmethyl-5-hydroxy-1-(4-isopropylphenyl)indole-3-carboxylic acid ethyl ester (150 mg, 0.37 mmol, see step (b) Example 10) and 3-chlorophenylboronic acid (116 mg, 0.74 mmol). Yield 130 mg (68%).

(b) 2-Carboxymethyl-5-(3-chlorophenoxy)-1-(4-isopropylphenyl)indole-3-carboxylic acid The title compound was prepared in accordance with step (d) Example 2 from 2-ethoxycarbonylmethyl-5-(3-chlorophenoxy)-1-(4-isopropylphenyl)indole-3-carboxylic acid ethyl ester (130 mg, 0.25 mmol, see step (a) above). Yield 67 mg (58%), mp 176-182° C.

200 MHz $^1$H-NM (CDCl$_3$), δ: 1.29 (d, J=6.6 Hz, 6H); 3.04 (heptet, J=6.6 Hz, 1H); 3.88 (s, 2H); 6.84-7.08 (m, 4H); 7.13 (d, J=7.8 Hz, 1H); 7.28-7.44 (m, 3H); 7.45-7.59 (m, 2H); 7.74 (s, 1H); 11.7-14.2 (br s, 2H).

Example 58

2-Carboxymethyl-5-(3,4-dichlorophenoxy)-1-(4-isopropyl-phenyl)indole-3-carboxylic acid (a) 5-(3,4-Dichlorophenoxy)-2-ethoxycarbonylmethyl-1-(4-isopropylphenyl indole-3-carboxylic acid ethyl ester The sub-title compound was prepared in accordance with step (c) Example 1 from 2-ethoxycarbonylmethyl-5-hydroxy-1-(4-isopropylphenyl)indole-3-carboxylic acid ethyl ester (150 mg, 0.37 mmol, see step (b) Example 10) and 3,4-dichlorophenylboronic acid (140 mg, 0.74 mmol). Yield 110 mg (55%).

(b) 2-Carboxymethyl-5-(3,4-dichlorophenoxy)-1-(4-isopropylphenyl)indole-3-carboxylic acid The title compound was prepared in accordance with step (d) Example 2 from 5-(3,4-dichlorophenoxy)-2-ethoxycarbonylmethyl-1-(4-isopropylphenyl)indole-3-carboxylic acid ethyl ester (110 mg, 0.20 mmol, see step (a) above). Yield 73 mg (74%), mp 174-180° C.

200 MHz $^1$H-NMR (CDCl$_3$), δ: 1.29 (d, J=6.8 Hz, 6H); 3.04 (heptet, J=6.8 Hz, 1H); 3.81 (s, 2H); 6.95 (dd, J=9.0 Hz, 2H); 7.04 (d, J=8.8 Hz, 1H); 7.22 (d, 1H); 7.33-7.44 (m, 2H); 7.46-7.64 (m, 3H); 7.76 (d, 1H); 11.6-14.2 (br s, 2H).

Example 59

2-Carboxymethyl-1-(4-isopropylphenyl)-5-(3-trifluoromethylphenoxy)-indole-3-carboxylic acid (a) 2-Ethoxycarbonylmethyl-1-(4-isopropylphenyl)-5-(3-trifluoromethylphenoxy)indole-3-carboxylic acid ethyl ester The sub-title compound was prepared in accordance with step (c) Example 1 from 2-ethoxycarbonylmethyl-5-hydroxy-1-(4-isopropylphenyl)indole-3-carboxylic acid ethyl ester (150 mg, 0.37 mmol, see step (b) Example 10) and 3-trifluoromethylphenylboronic acid (140 mg, 0.74 mmol), pyridine. Yield 130 mg (65%).

(b) 2-Carboxymethyl-1-(4-isopropylphenyl)-5-(3-trifluoromethylphenoxy)indole-3-carboxylic acid The title compound was prepared in accordance with step (d) Example 2 from 2-ethoxycarbonylmethyl-1-(4-isopropylphenyl)-5-(3-trifluoromethylphenoxy)indole-3-carboxylic acid ethyl ester (130 mg, 0.23 mmol, see step (a) above). Yield 60 mg (67%), mp 185-190° C.

200 MHz $^1$H-NMR (CDCl$_3$), δ: 1.29 (d, J=6.8 Hz, 6H); 3.04 (heptet, J=6.8 Hz, 1H); 3.84 (s, 2H); 6.97 (dd, J=8.8 and 2.2 Hz, 1H); 7.05 (d, J=8.8 Hz, 1H); 7.19-7.29 (m, 2H); 7.34-7.46 (m, 3H); 7.47-7.63 (m, 3H); 7.77 (d, J=2.0 Hz, 1H); 12.0-14.0 (br s, 9H).

Example 60

2-Carboxymethyl-5-(4-isopropoxyphenoxy)-1-(4-isopropylphenyl)indole-3-carboxylic acid (a) 2-Ethoxycarbonylmethyl-1-(4-isopropylphenyl)-5-(4-isopropoxyphenoxy)indole-3-carboxylic acid ethyl ester The sub-title compound was prepared in accordance with step (c) Example 1 from 2-ethoxycarbonylmethyl-5-hydroxy-1-(4-isopropylphenyl)indole-3-carboxylic acid ethyl ester (150 mg, 0.37 mmol, see step (b) Example 10) and 4-isopropoxyphenylboronic acid (130 mg, 0.74 mmol). Yield 100 mg (50%).

(b) 2-Carboxymethyl-5-(4-isopropoxyphenoxy)-1-(4-isopropylphenyl)indole-3-carboxylic acid The title compound was prepared in accordance with step (d) Example 2 from 2-ethoxycarbonylmethyl-1-(4-isopropylphenyl)-5-(4-isopropoxyphenoxy)indole-3-carboxylic acid ethyl ester (100 mg, 0.18 mmol, see step (a) above). Yield 51 mg (56%), mp 205-210° C.

200 MHz $^1$H-NMR (DMSO-d$_6$), δ: (DMSO-D$_6$, HMDSO), δ: 1.25 (d, J=6.0 Hz, 6H); 1.28 (d, J=6.9 Hz, 6H); 3.03 (heptet, J=6.9 Hz, 1H); 3.93 (s, 2H); 4.52 (heptet, J=6.0 Hz, 1H); 6.84-6.94 (m, 5H); 6.98 (d, J=8.7 Hz, 1H); 7.30-7.40 (m, 2H); 7.46-7.56 (m, 2H); 7.61 (d, J=1.9 Hz, 1H); 11.8-13.2 (br s, 2H).

Example 61

2-(4-Carboxyphenyl)-5-(3-chlorophenoxy)-1-(4-isopropoxyphenyl)indole-3-carboxylic acid (a) 5-(3-Chlorophenoxy)-1-(4-isopropoxyphenyl)-2-(4-methoxycarbonylphenyl indole-3-carboxylic acid methyl ester The sub-title compound was prepared in accordance with step (c) Example 1 from 5-hydroxy-1-(4-isopropoxyphenyl)-

2-(4-methoxycarbonylphenyl)indole-3-carboxylic acid methyl ester (150 mg, 0.32 mmol, see step (b) Example 43) and 3-chloro-phenylboronic acid (100 mg, 0.64 mmol. Yield 97 mg (54%).

(b) 2-(4-Carboxyphenyl)-5-(3-chlorophenoxy)-1-(4-isopropoxyphenyl)indole-3-carboxylic acid The title compound was prepared in accordance with step (d) Example 2 from 5-(3-chlorophenoxy)-1-(4-isopropoxyphenyl)-2-(4-methoxycarbonylphenyl)indole-3-carboxylic acid methyl ester (97 mg, 0.17 mmol, see step (a) above). Yield 61 mg (66%), mp 211-217° C.

200 MHz $^1$H-NMR (DMSO-$d_6$), δ: 1.24 (d, J=5.8 Hz, 6H); 4.60 (heptet, J=5.8 Hz, 1H); 6.86-7.09 (m, 5H); 7.09-7.28 (m, 4H); 7.37 (d, J=8.0 Hz, 1H); 7.41-7.52 (m, 2H); 7.76-7.90 (m, 3H).

Example 62

2-(4-Carboxyphenyl)-5-(4-chlorophenoxy)-1-(4-isopropoxyphenyl)indole-3-carboxylic acid (a) 5-(4-Chlorophenoxy)-1-(4-isopropoxyphenyl)-2-(4-methoxycarbonylphenyl)indole-3-carboxylic acid methyl ester The sub-title compound was prepared in accordance with step (c) Example 1 from 5-hydroxy-1-(4-isopropoxyphenyl)-2-(4-methoxycarbonylphenyl)indole-3-carboxylic acid methyl ester (150 mg, 0.32 mmol, see step (b) Example 43) and 4-chlorophenylboronic acid (100 mg, 0.64 mmol. Yield 97 mg (54%).

(b) 2-(4-Carboxyphenyl)-5-(4-chlorophenoxy)-1-(4-isopropoxyphenyl)indole-3-carboxylic acid The title compound was prepared in accordance with step (d) Example 2 from 5-(4-chlorophenoxy)-1-(4-isopropoxyphenyl)-2-(4-methoxycarbonylphenyl)indole-3-carboxylic acid methyl ester (97 mg, 0.17 mmol, see step (a) above). Yield 73 mg (79%), mp 217-222° C.

200 MHz $^1$H-NMR (DMSO-$d_6$), δ: 1.24 (d, J=5.8 Hz, 6H); 4.60 (heptet, J=5.8 Hz, 1H); 6.83-7.07 (m, 5H); 7.08-7.28 (m, 3H); 7.34-7.55 (m, 4H); 7.74-7.92 (m, 3H).

Example 63

2-(4-Carboxyphenyl)-5-(3,4-dichlorophenoxy)-1-(4-isopropoxyphenyl)indole-3-carboxylic acid (a) 5-(3,4-Dichlorophenoxy)-1-(4-isopropoxyphenyl)-2-(4-methoxycarbonylphenyl)indole-3-carboxylic acid methyl ester The sub-title compound was prepared in accordance with step (c) Example 1 from 5-hydroxy-1-(4-isopropoxyphenyl)-2-(4-methoxycarbonylphenyl)indole-3-carboxylic acid methyl ester (150 mg, 0.32 mmol, see step (b) Example 43) and 3,4-dichlorophenylboronic acid (120 mg, 0.64 mmol). Yield 60 mg (32%).

(b) 2-(4-Carboxyphenyl)-5-(3,4-dichlorophenoxy)-1-(4-isopropoxyphenyl)indole-3-carboxylic acid The title compound was prepared in accordance with step (d) Example 2 from 5-(3,4-dichlorophenoxy)-1-(4-isopropoxyphenyl)-2-(4-methoxycarbonylphenyl)indole-3-carboxylic acid methyl ester (60 mg, 0.10 mmol, see step (a) above). Yield 45 mg (79%), nip 199-203° C.

200 MHz $^1$H-NMR (DMSO-$d_6$), δ: 1.24 (d, J=5.8 Hz, 6H); 4.60 (heptet, J=5.8 Hz, 1H); 6.85-7.17 (m, 5H); 7.18-7.30 (m, 3H); 7.39-7.51 (m, 2H); 7.61 (d, J=8.9 Hz, 1H); 7.77-7.91 (m, 3H).

Example 64

5-(3-Carbamoylpyridin-2-yl-oxy )-2-carboxymethyl-1-(4-trifluoromethoxyphenyl)indole-3-carboxylic acid ethyl ester (a) 5-(3-Carbamoylpyridin-2-yl-oxy)-2-ethoxycarbonylmethyl-1-(4-trifluoromethoxyphenyl)indole-3-carboxylic acid ethyl ester The sub-title compound was prepared in accordance with step (a) Example 21 from 2-ethoxycarbonylmethyl-5-hydroxy-1-(4-trifluoromethoxyphenyl)indole-3-carboxylic acid ethyl ester (95 mg, 0.21 mmol, see (b) Example 9) and 2-chloro-nicotinamide (34 mg, 0.22 mmol). Yield 102 mg (85%).

(b) 5-(3-Carbamoylpyridin-2-yloxy)-2-carboxymethyl-1-(4-trifluoromethoxyphenyl)indole-3-carboxylic acid ethyl ester A mixture of 5-(3-carbamoylpyridin-2-yl-oxy)-2-ethoxycarbonylmethyl-1-(4-trifluoromethoxy-phenyl)indole-3-carboxylic acid ethyl ester (86 mg, 0.15 mmol, see step (a) above), NaOH (aq, 1M, 0.45 mL), EtOH (1 mL) and $H_2O$ (1 mL) was stirred at 55° C. for 3 h, cooled, filtered through Celite® and acidified to pH 4 with HCl (aq, 2M). The solid was filtered off, washed with $H_2O$ and purified by chromatography and recrystallisation from EtOAc. Yield 36 mg (46%), mp 128-130° C.

200 MHz $^1$H-NMR (DMSO-$d_6$), δ: 1.42 (t, J=7.1 Hz, 3H); 4.02 (s, 2H); 4.46 (q, J=7.1 Hz, 2H); 6.82 (br s, 1H); 7.01 (dd, J=8.9, 2.1 Hz, 1H); 7.09 (d, J=9.0 Hz, 1H); 7.14 (dd, J=7.6 and 4.8 Hz, 1H); 7.39-7.53 (m, 4H); 7.93 (d J=2.1 Hz, 1H); 7.90 (br s, 1H); 8.23 (dd J=4.8, 1.9 Hz, 1H), 8.62 (dd, J=7.6, 1.9 Hz, 1H).

Example 65

5-(3-Carbamoylpyridin-2-yloxy)-2-carboxymethyl-1-(4-isopropoxyphenyl)indole-3-carboxylic acid ethyl ester a) 5-(3-Carbamoylpyridin-2-yloxy)-2-ethoxycarbonylmethyl-1-(4-isopropoxyphenyl)indole-3-carboxylic acid ethyl ester The sub-title compound was prepared in accordance with step (a) Example 21 from 2-ethoxycarbonylmethyl-5-hydroxy-1-(4-isopropoxyphenyl)indole-3-carboxylic acid ethyl ester (86 mg, 0.20 mmol, see (b) Example 12) and 2-chloronicotin-amide (47 mg, 0.30 mmol). Yield 63 mg (58%).

(b) 5-(3-Carbamoylpyridin-2-yloxy)-2-carboxymethyl-1-(4-isopropoxyphenyl)indole-3-carboxylic acid ethyl ester The title compound was prepared in accordance with step (b) Example 64 from 5-(3-carbamoylpyridin-2-yloxy)-2-carboxymethyl-1-(4-isopropoxy-phenyl)indole-3-carboxylic acid ethyl ester (86 mg, 0.15 mmol, see step (a) above). Yield 36 mg (46%), mp 210-212° C.

200 MHz $^1$H-NMR (DMSO-$d_6$), δ: 1.29 (s, 3H); 1.33 (d, J=6.0 Hz, 6H); 3.89 (s, 2H); 4.27 (q, J=7.1 Hz, 2H); 4.72 (heptet, J=6.0 Hz, 1H); 7.00 (s, 2H); 7.09-7.18 (m, 2H); 7.19 (dd, J=7.1, 5.1 Hz, 1H); 7.30-7.40 (m, 2H); 7.76-7.83 (m, 2H); 7.89 (s, 1H); 8.13 (s, 1H); 8.17 (d, J=4.6, 1.9 Hz, 1H).

Example 66

2-Carboxymethyl-5-(3-carboxypyridin-2-yloxy)-1-(4-isopropoxyphenyl)indole-3-carboxylic acid A mixture of 5-(3-carbamoylpyridin-2-yloxy)-2-ethoxycarbonylmethyl-1-(4-isopropoxyphenyl)indole-3-carboxylic acid ethyl ester (63 mg, 0.12 mmol, see step (a) Example 65), NaOH (aq, 2M, 0.35 mL) and EtOH (2 mL) was stirred at 90° C. for 8 h, concentrated, diluted with MeOH and filtered through Celite®. EtOAc was added to the filtrate which was cooled for 4 h at 5° C. The solid was collected and dissolved in H$_2$O. The mixture was acidified to pH 4 with HCl (aq, 2 M). The solid was filtered off and dried for 4 h at 60° C. to give the title compound. Yield 34 mg (60%), mp 212-214° C. after recrystallisation from EtOAc/MeOH.

200 MHz $^1$H-NMR (DMSO-$d_6$), δ: 1.33 (d, J=6.0 Hz, 6H); 3.92 (s, 2H); 4.73 (heptet, J=6.0 Hz, 1H); 6.88-7.03 (m, 2H); 7.09-7.23 (m, 3H); 7.29-7.38 (m, 2H); 7.72 (d, J=1.7 Hz, 1H); 8.18-8.26 (m, 2H); 12.0-13.6 (br s, 3H).

Example 67

1-(4-Cyclopentyloxyphenyl)-5-(4-trifluoromethylphenyl)indole-2,3-dicarboxylic acid 2-ethyl ester (a) 5-(4-Trifluoromethylphenyl)indole-2-carboxylic acid ethyl ester A mixture of 5-bromoindole-2-carboxylic acid ethyl ester (4.22 g, 16 mmol), 4-trifluoromethylphenylboronic acid (4.50 g, 24 mmol), K$_3$PO$_4$ (11.7 g, 55 mmol), Pd(OAc)$_2$ (176 mg, 0.78 mmol), tri-o-tolylphosphine (478 mg, 1.6 mmol), EtOH (20 mL) and toluene (90 mL) was stirred under argon for 20 min at rt, heated at 100° C. for 2 h, cooled and poured into NaHCO$_3$ (aq, sat). The mixture was extracted with EtOAc and the combined extracts were washed with H$_2$O and brine, dried (Na$_2$SO$_4$), concentrated and purified by chromatography to give the sub-title compound. Yield 3.91 g (75%).

(b) 3-Iodo-5-(4-trifluoromethylphenyl)indole-2-carboxylic acid ethyl ester

NaI (2.04 g, 14 mmol) in acetone (10 mL) was added dropwise to a stirred solution of N-chlorosuccinimide (1.83 g, 14 mmol) in acetone (10 mL) protected from light. After 15 min, a solution of 5-(4-trifluoromethylphenyl)indole-2-carboxylic acid ethyl ester (3.80 g, 11 mmol; see step (a) above) in acetone (60 mL) was added dropwise, followed by stirring for 2 h at rt. The mixture was poured into Na$_2$S$_2$O$_3$ (aq, 10%, 250 mL) and extracted with EtOAc (200 mL). The combined extracts were washed with NaHCO$_3$ (aq, sat), water and brine, dried (Na$_2$SO$_4$) and concentrated. The residue was treated with petroleum ether to give the sub-title compound. Yield 4.88 g (93%).

(c) 1-(4-Cyclopentyloxyphenyl)-3-iodo-5-(4-trifluoromethylphenyl)indole-9-carboxylic acid ethyl ester Anhydrous CH$_2$Cl$_2$ (110 mL), Et$_3$N (2.45 mL, 17.4 mmol) and pyridine (1.42 mL, 17.4 mmol) were added to 3-iodo-5-(4-trifluoromethylphenyl)indole-2-carboxylic acid ethyl ester (4.00 g, 8.72 mmol; see step (b) above), Cu(OAc)$_2$ (3.16 g, 17.4 mmol), 3 Å molecular sieves (ca. 8 g) and 4-cyclopentyloxyphenylboronic acid (3.59 g, 17.48 mmol). The mixture was stirred vigorously at rt for 120 h and filtered through Celite®. The solids were washed with EtOAc, and the combined filtrates concentrated and purified by chromatography to afford the sub-title compound (3.83 g, 71%).

(d) 1-(4-Cyclopentyloxyphenyl)-5-(4-trifluoromethylphenyl)indole-2,3-dicarboxylic acid 2-ethyl ester 1-(4-Cyclopentyloxyphenyl)-3-iodo-5-(4-trifluoromethylphenyl)indole-2-carboxylic acid ethyl ester (310 mg, 0.5 mmol; see step (c) above) in THF (2 mL) was added dropwise to i-PrMgCl.LiCl (1.0 M in THF, 500 µL, 0.5 mmol) at −40° C. After 15 min at −40° C., a stream of dry CO$_2$ was passed through the mixture for 5 min and the mixture was allowed to warm to rt. The mixture was partitioned between EtOAc (10 mL) and NH$_4$Cl (aq, sat). The phases were separated and the aqueous layer was extracted with EtOAc. The combined organic phases were washed with H$_2$O and brine, dried (Na$_2$SO$_4$) concentrated and purified by chromatography, followed by recrystallisation from EtOAc/petroleum ether to give the title compound. Yield 70 mg (26%).

200 MHz $^1$H-NMR (DMSO-$d_6$), δ: 1.04 (t, J=7.0 Hz, 3H); 1.56-1.98 (m, 8H); 4.17 (q, J=7.0 Hz, 2H); 4.84-4.92 (m, 1H); 7.05-7.13 (m, 2H); 7.28 (d, J=8.8 Hz, 1H); 7.34-7.42 (m, 2H); 7.67 (dd, J=8.8, 1.8 Hz, 1H); 7.79-7.84 (m, 2H); 7.87-7.92 (m, 2H); 8.38 (d, J=1.4 Hz, 1H); 12.7-13.0 (br s, 1H).

Example 68

1-(4-Isopropoxyphenyl)-5-(5-trifluoromethylpyridin-2-yl)indole-2,3-dicarboxylic acid (a) 5-Bromo-3-iodoindole-2-carboxylic acid ethyl ester The sub-title compound was prepared in accordance with step (b) Example 67 from 5-bromoindole-2-carboxylic acid ethyl ester (10.0 g, 37.3 mmol) followed by recrystallisation from EtOAc/petroleum ether. Yield 13.5 g (92%).

(b) 5-Bromo-3-iodo-1-(4-isopropoxyphenyl)indole-2-carboxylic acid ethyl ester

The sub-title compound was prepared in accordance with step (b) Example I from 5-bromo-3-iodoindole-2-carboxylic acid ethyl ester (see step (a) above) and 4-isopropoxyphenylboronic acid.

(c) 5-Bromo-1-(4-isopropoxyphenyl)indole-2,3-dicarboxylic acid diethyl ester

5-Bromo-3-iodo-1-(4-isopropoxyphenyl)indole-2-carboxylic acid ethyl ester (1.0 g, 1.89 mmol; see step (b) above) in anhydrous DMPU (4 mL) was rapidly added to i-PrMgCl-.LiCl (1.0 M in THF, 4.2 mmol, 4.2 mL) at −65° C. After 30 min at −65° C., ethyl chloroformate (720 mL, 7.56 mmol) was added and the mixture was allowed to warm to rt and poured into NH$_4$Cl (aq, sat, 200 mL). The mixture was extracted with EtOAc (3×50 ml-L) and the combined extracts were washed with brine, dried (Na$_2$SO$_4$), concentrated and purified by chromatography to afford the sub-title compound. Yield 650 mg (72%).

(d) 1-(4-Isopropoxyphenyl)-5-(5-trifluoromethylpyridin-2-yl)indole-2,3-dicarb-oxylic acid diethyl ester hydrochloric salt t-BuLi (1.5 M in pentane, 4.5 mL, 3 mmol) was added dropwise at −78° C. to Et$_2$O (15 mL). 2-Bromo-5-trifluoromethylpyridine (762 mg, 3.37 mmol) in Et$_2$O (5 mL) was added via syringe. After 20 min at −78° C. the cold mixture was cannulated to cooled (−78° C.) ZnCl$_2$ (1 M in Et$_2$O, 7.4 mL, 7.4 mmol). The mixture was allowed to warm to rt and was stirred at rt for 3 h. The mixture was diluted with THF (15 mL) and added to a mixture of 5-bromo-1-(4-isopropoxyphenyl)indole-2,3-dicarboxylic acid diethyl ester (800 mg 1.69 mmol, see step (c) above), Pd(dppf)Cl$_2$ (165 mg, 0.20 mmol), CuI (77 mg, 0.40 mmol) and NT-methylpyrrolidin-2-one (5.3 mL). The mixture was heated at 80° C. for 6 h, poured into NH$_4$Cl (aq, sat, 50 mL) and extracted with t-BuOMe (3×30 mL). The combined extracts were washed with brine, dried (Na$_2$SO$_4$) and filtered through Celite®. The solids were washed with t-BuOMe and the combined filtrates were concentrated. The residue was dissolved in anhydrous Et$_2$O and HCl (4 M in dioxane, 500 μL, 2.0 mmol) was added. After 10 min the mixture was concentrated and the residue was treated with anhydrous Et$_2$O to give the sub-title compound. Yield 900 mg (92%).

(e) 1-(4-Isopropoxyphenyl)-5-(5-trifluoromethylpyridin-2-yl)indole-2,3-dicarb-oxylic acid A mixture of 1-(4-isopropoxyphenyl)-5-(5-trifluoromethylpyridin-2-yl)indole-2,3-dicarboxylic acid diethyl ester hydrochloric salt (150 mg, 0.26 mmol, see step (d) above), NaOH (aq, 2 M, 2 mL) and dioxane (3) mL) was heated at 80° C. for 4 h. After cooling, the reaction mixture was acidified with HCl (aq, IM) to pH 5 and filtered. The solid was recrystallised from EtOAc/petroleum ether to afford the title compound. Yield 96 mg (76%).

200 MHz $^1$H-NMR (DMSO-d$_6$), δ: 1.31 (d, J=6.0 Hz, 6H); 4.69 (heptet, J=6.0 Hz, 1H); 7.05-7.14 (m, 2H); 7.22 (d, J=8.9 Hz, 1H); 7.32-7.41 (m, 2H); 8.08 (dd, J=8.9 and 1.6 Hz, 1H); 8.16 (d, J=8.6 Hz, 111); 8.25 (dd, J=8.6 and 2.0 Hz, 1H); 8.98 (d, J=1.1 Hz, 1H); 9.04 (s, 1H).

Example 69

2-Carboxymethyl-5-(3-chlorophenoxy)-1-phenylindole-3-carboxylic acid (a) 5-(3-Chlorophenoxy)-2-ethoxycarbonylmethyl-1-phenylindole-3-carboxylic acid ethyl ester The sub-title compound was prepared in accordance with step (c) Example 1 from 2-ethoxycarbonylmethyl-5-hydroxy-1-phenylindole-3-carboxylic acid ethyl ester (140 mg, 0.38 mmol, see step (b) Example 3) and 3-chlorophenylboronic acid (119 mg, 0.76 mmol). Yield 53 mg (29%).

(b) 2-Carboxymethyl-5-(3-chlorophenoxy)-1-phenylindole-3-carboxylic acid

The title compound was prepared in accordance with step (d) Example 2 from 5-(3-chlorophenoxy)-2-ethoxycarbonylmethyl-1-phenylindole-3-carboxylic acid ethyl ester (45 mg, 0.094 mmol, see step (a) above). Yield 29 mg (73%), mp 192-194° C. (recrystallized from CHCl$_3$)

200 MHz $^1$H-NMR (DMSO-d$_6$), δ: 3.98 (s, 2H); 6.88-7.18 (m, 5H); 7.31-7.53 (m, 3H); 7.56-7.70 (m, 3H); 7.73 (d, J=1.8 Hz, 1H); 11.5-13.5 (br s, 2H).

Example 70

2-Carboxymethyl-5-(4-chlorophenoxy)-1-phenylindole-3-carboxylic acid (a) 5-(4-Chlorophenoxy)-2-ethoxycarbonylmethyl-1-phenylindole-3-carboxy-lic acid ethyl ester The sub-title compound was prepared in accordance with step (c) Example 1 from 2-ethoxycarbonylmethyl-5-hydroxy-1-phenylindole-3-carboxylic acid ethyl ester (140 mg, 0.38 mmol, see step (b) Example 3) and 4-chlorophenylboronic acid (119 mg, 0.76 mmol). Yield 100 mg, 55%.

(b) 2-Carboxymethyl-5-(4-chlorophenoxy)-1-phenylindole-3-carboxylic acid

The title compound was prepared in accordance with step (d) Example 2 from 5-(4-chlorophenoxy)-2-ethoxycarbonylmethyl-1-phenylindole-3-carboxylic acid ethyl ester (45 mg, 0.094 mmol, see step (a) above). Yield 22 mg (56%), mp 202-204° C.

200 MHz $^1$H-NMR (DMSO-d$_6$), δ: 3.96 (s, 2H); 6.92-7.07 (m, 4H); 7.33-7.49 (m, 4H); 7.56-7.69 (m, 3H); 7.71 (d, J=2.2 Hz, 1H); 11.0-14.0 (br s, 2H).

Example 71

2-Carboxymethyl-5-(3-chloro-4-fluorophenoxy)-1-phenylindole-3-carboxylic acid (a) 5-(3-Fluoro-4-chlorophenoxy)-2-ethoxycarbonylmethyl-1-phenylindole-3-carboxylic acid ethyl ester The sub-title compound was prepared in accordance with step (c) Example 1 from 2-ethoxycarbonylmethyl-5-hydroxy-1-phenylindole-3-carboxylic acid ethyl ester (140 mg, 0.38 mmol, see step (b) Example 3) and 3-fluoro-4-chlorophenylboronic acid (133 mg, 0.76 mmol). Yield 103 mg (54%).

(b) 2-Carboxymethyl-5-(3-fluoro-4-chlorophenoxy)-1-phenylindole-3-carboxylic acid The title compound was prepared in accordance with step (d) Example 2 from 5-(3-fluoro-4-chlorophenoxy)-2-ethoxycarbonylmethyl-1-phenylindole-3-carboxylic acid ethyl ester (103 mg, 0.208 mmol, see step (a) above). Yield 28 mg (31%), mp 174-176° C.

200 MHz $^1$H-NMR (DMSO-d$_6$), δ: 3.78 (s, 2H); 6.89-7.06 (m, 3H); 7.19 (dd, J=6.1, 2.9 Hz, 1H); 7.32-7.51 (m, 3H); 7.54-7.71 (m, 3H); 7.73 (d, J=2.0 Hz, 1H).

Example 72

2-Carboxymethyl-1-(3-chlorophenyl)-5-(3-trifluoromethoxyphenoxy)indole-3-carboxylic acid (a) 1-(3-chlorophenyl)-2-ethoxycarbonylmethyl-5-(3-trifluoromethylphenoxy)indole-3-carboxylic acid ethyl ester The sub-title compound was prepared in accordance with step (c) Example 1 from 1-(3-chlorophenyl)-2-ethoxycarbonylmethyl-5-hydroxyindole-3-carboxylic acid ethyl ester (135 mg, 0.34 mmol, see step (b) Example 8) and 3-trifluoromethylphenylboronic acid (96 mg, 0.50 mmol). Yield 110 mg (60%).

(b) 9-Carboxymethyl-5-(3-trifluoromethylphenoxy)-1-(3-chlorophenyl)-indole-3-carboxylic acid The title compound was prepared in accordance with step (c) Example 40 from 1-(3-chlorophenyl)-2-ethoxycarbonylmethyl-5-(3-trifluoromethylphenoxy)-indole-3-carboxylic acid ethyl ester (100 mg, 0.18 mmol, see step (a) above). Yield 62 mg (69%), mp 210-212° C.
200 MHz $^1$H-NMR (DMSO-d$_6$), δ: 3.88-4.17 (m, 2H); 6.95 (dd, J=8.8, 1.9 Hz, 1H); 7.00-7.18 (m, 3H); 7.26-7.61 (m, 6H); 7.93 (d, J=1.9 Hz, 1H).

Example 73

2-Carboxymethyl-5-(4-chlorophenoxy)-1-(4-diethylaminophenyl)indole-3-carboxylic acid (a) 5-(4-Chlorophenoxy)-1-(4-diethylaminophenyl)-2-ethoxycarbonylmethyl-indole-3-carboxylic acid ethyl ester The sub-title compound was prepared in accordance with step (c) Example 1 from 1-(4-diethylaminophenyl)-2-ethoxycarbonylmethyl-5-hydroxyindole-3-carboxylic acid ethyl ester (150 mg, 0.35 mmol, see step (b) Example 1) and 4-chlorophenylboronic acid (83 mg, 0.53 mmol). Yield 107 mg (57%).

(b) 2-Carboxymethyl-5-(4-chlorophenoxy-1-(4-diethylaminophenyl)indole-3-carboxylic acid The title compound was prepared in accordance with step (d) Example 2 from 5-(4-chlorophenoxy)-1-(4-diethylaminophenyl)-2-ethoxycarbonylmethylindole-3-carboxylic acid ethyl ester (107 mg, 0.20 mmol, see step (a) above). Yield 90 mg (89%), mp 210° C.
200 MHz $^1$H-NMR (DMSO-d$_6$), δ: 1.14 (t, J=6.7 Hz, 6H); 3.41 (q, J=6.7 Hz, 4H, overlapped with DMSO and water); 3.93 (s, 2H); 6.75-6.87 (m, 2H); 6.88-7.07 (m, 4H); 7.09-7.21 (m, 2H); 7.32-7.43 (m, 2H); 7.68 (d, J=2.0 Hz, 1H); 12.1-12.6 (br s, 2H).

Example 74

2-Carboxymethyl-1-(4-diethylaminophenyl)-5-(2-naphthyloxy))indole-3-carboxylic acid (a) 1-(4-Diethylaminophenyl)-5-(2-naphthyloxy)-2-ethoxycarbonylmethylindole-3-carboxylic acid ethyl ester The sub-title compound was prepared in accordance with step (c) Example 1 from 1-(4-diethylaminophenyl)-2-ethoxycarbonylmethyl-5-hydroxyindole-3-carboxylic acid ethyl ester (150 mg, 0.35 mmol, see step (b) Example 1) and 2-naphthyl-boronic acid (91 mg, 0.53 mmol). Yield 66 mg, (34%).

(b) 2-Carboxymethyl-1-(4-diethylaminophenyl)-5-(2-naphthyloxy))indole-3-carboxylic acid The title compound was prepared in accordance with step (d) Example 2 from 1-(4-diethylaminophenyl)-5-(2-naphthyloxy)-2-ethoxycarbonylmethylindole-3-carboxylic acid ethyl ester (107 mg, 0.20 mmol, see step (a) above). Yield 50 mg (79%), mp 210° C.
200 MHz $^1$H-NMR (DMSO-d$_6$), δ: 1.14 (t, J=6.7 Hz, 6H); 3.41 (q, J=6.7 Hz, 4H, overlapped with DMSO and water); 3.93 (s, 2H); 6.75-6.87 (m, 2H); 6.88-7.07 (m, 4H); 7.09-7.21 (m, 2H); 7.32-7.43 (m, 2H); 7.68 (d, J=2.0 Hz, 1H); 12.1-12.6 (br s, 2H).

Example 75

1-(4-Diethylaminophenyl)-2-ethoxycarbonylmethyl-5-(4-trifluoromethoxyphenoxy)indole-3-carboxylic acid ethyl ester (a) 1-(4-Diethylaminophenyl)-2-ethoxycarbonylmethyl-5-(4-trifluoromethoxyphenoxy)indole-3-carboxylic acid ethyl ester The sub-title compound was prepared in accordance with step (c) Example 1 from 1-(4-diethylaminophenyl)-2-ethoxycarbonylmethyl-5-hydroxyindole-3-carboxylic acid ethyl ester (438 mg, 1 mmol, see step (b) Example 1) and 4-trifluoro-methoxybenzeneboronic acid (347 mg, 1.3 mmol). Yield 400 mg (67%).
200 MHz $^1$H-NMR (CDCl$_3$; TMS), δ: 1.16-1.29 (m, 9H); 1.35 (t, J=7.1 Hz, 3H); 3.43 (q, J=7.1 Hz, 4H); 4.06 (s, 2H); 4.13 (q; J=7.1 Hz, 2H): 4.35 (q, J=7.0 Hz, 2H); 6.66-6.80 (m, 2H); 6.90 (dd, J=8.8, 2.2 Hz, 1H); 6.94-7.09 (m, 3H); 7.10-7.21 (m, 4H); 7.83 (d, J=2.2 Hz, 1H).

(b) 2-Carboxymethyl-1-(4-diethylaminophenyl)-5-(4-trifluoromethoxyphenoxy)-indole-3-carboxylic acid The title compound was prepared in accordance with step (d) Example 2 from 1-(4-diethylaminophenyl)-2-ethoxycarbonylmethyl-5-(4-trifluoro-methoxyphenoxy)indole-3-carboxylic acid ethyl ester (210 mg, 0.35 mmol, see step (a) above). Yield 101 mg (53%).
200 MHz $^1$H-NMR (DMSO-d$_6$) δ: 1.15 (t, J=6.8 Hz, 6H); 3.42 (q, J=6.8 Hz, 4H, overlapped with DMSO and water); 3.93 (s, 2H); 6.76-6.88 (m, 2H); 6.95 (dd, J=8.8, 2.2 Hz, 1H); 6.99-7.10 (m, 3H); 7.11-7.21 (m, 2H); 7.28-7.40 (m, 2H); 7.71 (d, J=2.2 Hz); 12.0-12.8 (br s, 2H).

Example 76

2-Carboxymethyl-1-(4-isopropylphenyl)-5-(4-trifluoromethylphenyl)indole-3-carboxylic acid (a) 2-Ethoxycarbonylmethyl-1-(4-isopropylphenyl)-5-trifluoromethanesulfonyl-oxyindole-3-carboxylic acid ethyl ester Pyridine (0.6 mL) was added to a solution of 2-ethoxycarbonylmethyl-5-hydroxy-1-(4-isopropylphenyl)indole-3-carboxylic acid ethyl ester (400 mg, 1.01 mmol, see step (b) Example 10) in CH$_2$Cl$_2$ (10 mL). The solution was cooled to 0° C. and trifluoromethanesulfonic anhydride was added. The reaction mixture was stirred at rt for 26 h. H$_2$O (50 mL) was added and the aqueous phase extracted with CH$_2$Cl$_2$. The extract was dried (Na$_2$SO$_4$), concentrated and purified by chromatography to give the sub-title compound Yield 477 mg (87%).

(b) 2-Ethoxycarbonylmethyl-1-(4-isopropylphenyl)-5-(4-trifluoromethylphenyl)indole-3-carboxylic acid ethyl ester A mixture 2-ethoxycarbonylmethyl-1-(4-isopropylphenyl)-5-trifluoromethane-sulfonyloxyindole-3-carboxylic acid ethyl ester (133 mg, 0.25 mmol, see step (a) above), 4-trifluoromethylphenylboronic acid (142 mg, 0.75 mmol), $K_2CO_3$ (276 mg, 2 mmol), tetrakis(triphenylphosphine)palladium(0) (78 mg, 0.067 mmol) and anhydrous dioxane (10 mL) was stirred at 90° C. for 4 h. The mixture was diluted with EtOAc (30 mL), washed with saturated $NaHCO_3$ (aq, sat) dried ($Na_2SO_4$), concentrated and purified by chromatography to give the sub-title compound. Yield 102 mg (76%).

(c) 2-Carboxymethyl-1-(4-isopropylphenyl)-5-(4-trifluoromethylphenyl)indole-3-carboxylic acid The title compound was prepared in accordance with step (d) Example 2 from 2-ethoxycarbonylmethyl-1-(4-isopropylphenyl)-5-(4-trifluoromethylphenyl)indole-3-carboxylic acid ethyl ester (100 mg, 0.19 mmol, see step (b) above). Yield 75 mg (81%).

200 MHz $^1$H-NMR (DMSO-$d_6$) δ: 1.30 (d, J=6.9 Hz, 6H); 3.05 (heptet, J=6.9 Hz, 1H); 3.98 (s, 2H); 7.10 (d, J=8.6 Hz, 1H); 7.33-7.43 (m, 2H); 7.49-7.61 (m, 3H); 7.78-7.94 (m, 4H); 8.41 (d, 1H); 12.3-12.7 (br s, 2H).

Example 77

2-Carboxymethyl-1-(4-diethylaminophenyl)-5-(4-trifluoromethoxyphenoxy)indole-3-carboxylic acid ethyl ester 1-(4-Diethylaminophenyl)-2-ethoxycarbonylmethyl-5-(4-trifluoromethoxyphenoxy)indole-3-carboxylic acid ethyl ester (150 mg, 0.25 mmol, see step (a) Example 75) was hydrolysed at 55° C. for 3 h with NaOH (aq, 2 M, 2 mL) and dioxane (2 mL). Work-up as described in step (d) Example 1 gave the title compound. Yield 110 mg (77%).

200 MHz $^1$H-NMR (CDCl$_3$), δ: 1.24 (t, J=7.0 Hz, 6H); 1.37 (t, J=7.1 Hz, 3H); 3.43 (q, J=7.0 Hz, 4H); 4.02 (s, 2H); 4.41 (q, J=7.1 Hz, 2H); 6.68-6.83 (m, 2H); 6.92 (dd, J=8.8, 2.2 Hz, 1H); 6.96-7.23 (m, 7H); 7.75 (d, J=2.2 Hz, 1H).

Example 78

1-(4-Diethylaminophenyl)-2-ethoxycarbonylmethyl-5-(4-trifluoromethoxyphenoxy)indole-3-carboxylic acid A mixture of 1-(4-diethylaminophenyl)-2-ethoxycarbonylmethyl-5-(4-trifluoromethoxyphenoxy)indole-3-carboxylic acid ethyl ester (63 mg, 0.12 mmol, see step (a) Example 75), HCl (aq, 1 M, 0.2 mL) and EtOH (1 mL) was heated at reflux for 2 h and cooled. The pH was adjusted to 4 by with NaOH (aq, 1 M) and the mixture was extracted with EtOAc. The organic layer was washed with brine, dried ($Na_2SO_4$), concentrated and purified by chromatography to give the title compound. Yield 61 mg (89%).

200 MHz $^1$H-NMR (CDCl$_3$), δ: 1.07-1.99 (m, 9H); 3.36 (q, JT 7.0 Hz, 4H); 4.02 (s, 2H); 4.07 (q, J=7.3 Hz, 2H); 6.59-6.76 (m, 2H); 6.78-6.95 (m, 3H); 6.97-7.17 (m, 5H); 7.87 (d, 1H)

Example 79

2-Carboxymethyl-1-(9-ethylcarbazol-yl)-5-(4-trifluoromethoxyphenoxy)indole-3-carboxylic acid (a) 1-(1-Ethylcarbazol-4-yl)-2-ethoxycarbonylmethyl-5-(4-trifluoromethoxyphenoxy)indole-3-carboxylic acid ethyl ester The sub-title compound was prepared in accordance with step (c) Example 1 from 2-ethoxycarbonylmethyl-1-(9-ethylcarbazol-3-yl)-5-hydroxyindole-3-carboxylic acid ethyl ester (150 mg, 0.31 mmol, see step (b) Example 14) and 4-trifluoromethoxyphenylboronic acid (130 mg, 0.62 mmol. Yield 100 mg (50%).

(b) 2-Carboxymethyl-1-(9-ethylcarbazol-yl)-5-(4-trifluoromethoxyphenoxy)indole-3-carboxylic acid The title compound was prepared in accordance with step (d) Example 2 from 2-carboxymethyl-1-(9-ethylcarbazol-yl)-5-(4-trifluoromethoxyphenoxy)indole-3-carboxylic acid ethyl ester (100 mg, 0.155 mmol, see step (a) above). Yield 62 mg (68%).

200 MHz $^1$H-NMR (DMSO-$d_6$), δ: 1.40 (t, J=6.9 Hz, 3H); 3.86 (s, 2H); 4.55 (q, J=6.9 Hz, 2H); 6.92 (dd, J=8.9, 2.0 Hz, 1H); 6.99-7.11 (m, 3H); 7.19-7.40 (m 3H); 7.42-7.59 (m, 2H); 7.71 (d, J=8.3 Hz, 1H); 7.79 (d, 1H); 7.85 (d, J=8.7 Hz, 1H); 8.19 (d, J 7. Hz, 1H); 8.27 (d, 1H).

Example 80

2-Carboxymethyl-1-(4-morpholin-1-yl-phenyl)-5-(4-trifluoromethoxyphenoxy)indole-3-carboxylic acid (a) 2-Ethoxycarbonylmethyl-1-(4-morpholin-1-yl-phenyl)-5-(4-trifluoromethoxyphenoxy)indole-3-carboxylic acid ethyl ester The sub-title compound was prepared in accordance with step (c) Example 1 from 2-ethoxycarbonylmethyl-5-hydroxy-1-(4-morpholin-1-yl-phenyl)indole-3-carboxylic acid ethyl ester (300 mg, 0.66 mmol, see step (b) Example 15) and 4-trifluoromethoxyphenylboronic acid (270 mg, 1.32 mmol). Yield 238 mg (59%).

(b) 2-Carboxymethyl-1-(4-morpholin-1-yl-phenyl)-5-(4-trifluoromethoxyphenoxy)indole-3-carboxylic acid The title compound was prepared in accordance with step (d) Example 2 from 2-ethoxycarbonylmethyl-1-(4-morpholin-1-yl-phenyl)-5-(4-trifluoromethoxyphenoxy)indole-3-carboxylic acid ethyl ester (230 mg, 0.375 mmol, see step (a) above). Yield 30 mg (14%), mp 185-190° C.

200 MHz $^1$H-NMR (DMSO-$d_6$), δ: 3.08-3.30 (m, 4H, overlapped with DMSO water); 3.65-3.86 (m, 6H); 6.84-7.08 (m, 4H); 7.08-7.19 (m, 2H); 7.21-7.39 (m, 4H); 7.76 (d, 1H).

Example 81

2-Carboxymethyl-1-(4-dimethylaminophenyl)-5-(4-trifluoromethoxyphenoxy)indole-3-carboxylic acid (a) 1-(4-Dimethylaminophenyl)-2-ethoxycarbonylmethyl-5-(4-trifluoromethoxyphenoxy)indole-3-carboxylic acid ethyl ester The sub-title compound was prepared in accordance with step (c) Example 1 from 1-(4-dimethylaminophenyl)-2- ethoxycarbonylmethyl-5-hydroxyindole-3-carboxylic acid ethyl ester (150 mg, 0.37 mmol, see step (b) Example 16) and 4-trifluoromethoxyphenylboronic acid (50 mg, 0.74 mmol). Yield 120 mg (57%).

(b) 2-Carboxymethyl-1-(4-dimethylaminophenyl)-5-(4-trifluoromethoxyphenoxy)indole-3-carboxylic acid The title compound was prepared in accordance with step (d) Example 2 from 1-(4-dimethylaminophenyl)-2-ethoxycarbonylmethyl-5-(4-trifluoromethoxyphenoxy)indole-3-carboxylic acid ethyl ester (120 mg, 0.21 mmol, see step (a) above). Yield 40 mg (37%), mp 188-192° C.
200 MHz $^1$H-NMR (DMSO-$d_6$), δ: 3.00 (m, 6H); 3.79 (s, 2H); 6.82-7.10 (m, 6H); 7.14-7.26 (m, 2H); 7.28-7.39 (m, 2H); 7.74 (d, 1H).

Example 82

2-Carboxymethyl-1-(3-chlorophenyl)-5-(4-isopropoxyphenoxy)indole-3-carboxylic acid (a) 1-(3-Chlorophenyl)-2-ethoxycarbonylmethyl-5-(4-isopropoxyphenoxy)indole 3-carboxylic acid ethyl ester The sub-title compound was prepared in accordance with step (c) Example 1 from 1-(3-chlorophenyl)-2-ethoxycarbonylmethyl-5-hydroxyindole-3-carboxylic acid ethyl ester (135 mg, 0.34 mmol, see step (b) Example 8) and 4-isopropoxyphenylboronic acid (91 mg, 0.50 mmol). Yield 70 mg (39%).

(b) 2-Carboxymethyl-1-(3-chlorophenyl)-5-(4-isopropoxyphenoxy)indole-3-carboxylic acid A mixture of 1-(3-chlorophenyl)-2-ethoxycarbonylmethyl-5-(4-isopropoxyphenoxy)indole-3-carboxylic acid ethyl ester (65 mg, 0.12 mmol, see step (a) above), NaOH (aq, 1 M, 15 mL), and EtOH (20 mL) was heated at 50° C. for 48 h and stirred at rt overnight and acidified to pH 4 with HCl (aq, 1 M) and extracted with $CH_2Cl_2$. The organic layer was washed with $H_2O$ and brine, dried ($Na_2SO_4$), concentrated and purified by chromatography. Yield 45 mg (78%), mp 188-190° C.
200 MHz $^1$H-NMR ($CDCl_3$), δ: 1.29 (d, J=6.1 Hz, 6H); 3.82-4.16 (m, 2H); 4.44 (heptet, J=6.1 Hz, 1H); 6.76-7.02 (m, 6H); 7.28-7.59 (m, 4H); 7.81 (s, 1H).

Example 83

2-Carboxymethyl-1-(4-piperidin-1-ylphenyl)-5-(4-trifluoromethoxyphenoxy)indole-3-carboxylic acid (a) 2-Ethoxycarbonylmethyl-1-(4-piperidin-1-ylphenyl)-5-(4-trifluoromethoxyphenoxy)indole-3-carboxylic acid ethyl ester The sub-title compound was prepared in accordance with step (c) Example 1 from 2-ethoxycarbonylmethyl-5-hydroxy-1-(4-piperidin-1-yl-phenyl)indole-3-carboxylic acid ethyl ester (300 mg, 0.66 mmol, see step (b) Example 17) and 4-trifluoromethoxyphenylboronic acid (270 mg, 1.32 mmol). Yield 257 mg (63%).

(b) 2-Carboxymethyl-1-(4-piperidin-1-ylphenyl)-5-(4-trifluoromethoxyphenoxy)indole-3-carboxylic acid The title compound was prepared in accordance with step (d) Example 2 from 2-ethoxycarbonylmethyl-1-(4-piperidin-1-ylphenyl)-5-(4-trifluoromethoxyphenoxy)indole-3-carboxylic acid ethyl ester (250 mg, 0.41 mmol, see step (a) above). Yield 30 mg, (13%), mp>200° C.
200 MHz $^1$H-NMR (DMSO-$d_6$), δ: 1.50-2.01 (m, 4H); 2.07-2.37 (m, 2H); 3.88-4.09 (m, 2H); 4.02 (s, 2H); 4.16-4.38 (m, 2H); 6.96-7.15 (m, 4H); 7.28-7.42 (m, 2H); 7.68-7.87 (m, 3H); 8.25-8.40 (m, 2H).

Example 84

2-Carboxymethyl-5-(4-chlorophenoxy)-1-(4-piperidin-1-yl-phenyl)indole-3'-carboxylic acid (a) 2-Ethoxycarbonylmethyl-5-(4-chlorophenoxy)-1-(4-piperidin-1-ylphenyl indole-3-carboxylic acid ethyl ester The sub-title compound was prepared in accordance with step (c) Example 1 from 2-ethoxycarbonylmethyl-5-hydroxy-1-(4-piperidin-1-yl-phenyl)indole-3-carboxylic acid ethyl ester (150 mg, 0.33 mmol, see step (b) Example 17) and 4-chlorophenylboronic acid (100 mg, 0.66 mmol). Yield 120 mg (63%).

(b) 2-Carboxymethyl-5-(4-chlorophenoxy)-1-(4-piperidin-1-yl-phenyl)indole-3-carboxylic acid The title compound was prepared in accordance with step (d) Example 2 from 2-ethoxycarbonylmethyl-5-(4-chlorophenoxy)-1-(4-piperidin-1-ylphenyl)indole-3-carboxylic acid ethyl ester (120 mg, 0.21 mmol, see step (a) above). Yield 50 mg (46%), mp 183-187° C.
200 MHz $^1$H-NMR (DMSO-$d_6$), δ: 1.50-1.77 (m, 6H); 3.19-3.54 (m, 4H); 3.76 (s, 2H); 6.89 (dd, J=8.9, 2.2 Hz, 1H), 6.93-7.04 (m, 3H); 7.05-7.15 (m, 2H); 7.17-7.27 (m, 2H); 7.32-7.43 (m, 2H); 7.71 (d, J=2.2 Hz, 1H).

Example 85

3-(2-Acetylamino-2-carboxyethyl)-1-(4-cyclopentyloxyphenyl)-5-(4-trifluoromethyl phenyl)indole-2-carboxylic acid (a) 3-(2-Acetylamino-1-(4-cyclopentyloxyphenyl)-2-ethoxycarbonylvinyl)-5-(4-trifluoromethylphenyl)indole-2-carboxylic acid ethyl ester A mixture 1-(4-cyclopentyloxyphenyl)-3-iodo-5-(4-trifluoromethylphenyl)indole-2-carboxylic acid ethyl ester (700 mg, 1.13 mmol; see step (c) Example 67), 2-acetylaminoacrylic acid ethyl ester (324 mg, 2.26 mmol), $PdCl_2(PPh_3)$ (39.6 mg, 0.056 mmol), NaOAc ('370 mg, 4.52 mmol), $Et_3N$ (0.22 ml, 1.6 mmol) and DMF (2.1 mL) was stirred for 2.1 h at 100° C. cooled and diluted with EtOAc. The mixture was washed with $NaHCO_3$ (aq, 5%), HCl (aq, 0.5 M), $H_2O$ and brine, dried ($N_2SO_4$), concentrated and purified by chromatography to give the sub-title compound. Yield 375 mg (52%)

(b) 3-(2-Acetylamino-1-(4-cyclopentyloxyphenyl)-2-ethoxycarbonylethyl)-5-(4-trifluoromethylphenyl)indole-2-carboxylic acid ethyl ester 3-(2-Acetylamino-1-(4-cyclopentyloxyphenyl)-2-ethoxycarbonylvinyl)-5-(4-trifluoromethylphenyl)indole-2-carboxylic acid ethyl ester ('370 mg-, 0.58 mmol; see step (b) above) in MeOH (15 mL) and THF (115 mL) was hydrogenated (rt, 7 bar) over Pd—C (10%, 300 mg) for 6.5 h. The mixture was filtered through Celite® and concentrated to give sub-title compound. Yield 378 mg (1100%)

(c) 3-(2-Acetylamino-2-carboxyethyl)-1-(4-cyclopentyloxyphenyl)-5-(4-trifluoromethylphenyl)indole-2-carboxylic acid A mixture of 3-(2-acetylamino-1-(4-cyclopentyloxyphenyl)-2-ethoxycarbonylethyl)-5-(4-trifluoromethylphenyl)indole-2-carboxylic acid ethyl ester (373 mg, 0.60 mmol; see step (b) above), NaOH (240 mg, 6 mmol) $H_2O$ (10 mL) and EtOH (14 ink) was heated at reflux for 3 h, cooled and acidified with HCl (aq, 1 M) to pH 2. The solid was collected and recrystallised from toluene/EtOH, affording the title compound. Yield 218 mg (62%).
200 MHz $^1$H-NMR (DMSO-$d_6$) δ 13.0-12.4 (2H, br s) 8.33 (1H, d, J=8.2 Hz) 8.19 (1H, d, J=1.5 Hz) 8.00-7.90 (2H, m) 7.85-7.75 (2H, m) 7.62 (1H, dd, J=8.8 1.5 Hz) 7.24-7.15 (2H, m) 7.07 (1H, d, J=8.8 Hz) 7.07-6.96 (2H, m) 4.92-4.80 (1H, m) 4.68-4.50 (1H, m) 3.67 (1H, dd, J=13.9, 6.2 Hz) 3.41-3.27 (1H, m) 2.06-1.50 (8H, m) 1.65 (3H, s).

Example 86

[5-(4-tert-Butylphenyl)-2-carboxy-1-(4-isopropoxyphenyl)indol-3-ylmethyl]-carboxymethylmethylammonium chloride (a) 5-Bromo-3-formylindole-2-carboxylic acid ethyl ester Oxalyl chloride (3.43 mL, 39.9 mmol) was added with stirring to DMF (30 mL) and $CH_2Cl_2$ (80 mL) at 0° C. After 20 min at 0° C., 5-bromoindole-2-carboxylic acid ethyl ester (10 g, 37.3 mmol) in DMF (80 mL), was added. The mixture was stirred at rt for 24 h and poured into $NaHCO_3$ (aq, sat) and extracted with $CH_2Cl_2$. The combined extracts were washed with $H_2O$ and brine, dried ($Na_2SO_4$) and concentrated. Crystallisation from EtOH gave the sub-title compound. Yield 8.9 g (81%).

(b) 5-Bromo-3-formyl-1-(4-isopropoxyphenyl)indole-2-carboxylic acid ethyl ester

The sub-title compound was prepared in accordance with step (c) Example 1 from 5-bromo-3-formylindole-2-carboxylic acid ethyl ester (4 g, 13.51 mmol; see step (a) above) and 4-isopropoxyphenylboronic acid (4.86 g, 27.02 mmol). Yield 4.1 g (710%).

(c) 5-(4-tert-Butylphenyl)-3-formyl-1-(4-isopropoxyphenyl)indole-2-carb-oxylic acid ethyl ester The sub-title compound was prepared in accordance with step (a) Example 67 from 5-bromo-3-formyl-1-(4-isopropoxyphenyl)indole-2-carboxylic acid ethyl ester (4.07 g, 9.46 mmol; see step (b) above) and 4-tert-butylphenylboronic acid (2.53 g, 14.19 mmol). Yield 4.16 g (91%).

(d) 5-(4-tert-Butylphenyl)-3-[(ethoxycarbonylmethylmethylamino)methyl]-1-(4-isopropoxyphenyl) indole-2-carboxylic acid ethyl ester N-Methyl glycine ethyl ester hydrochloride (255 mg, 1.66 mmol) was added to a suspension of 5-(4-tert-butylphenyl)-3-formyl-1-(4-isopropoxyphenyl)indole-2-carboxylic acid ethyl ester (400 mg, 0.83 mmol; see step (c) above) in MeOH (20 mL) and the pH was adjusted to 6 by the addition of a few drops of glacial acetic acid. After 1 h at rt, $NaCNBH_3$ (75 mg, 1.18 mmol) was added and the mixture was stirred at rt for 24 h, poured into $H_2O$ and extracted with EtOAc. The combined extracts were washed with $H_2O$ and brine, dried ($Na_2SO_4$), concentrated and purified by chromatography to give the sub-title compound. Yield 400 mg (87%).

(e) 5-(4-tert-Butylphenyl)-3-[(ethoxycarbonylmethylmethylamino)methyl]-1-(4-isopropoxyphenyl) indole-2-carboxylic acid A mixture of 5-(4-tert-butylphenyl)-3-[(ethoxycarbonylmethylmethylamino)methyl]-1-(4-isopropoxyphenyl)indole-2-carboxylic acid ethyl ester (198 mg, 0.36 mmol, see step (d)), NaOH (aq, 1 M, 2 mL) and dioxane (3 mL) was heated at 120° C. for 30 min, cooled, acidified with HCl (aq, 1 M) to pH 5 and extracted with EtOAc. The combined extracts were washed with $H_2O$ and brine, dried ($Na_2SO_4$), concentrated and purified by chromatography to afford the sub-title compound. Yield 184 mg (98%).

(f) [5-(4-tert-Butylphenyl)-2-carboxy-1-(4-isopropoxyphenyl)indol-3-ylmethyl]-carboxymethylmethylammonium chloride An excess of HCl (4 M in dioxane) was added to a suspension of 5-(4-tert-butylphenyl)-3-[(ethoxycarbonylmethylmethyl-amino)methyl]-1-(4-isopropoxyphenyl)indole-2-carboxylic acid ethyl ester (189 mg, 0.35 mmol; see step (e) above) in dioxane (4 mL). After 10 min the mixture was concentrated and the residue treated with $Et_2O$ and filtered to give the title compound.
200 MHz $^1$H NMR (DMSO-$d_6$) δ 8.28-8.23 (1H, m) 7.69-7.59 (3H, m) 7.54-7.46 (2H, m) 7.35-7.26 (2H, m) 7.14-7.03 (3H, m) 4.83 (2H, s) 4.71 (1H, m/z) 4.12 (2H, s) 2.84 (3H, s) 1.34 (6H, d, J=6.0 Hz) 1.33 (9H, s).

Example 87

1-[5-(4-tert-Butylphenyl)-2-carboxy-1-(4-isopropoxyphenyl)indol-3-ylmethyl]-2-carboxypyrrolidinium chloride The title compound was prepared in accordance with Example 86 from 5-(4-tert-butylphenyl)-3-formyl-1-(4-isopropoxyphenyl)indole-2-carboxylic acid ethyl ester and L-proline methyl ester hydrochloride.
200 MHz $^1$H NMR (DMSO-$d_6$) δ 14.0-11.0 (2H, br s) 8.33 (1H, s) 7.72-7.60 (3H, m) 7.54-7.45 (2H, m) 7.33-7.25 (2H, m) 7.15-7.03 (3H, m) 5.02 (1H, d, J=13.4 Hz) 4.94 (1H, d, J=13.4 Hz) 4.71 (1H, m) 4.45 (1H, dd, J=9.0, 6.5 Hz) 3.67-3.52 (1H, m) 3.44-3.25 (1H, m) 2.53-2.47 (1H, m) 2.18-1.80 (3H, m) 1.35 (6H, d, J=6.0 Hz) 1.33 (9H, s).

Example 88

3-(2-Carboxyethyl)-1-(4-isopropoxyphenyl)-5-(5-trifluoromethylpyridin-2-yl)indole-2-carboxylic acid (a) 3-Formyl-1-(4-isopropoxyphenyl)-5-(4,4,5,5-tetramethyl-[1,3,2]dioxaborolan-2-yl)indole-2-carboxylic acid ethyl ester $Pd_2(dba)_3$ (0.31 g, 0.034 mmol) and tricyclohexylphosphine (57 mg, 0.20 mmol) in dioxane (3.4 mL) was added under argon to a stirred mixture of 5-bromo-3-formyl-1-(4-isopropoxyphenyl)indole-2-carboxylic acid ethyl ester (581 mg, 1.35 mmol, see Example 86 step (b), KOAc (198 mg, 2.02 mmol), bis(pinacolato)diboron (375 mg, 1.46 mmol) and dioxane (10 mL) at 80° C. The mixture was stirred at 80° C. for 24 h, allowed to cool and filtered through Celite®. The solids were washed with EtOAc and the combined filtrates were concentrated and purified by chromatography to yield the sub-title compound. Yield 600 g (93%).

(b) 3-Formyl-1-(4-isopropoxyphenyl)-5-(5-trifluoromethylpyridin-2-yl)indole-2-carboxylic acid ethyl ester A mixture of 3-formyl-1-(4-isopropoxyphenyl)-5-(4,4,5,5-tetramethyl-[1,3,2]-dioxaborolan-2-yl)indole-2-carboxylic acid ethyl ester (600 mg, 1.26 mmol; see step (a) above), 2-bromo-5-(trifluoromethyl)pyridine (426 mg, 1.89 mmol), $Na_2CO_3$ (aq, 2 M, 1.89 mL, 3.78 mmol), $Pd(PPh_3)_4$ (70 mg, 0.06 mmol), EtOH (5 mL) and toluene (20 mL) was heated at 80° C. for 24 h, allowed to cool, poured into $H_2O$ and extracted with EtOAc. The combined extracts were washed with $H_2O$ and brine, dried ($Na_2SO_4$), concentrated and purified by chromatography to give the sub-title compound. Yield 500 mg (80%).

(c) 3-(2-Ethoxycarbonylvinyl)-1-(4-isopropoxyphenyl)-5-(5-trifluoromethylpyridin-2-yl)indole-2-carboxylic acid ethyl ester (Carbethoxymethylene)triphenylphosphorane (330 mg, 0.95 mmol) was added to a suspension of 3-formyl-1-(4-isopropoxyphenyl)-5-(5-trifluoromethylpyridin-2-yl)indole-2-carboxylic acid ethyl ester (427 mg, 0.95 mmol; see step (b) above) in DMF (15 mL) and the mixture was stirred at rt for 3 h. Another portion of (carbethoxymethylene)triphenylphosphorane (165 mg, 0.47 mmol) was added and the stirring continued for 12 h. The mixture was poured into $H_2O$ and extracted with EtOAc. The combined extracts were washed with $H_2O$, brine, dried ($Na_2SO_4$), concentrated and purified by chromatography to give the sub-title compound. Yield 386 mg (80%).

(d) 3-(2-Ethoxycarbonylethyl)-1-(4-isopropoxyphenyl)-5-(5-trifluoromethylpyridin-2-yl)indole-2-carboxylic acid ethyl ester A mixture of 3-(2-ethoxycarbonylvinyl)-1-(4-isopropoxyphenyl)-5-(5-trifluoromethylpyridin-2-yl)indole-2-carboxylic acid ethyl ester (150 mg, 0.26 mmol, see step (c) above), Pd—C (10%), cyclohexene (1.2 mL) in absolute EtOH was heated under microwave irradiation at 135° C. for 1 h. The mixture was filtered through Celite® and the solids were washed with EtOAc. The combined filtrates were concentrated to give the sub-title compound. Yield 150 mg (100%).

(e) 3-(2-Carboxyethyl)-1-(4-isopropoxyphenyl)-5-(5-trifluoromethylpyridin-2-yl)indole-2-carboxylic acid A mixture of 3-(2-ethoxycarbonylethyl)-1-(4-isopropoxyphenyl)-5-(5-trifluoromethylpyridin-2-yl)indole-2-carboxylic acid ethyl ester (150 mg, 0.26 mmol; see step (d) above), NaOH (aq, 1 M, 2.5 mL) and dioxane (4 mL) was heated at 90° C. for 1 h, cooled, acidified with HCl (aq, 1 M) to pH 2 and extracted with EtOAc. The combined extracts were washed with $H_2O$ and brine, dried ($Na_2SO_4$), concentrated and purified by chromatography to give the title compound. Yield 50 mg (38%).

200 MHz $^1$H NMR (DMSO-$d_6$) δ 15.0-14.0 (2H, br s) 9.06-8.97 (1H, m) 8.57-8.49 (1H, m) 8.32-8.18 (2H, m) 8.03 (1H, dd, J=8.8, 1.2 Hz) 7.27-7.16 (2H, m) 7.14 (1H, d, J=8.8 Hz) 7.04-6.91 (2H, m) 4.74-4.51 (1H, m) 3.40-3.24 (2H, m) 2.77-2.63 (2H, m) 1.30 (6H, d, J=5.9 Hz).

Example 89

2-Carboxymethyl-5-(3-chlorophenoxy)-1-(4-isopropoxyphenyl)indole-3-carboxylic acid (a) 2-Ethoxycarbonylmethyl-5-hydroxy-1-(4-isopropoxyphenyl)indole-3-carboxylic acid ethyl ester The sub-title compound was prepared in accordance with step (b) Example 1 from 3-(4-isopropoxyphenylamino)pent-2-enedioic acid diethyl ester (2.76 g, 10.5 mmol; prepared according to the procedure in *J. Org. Chem.* 1951, 16, 896). Yield 1.40 g (40%).

(b) 2-Ethoxycarbonylmethyl-5-(3-chlorophenoxy)-1-(4-isopropoxyphenyl)indole-3-carboxylic acid ethyl ester The sub-title compound was prepared in accordance with step (c) Example 1 from 2-ethoxycarbonylmethyl-5-hydroxy-1-(4-isopropoxyphenyl)indole-3-carboxylic acid ethyl ester (0.96 g, 2.26 mmol; see step (a) above) and 3-chlorophenylboronic acid (0.70 g, 4.52 mmol). Yield 100 mg (39%).

(c) 2-Carboxymethyl-(3-chlorophenoxy)-1-(4-isopropoxyphenyl)indole-3-carboxylic acid A mixture of 2-ethoxycarbonylmethyl-5-(3-chlorophenoxy)-1-(4-isopropoxyphenyl)indole-3-carboxylic acid ethyl ester (0.10 g, 0.19 mmol); see step (b) above), NaOH (0.10 g, 2.50 mmol), $H_2O$ (2.5 mL) and EtOH (2.5 mL) was heated at reflux for 2 h, cooled and acidified with HCl (aq, conc). The solid was collected and dried to afford the title compound. Yield 0.06 g (66%).

200 MHz $^1$H-NMR (DMSO-$d_6$) δ 13.0-12.0 (2H, br s) 7.72 (1H, d, J=1.9 Hz) 7.42-7.30 (3H, m) 7.21-7.08 (3H, m) 7.04 (1H, d, J=8.8 Hz) 7.02-6.96 (2H, m) 6.92 (1H, dd, J=8.8, 1.9 Hz) 4.73 (1H, m) 3.95 (2H, s) 1.33 (6H, d, J=5.9 Hz).

Example 90

The following compounds are prepared in accordance with techniques described herein:
3-(2-carboxyethyl)-1-(4-(cyclopentyloxy)phenyl)-5-(4-(trifluoromethyl)phenyl)indole-2-carboxylic acid;
1-(4-(cyclopentyloxy)phenyl)-3-(2,9-dicarboxyethyl)-5-(4-(trifluoro-methyl)phenyl)indole-2-carboxylic acid;
3-(3-carboxypropyl)-1-(4-isopropoxyphenyl)-5-(5-(trifluoromethyl)pyridin-2-yl)indole-2-carboxylic acid;
3-((1R,2R)-2-carboxycyclohexyl)-1-(4-isopropoxyphenyl)-5-(5-(trifluoromethyl)pyridin-2-yl)indole-2-carboxylic acid;
3-(2-carboxypropan-2-yl)-1-(4-isopropoxyphenyl)-5-(5-(trifluoromethyl)pyridin-2-yl)indole-2-carboxylic acid;
3-((1R,2R)-2-carboxycyclopropyl)-1-(4-isopropoxyphenyl)-5-(5-(trifluoromethyl)pyridin-2-yl)indole-2-carboxylic acid;

2-(carboxymethyl)-1-(4-isopropoxyphenyl)-5-(5-(trifluoromethyl)pyridin-2-yl)indole-3-carboxylic acid;
2-(4-carboxyphenyl)-1-(4-isopropoxyphenyl)-5-(5-(trifluoromethyl)pyridin-2-yl)indole-3-carboxylic acid;
1-(4-(cyclopentyloxy)phenyl)-5-(4-(trifluoromethyl)phenyl) indole-2,3-dicarboxylic acid;
1-(4-(cyclopentyloxy)phenyl)-3-phosphono-5-(4-(trifluoromethyl)phenyl)indole-2-carboxylic acid;
3-(3-carboxyphenyl)-1-(4-isopropoxyphenyl)-5-(5-(trifluoromethyl)pyridin-2-yl)indole-2-carboxylic acid; and
3-(5-carboxypyridin-3-yl)-1-(4-isopropoxyphenyl)-5-(5-(trifluoromethyl)pyridin-2-yl)indole-2-carboxylic acid.

Example 91

Title compounds of the examples were tested in the biological test described above and were found to exhibit 50% inhibition of mPGES-1 at a concentration of 10 µM or below For example, the following representative compounds of the examples exhibited the following $IC_{50}$ values:
Example 19: 4300 nM
Example 67: 1900 nM
Example 85: 6900 nM
Example 87: 2300 nM
Example 88: 5400 nM

The invention claimed is:
1. A compound of formula I,

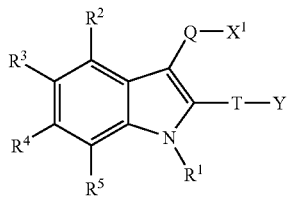

I wherein
one of the groups $R^2$, $R^3$, $R^4$ and $R^5$ represents -D-E and:
a) the other groups are independently selected from hydrogen, $G^1$, an aryl group, a heteroaryl group (which latter two groups are optionally substituted by one or more substituents selected from A), $C_{1-8}$ alkyl and a heterocycloalkyl group (which latter two groups are optionally substituted by one or more substituents selected from $G^1$ and/or $Z^1$); and/or
b) any two other groups which are adjacent to each other are optionally linked to form, along with two atoms of the essential benzene ring in the compound of formula I, a 3- to 8-membered ring, optionally containing 1 to 3 heteroatoms, which ring is itself optionally substituted by one or more substituents selected from halo, —$R^6$, —$OR^6$ and =O;
D represents a single bond, —O—, —$C(R^7)(R^8)$—, $C_{2-4}$ alkylene, —C(O)— or —$S(O)_m$—;
$R^1$ and E independently represent an aryl group or a heteroaryl group, both of which groups are optionally substituted by one or more substituents selected from A;
$R^7$ and $R^8$ independently represent H, halo or $C_{1-6}$ alkyl, which latter group is optionally substituted by halo, or $R^7$ and $R^8$ may together form, along with the carbon atom to which they are attached, a 3- to 6-membered ring, which ring optionally contains a heteroatom and is optionally substituted by one or more substituents selected from halo and $C_{1-3}$ alkyl, which latter group is optionally substituted by one or more halo substituents;
Q represents a single bond, or a $C_{1-8}$ alkylene or $C_{2-8}$ heteroalkylene chain, both of which latter two groups optionally contain one or more unsaturations and are optionally substituted by one or more substituents selected from $G^1$ and/or $Z^1$;
$X^1$ represents:
(a) —$C(O)OR^{9a}$, —$C(O)N(R^{10b})R^{9b}$, —$C(O)N(H)C(=NR^{9c})N(R^{10d})R^{9d}$; —$C(O)N(H)CN$, —$S(O)_3R^{9e}$, —$P(O)(OR^{9f})_2$, —$P(O)(OR^{9g})N(R^{10h})R^{9h}$, —$P(O)(N(R^{10i})R^{9i})_2$, —$B(OR^{9y})_2$, —$C(O)N(H)S(O)_2R^{11}$ or, provided that T does not represent a single bond when Y represents —$C(O)OR^{9a}$, unsubstituted tetrazolyl;
(b) an aryl group or a heteroaryl group, both of which are substituted by at least one substituent selected from $X^2$, and one or more further optional substituents selected from A; or
(c) a heterocycloalkyl group substituted by at least one substituent selected from $X^2$, and one or more further optional substituents selected from $G^1$ and/or $Z^1$;
$X^2$ represents —$C(O)OR^{9a}$, —$C(O)N(R^{10b})R^{9b}$, —$C(O)N(H)C(=NR^{9c})N(R^{10d})R^{9d}$; —$C(O)N(H)CN$, —$S(O)_3R^{9e}$, —$P(O)(OR^{9f})_2$, —$P(O)(OR^{9g})N(R^{10h})R^{9h}$, —$P(O)(N(R^{10i})R^{9i})_2$, —$B(OR^{9y})_2$, —$C(O)N(H)S(O)_2R^{11}$ or unsubstituted tetrazolyl;
T represents:
(a) a single bond;
(b) a $C_{1-8}$ alkylene or a $C_{2-8}$ heteroalkylene chain, both of which latter two groups:
(i) optionally contain one or more unsaturations;
(ii) are optionally substituted by one or more substituents selected from $G^1$ and/or $Z^1$; and/or
(iii) may comprise an additional 3- to 8-membered ring formed between any one or more members of the $C_{1-8}$ alkylene or $C_{2-8}$ heteroalkylene chain, which ring optionally contains 1 to 3 heteroatoms and/or 1 to 3 unsaturations and which ring is itself optionally substituted by one or more substituents selected from $G^1$ and/or $Z^1$;
(c) an arylene group or a heteroarylene group, both of which groups are optionally substituted by one or more substituents selected from A; or
(d) -$T^1$-$W^1$-$T^2$-;
one of $T^1$ and $T^2$ represents a $C_{1-8}$ alkylene or a $C_{2-8}$ heteroalkylene chain, both of which latter two groups:
(i) optionally contain one or more unsaturations;
(ii) are optionally substituted by one or more substituents selected from $G^1$ and/or $Z^1$; and/or
(iii) may comprise an additional 3- to 8-membered ring formed between any one or more members of the $C_{1-8}$ alkylene or $C_{2-8}$ heteroalkylene chain, which ring optionally contains 1 to 3 heteroatoms and/or 1 to 3 unsaturations and which ring is itself optionally substituted by one or more substituents selected from $G^1$ and/or $Z^1$;
and the other represents an arylene group or a heteroarylene group, both of which groups are optionally substituted by one or more substituents selected from A;
$W^1$ represents —O— or —$S(O)_m$—;
m represents 0, 1 or 2;
Y represents $C(H)(CF_3)OH$, —$C(O)CF_3$, —$C(OH)_2CF_3$, —$C(O)OR^{9a}$, —$S(O)_3R^{9e}$, —$P(O)(OR^{9f})_2$, —$P(O)(OR^{9g})N(R^{10h})R^{9h}$, —$P(O)(N(R^{10i})R^{9i})_2$, —$B(OR^{9y})_2$, —$C(CF_3)_2OH$, —$S(O)_2N(R^{10z})R^{9z}$ or any one of the following groups:

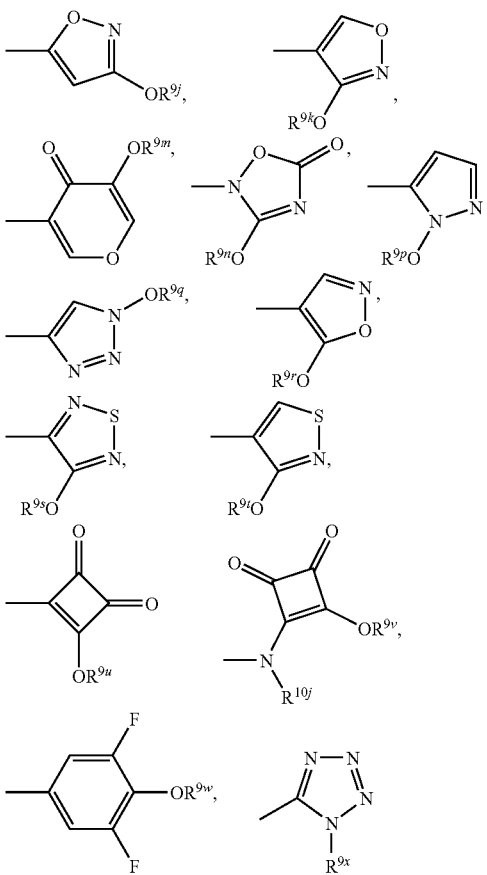

$R^6$, $R^{9a}$ to $R^{9z}$, $R^{10b}$, $R^{10d}$, $R^{10h}$, $R^{10i}$, $R^{10j}$ and $R^{10z}$ independently represent:

I) hydrogen;
II) an aryl group or a heteroaryl group, both of which are optionally substituted by one or more substituents selected from B; or
III) $C_{1-8}$ alkyl or a heterocycloalkyl group, both of which, are optionally substituted by one or more substituents selected from $G^1$ and/or $Z^1$; or any pair of $R^{9a}$ to $R^{9y}$ and $R^{10b}$, $R^{10d}$, $R^{10h}$, $R^{10i}$ or $R^{10j}$, may be linked together to form, along with the atom(s) to which they are attached, a 3- to 8-membered ring, optionally containing 1 to 3 heteroatoms and/or 1 to 3 double bonds, which ring is optionally substituted by one or more substituents selected from $G^1$ and/or $Z^1$;

$R^{11}$ represents:
I) an aryl group or a heteroaryl group, both of which are optionally substituted by one or more substituents selected from B; or
II) $C_{1-8}$ alkyl or a heterocycloalkyl group, both of which are optionally substituted by one or more substituents selected from $G^1$ and/or $Z^1$;

A represents:
I) an aryl group or a heteroaryl group, both of which are optionally substituted by one or more substituents selected from B;
II) $C_{1-8}$ alkyl or a heterocycloalkyl group, both of which are optionally substituted by one or more substituents selected from $G^1$ and/or $Z^1$; or
III) a $G^1$ group;

$G^1$ represents halo, cyano, $-N_3$, $-NO_2$, $-ONO_2$ or $-A^1-R^{12a}$;

wherein $A^1$ represents a single bond or a spacer group selected from $-C(O)A^2-$, $-S(O)_2A^3-$, $-N(R^{13a})A^4-$ or $-OA^5-$, in which:

$A^2$ represents a single bond, $-O-$, $-N(R^{13b})-$ or $-C(O)-$;
$A^3$ represents a single bond, $-O-$ or $-N(R^{13c})-$;
$A^4$ and $A^5$ independently represent a single bond, $-C(O)-$, $-C(O)N(R^{13d})-$, $-C(O)O-$, $-S(O)_2-$ or $-S(O)_2N(R^{13e})-$;
$Z^1$ represents $=O$, $=S$, $=NOR^{12b}$, $=NS(O)_2N(R^{13f})R^{12c}$, $=NCN$ or $=C(H)NO_2$;

B represents:
I) an aryl group or a heteroaryl group, both of which are optionally substituted by one or more substituents selected from $G^2$;
II) $C_{1-8}$ alkyl or a heterocycloalkyl group, both of which are optionally substituted by one or more substituents selected from $G^2$ and/or $Z^2$; or
III) a $G^2$ group;

$G^2$ represents halo, cyano, $-N_3$, $-NO_2$, $-ONO_2$ or $-A^6-R^{14a}$;

wherein $A^6$ represents a single bond or a spacer group selected from $-C(O)A^7-$, $-S(O)_2A^8-$, $-N(R^{15a})A^9-$ or $-OA^{10}-$, in which:

$A^7$ represents a single bond, $-O-$, $-N(R^{15b})-$ or $-C(O)-$;
$A^8$ represents a single bond, $-O-$ or $-N(R^{15c})-$;
$A^9$ and $A^{10}$ independently represent a single bond, $-C(O)-$, $-C(O)N(R^{15d})-$, $-C(O)O-$, $-S(O)_2-$ or $-S(O)_2N(R^{15e})-$;
$Z^2$ represents $=O$, $=S$, $=NOR^{14b}$, $=NS(O)_2N(R^{15f})R^{14c}$, $=NCN$ or $=C(H)NO_2$;

$R^{12a}$, $R^{12b}$, $R^{12c}$, $R^{13a}$, $R^{13b}$, $R^{13c}$, $R^{13d}$, $R^{13e}$, $R^{13f}$, $R^{14a}$, $R^{14b}$, $R^{14c}$, $R^{15a}$, $R^{15b}$, $R^{15c}$, $R^{15d}$, $R^{15e}$ and $R^{15f}$ are independently selected from:

i) hydrogen;
ii) an aryl group or a heteroaryl group, both of which are optionally substituted by one or more substituents selected from $G^3$;
iii) $C_{1-8}$ alkyl or a heterocycloalkyl group, both of which are optionally substituted by $G^3$ and/or $Z^3$; or any pair of $R^{12a}$ to $R^{12c}$ and $R^{13a}$ to $R^{13f}$, and/or $R^{14a}$ to $R^{14c}$ and $R^{15a}$ to $R^{15f}$ may be linked together to form with those, or other relevant, atoms a further 3- to 8-membered ring, optionally containing 1 to 3 heteroatoms and/or 1 to 3 double bonds, which ring is optionally substituted by one or more substituents selected from $G^3$ and/or $Z^3$;

$G^3$ represents halo, cyano, $-N_3$, $-NO_2$, $-ONO_2$ or $-A^{11}-R^{16a}$;

wherein $A^{11}$ represents a single bond or a spacer group selected from $-C(O)A^{12}-$, $-S(O)_2A^{13}-$, $-N(R^{17a})A^{14}-$ or $-OA^{15}-$, in which:

$A^{12}$ represents a single bond, $-O-$, $-N(R^{17b})-$ or $-C(O)-$;
$A^{13}$ represents a single bond, $-O-$ or $-N(R^{17c})-$;
$A^{14}$ and $A^{15}$ independently represent a single bond, $-C(O)-$, $-C(O)N(R^{17d})-$, $-C(O)O-$, $-S(O)_2-$ or $-S(O)_2N(R^{17e})-$;
$Z^3$ represents $=O$, $=S$, $=NOR^{16b}$, $=NS(O)_2N(R^{17f})R^{16c}$, $=NCN$ or $=C(H)NO_2$;

$R^{16a}$, $R^{16b}$, $R^{16c}$, $R^{17a}$, $R^{17b}$, $R^{17c}$, $R^{17d}$, $R^{17e}$ and $R^{17f}$ are independently selected from:

i) hydrogen;
ii) $C_{1-6}$ allyl or a heterocycloalkyl group, both of which groups are optionally substituted by one or more substituents selected from halo, $C_{1-4}$ alkyl, $-N(R^{18a})R^{19a}$, $-OR^{18b}$ and $=O$; and
iii) an aryl or heteroaryl group, both of which are optionally substituted by one or more substituents selected from halo, $C_{1-4}$ alkyl, $-N(R^{18c})R^{19b}$ and $-OR^{18d}$; or
i) hydrogen;
ii) $C_{1-6}$ alkyl or a heterocycloalkyl group, both of which are optionally substituted by one or more substituents selected from halo, $C_{1-4}$ alkyl, $-N(R^{18a})R^{19a}$, $-OR^{18b}$ and $=O$; and
iii) an aryl group or a heteroaryl group, both of which are optionally substituted by one or more substituents selected from $C_{1-4}$ alkyl, $-N(R^{18c})R^{19b}$ and $-OR^{18d}$; or any pair of $R^{16a}$ to $R^{16c}$ and $R^{17a}$ to $R^{17f}$ may be linked together to form with those, or other relevant, atoms a further 3- to 8-membered ring, optionally containing 1 to 3 heteroatoms and/or 1 to 3 double bonds, which ring is optionally substituted by one or more substituents selected from halo, $C_{1-4}$ alkyl, $-N(R^{18e})R^{19c}$ and $-OR^{18f}$ and $=O$;
$R^{18a}$, $R^{18b}$, $R^{18c}$, $R^{18d}$, $R^{18e}$, $R^{16f}$, $R^{19a}$, $R^{19b}$ and $R^{19c}$ are independently selected from hydrogen and $C_{1-4}$ alkyl, which latter group is optionally substituted by one or more halo groups;
or a pharmaceutically-acceptable salt thereof.

2. A compound as claimed in claim 1, wherein A represents a $C_{4-5}$ heterocycloalkyl group, $G^1$ or $C_{1-6}$ alkyl optionally substituted by one or more $G^1$ groups.

3. A compound as claimed in claim 2, wherein A represents $G^1$ or $C_{1-6}$ alkyl optionally substituted by one or more $G^1$ groups.

4. A compound as claimed in claim 3, wherein $G^1$ represents cyano, fluoro, chloro or -$A^1$-$R^{12a}$.

5. A compound as claimed in claim 4, wherein $G^1$ represents fluoro, chloro or -$A^1$-$R^{12a}$.

6. A compound as claimed in claim 5, wherein $A^1$ represents $-S(O)_2-$, $-C(O)A^2-$, $-N(R^{13a})A^4-$ or $-OA^5$.

7. A compound as claimed in claim 6, wherein A represents $-C(O)A^2-$, $-N(R^{13a})A^4-$ or $-OA^5-$.

8. A compound as claimed in claim 7, wherein $A^2$ represents $-N(R^{13a})-$ or $-O-$.

9. A compound as claimed in claim 8, wherein $A^2$ represents $-O-$.

10. A compound as claimed in claim 9, wherein $A^4$ represents a single bond or $-C(O)-$.

11. A compound as claimed in claim 10, wherein $A^4$ represents $-C(O)-$.

12. A compound as claimed in claim 1, wherein $A^5$ represents a single bond.

13. A compound as claimed in claim 1, wherein T represents a single bond, $C_{1-3}$ alkylene or phenylene.

14. A compound as claimed in claim 1, wherein Y represents $-C(O)OR^{9a}$.

15. A compound as claimed in claim 1, wherein Q represents a single bond, linear $C_{1-4}$ alkylene, branched $C_{2-4}$ alkylene or cyclic $C_{3-7}$ alkylene, all of which alkylene groups are optionally substituted with one or more $G^1$ groups, or $C_{2-3}$ heterocycloalkylene, wherein the heteroatom group that interrupts the $C_{2-3}$ alkylene chain is $-N(R^{20})-$, in which $R^{20}$ represents $C_{1-3}$ alkyl.

16. A compound as claimed in claim 1, wherein D represents a single bond or $-O-$.

17. A compound as claimed in claim 1, wherein $R^1$, $X^1$ (when $X^1$ represents an aryl or heteroaryl group) and/or E represent optionally substituted carbazolyl, phenyl, naphthyl, pyrrolyl, furanyl, thienyl, pyrazolyl, imidazolyl, oxazolyl, isoxazolyl, thiazolyl, pyridyl, indazolyl, indolyl, indolinyl, isoindolinyl, quinolinyl, 1,2,3,4- tetrahydroquinolinyl, isoquinolinyl, 1,2,3,4-tetrahydroisoquinolinyl, quinolizinyl, benzofuranyl, isobenzofuranyl, chromanyl, benzothienyl, pyridazinyl, pyrimidinyl, pyrazinyl, indazolyl, benzimidazolyl, quinazolinyl, quinoxalinyl, 1,3-benzodioxolyl, tetrazolyl, benzothiazolyl, and/or benzodioxanyl groups.

18. A compound as claimed in claim 17, wherein $R^1$, $X^1$ and/or E represent optionally substituted phenyl, naphthyl, pyrrolyl, furanyl, thienyl, pyrazolyl, imidazolyl, oxazolyl, isoxazolyl, thiazolyl, pyridyl, indazolyl, indolyl, indolinyl, isoindolinyl, quinolinyl, 1,2,3,4-tetrahydroquinolinyl, isoquinolinyl, 1,2,3,4-tetrahydroisoquinolinyl, quinolizinyl, benzofuranyl, isobenzofuranyl, chromanyl, benzothienyl, pyridazinyl, pyrimidinyl, pyrazinyl, indazolyl, benzimidazolyl, quinazolinyl, quinoxalinyl, 1,3-benzodioxolyl, tetrazolyl, benzothiazolyl, and/or benzodioxanyl groups.

19. A compound as claimed in claim 17 or claim 18, wherein $R^1$ represents optionally substituted carbazolyl, benzodioxolyl, phenyl, pyridyl or imidazolyl.

20. A compound as claimed in claim 17, wherein E represents optionally substituted naphthyl, quinolinyl, phenyl, pyridyl or imidazolyl.

21. A compound as claimed in claim 20, wherein $R^1$ and E independently represent optionally substituted phenyl, pyridyl or imidazolyl.

22. A compound as claimed in claim 17, wherein the optional substituents are selected from $-C(O)OR^{21}$, $-C(O)N(R^{21})R^{22}$, $-S(O)_2R^{21}$, halo, cyano, $-NO_2$, $C_{1-6}$ alkyl (which alkyl group may be linear or branched, cyclic, part-cyclic, unsaturated and/or optionally substituted with one or more halo group), heterocycloalkyl (which heterocycloalkyl groups is optionally substituted by one or more substituents selected from $C_{1-3}$ alkyl and $=O$), $-OR^{21}$ and $-N(R^{21})R^{22}$, wherein $R^{21}$ and $R^{22}$ independently represent H or $C_{1-6}$ alkyl (which alkyl group is optionally substituted by one or more halo groups).

23. A compound as claimed in claim 22, wherein the optional substituents are selected from halo, cyano, $-NO_2$, $C_{1-6}$ alkyl (which alkyl group may be linear or branched, cyclic, part-cyclic, unsaturated and/or optionally substituted with one or more halo group), heterocycloalkyl (which heterocycloalkyl groups is optionally substituted by one or more substituents selected from $C_{1-3}$ alkyl and $=O$), $-OR^{21}$ and $-N(R^{21})R^{22}$, wherein $R^{21}$ and $R^{22}$ independently represent H or $C_{1-6}$ alkyl (which alkyl group is optionally substituted by one or more halo groups).

24. A compound as claimed in claim 23, wherein $X^1$ represents unsubstituted tetrazolyl, $-C(O)OR^{9a}$, $-P(O)(OR^{9f})$, or a tetrazolyl group, a phenyl or a pyridyl group substituted by $X^2$.

25. A compound as claimed in claim 23, wherein one of $R^4$ and $R^3$ represents -D-E and the other represents H.

26. A compound as claimed in claim 25, wherein $R^3$ represents -D-E.

27. A compound as claimed in claim 17, wherein $R^2$ and/or $R^5$ represent H.

28. A compound as claimed in claim 17, wherein $X^2$ represents $-C(O)OR^{9a}$.

29. A compound as claimed in claim 17, wherein $R^{9a}$ to $R^{9z}$ represent H or $C_{1-4}$ alkyl.

30. A compound as claimed in claim 17, wherein $R^{12a}$, $R^{12b}$ and $R^{12c}$ independently represent H or $C_{1-5}$ alkyl.

31. A compound as claimed in claim 17, wherein $R^{13a}$, $R^{13b}$, $R^{13c}$, $R^{13d}$, $R^{13e}$ and $R^{13f}$ independently represent H or $C_{1-3}$ alkyl.

32. A compound as defined in claim 1, or a pharmaceutically-acceptable salt thereof, for use as a pharmaceutical.

33. A pharmaceutical formulation including a compound as defined in claim 1, or a pharmaceutically-acceptable salt thereof, in admixture with a pharmaceutically acceptable adjuvant, diluent or carrier.

34. A combination product comprising:
   (A) a compound as defined in claim 1, or a pharmaceutically-acceptable salt thereof; and
   (B) a therapeutic agent that is useful in the treatment of inflammation, wherein each of components (A) and (B) is formulated in admixture with a pharmaceutically-acceptable adjuvant, diluent or carrier.

35. A combination product as claimed in claim 34 which comprises a pharmaceutical formulation including a compound as defined in claim 1, or a pharmaceutically-acceptable salt thereof, another therapeutic agent that is useful in the treatment of inflammation, and a pharmaceutically-acceptable adjuvant, diluent or carrier.

36. A combination product as claimed in claim 34, which comprises a kit of parts comprising components:
   (a) a pharmaceutical formulation including a compound as defined in claim 1, or a pharmaceutically-acceptable salt thereof, in admixture with a pharmaceutically-acceptable adjuvant, diluent or carrier; and
   (b) a pharmaceutical formulation including another therapeutic agent that is useful in the treatment of inflammation in admixture with a pharmaceutically-acceptable adjuvant, diluent or carrier,
   which components (a) and (b) are each provided in a form that is suitable for administration in conjunction with the other.

37. A process for the preparation of a compound as defined in claim 1, which comprises:
   (i) reaction of a compound of formula II,

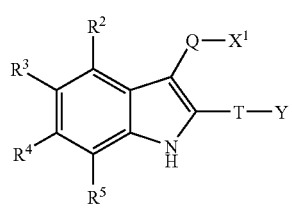

II wherein Q, $X^1$, $R^2$, $R^3$, $R^4$, $R^5$, T and Y are as defined in claim 1, with a compound of formula III, $R^1L^1$     III wherein $L^1$ represents a suitable leaving group and $R^1$ is as defined in claim 1;

(ii) reaction of a compound of formula IV,

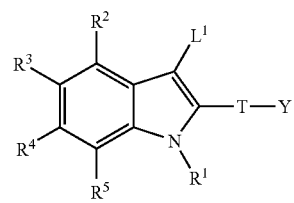

IV wherein $R^1$, $R^2$, $R^3$, $R^4$, $R^5$, T and Y are as defined in claim 1 and $L^1$ is as defined above, with a compound of formula V, $X^1$-Q-$L^2$     V wherein $L^2$ represents a suitable leaving group and Q and $X^1$ are as defined in claim 1;

(iia) for compounds of formula I in which $X^1$ represents —C(O)N(H)C(=$NR^{9c}$)N($R^{10d}$)$R^{9d}$, —C(O)N(H)CN or —C(O)N(H)S(O)$_2R^{11}$, reaction of either a compound corresponding to a compound of formula I but in which $X^1$ represents H, or a compound of formula IV in which the $L^1$ group is activated, with a compound of formula VA, $R^{za}$—N=C=O     VA wherein $R^{za}$ represents —C(=$NR^{9c}$)N($R^{10d}$)$R^{9d}$, —CN or —S(O)$_2R^{11}$, followed by quenching with a suitable proton source;

(iii) for compounds of formula I in which Q represents $C_{2-8}$ heteroalkylene (optionally substituted by one or more substituents selected from $G^1$), in which the heteroatom-containing group interrupting the alkylene chain is —N($R^{20}$)—, $R^{20}$ represents $C_{1-4}$ alkyl, optionally substituted by one or more halo groups and $X^1$ is as defined in claim 1, or Q represents $C_{1-8}$ alkylene (optionally substituted by one or more substituents selected from $G^1$) and $X^1$ is a nitrogen-containing heterocycloalkyl group substituted by $X^2$, which group is attached to Q through a nitrogen atom in that group, reaction of a compound of formula VI,

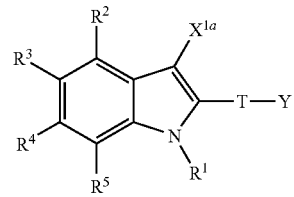

VI wherein $X^{1a}$ represents either (a) in the case of formation of a compound of formula I in which Q represents optionally substituted $C_{2-8}$ heteroalkylene, in which the heteroatom-containing group interrupting the alkylene chain is —N($R^{20}$)—, a $C_{1-7}$ alkyl group substituted by a —CHO group and optionally substituted with one or more substitutents selected from $G^1$; or (b) in the case of formation of a compound of formula I in which Q represents $C_{1-8}$ alkylene and $X^1$ is a nitrogen-containing heterocycloalkyl group as defined above, a $C_{1-8}$ alkyl group substituted by a $Z^1$ group in which $Z^1$ is =O and optionally substituted by one or more substituents selected from G¹, and R¹, R², R³, R⁴, R⁵, T and Y are as defined in claim 1 under reductive amination conditions in the presence of a compound of formula VII, $$R^{23}(R^{24})NH \qquad\qquad VII$$

wherein either (a) $R^{24}$ represents $C_{1-7}$ alkyl, optionally substituted with one or more substitutents selected from $G^1$, provided that the total number of carbon atoms in $X^{1a}$ and $R^{24}$ in combination is between 2 and 8, and $R^{23}$ represents $R^{20}$ as defined above; or (b) $R^{23}$ and $R^{24}$ and the nitrogen atom to which they are attached together represent a nitrogen-containing heterocycloalkyl group substituted by at least one substituent selected from $X^2$ and one or more further optional substitutents selected from $G^1$, as defined in claim 1;

(iv) for compounds of formula I in which Q represents optionally substituted $C_{2-8}$ alkenylene or $C_{2-8}$ heteroalkenylene (in which a point of unsaturation is between the carbon atoms that are α and β to the indole ring), reaction of a corresponding compound of formula IV in which $L^1$ represents halo with a compound of formula VIIIA $$H_2C=C(H)\text{-}Q^a\text{-}X^1 \qquad\qquad VIIIA$$

or, reaction of a compound of formula VI in which $X^{1a}$ represents —CHO with either a compound of formula VIIIB, $$(EtO)_2P(O)CH_2\text{-}Q^a\text{-}X^1 \qquad\qquad VIIIB$$

or the like, or a compound of formula VIIIC, $$(Ph)_3P=CH\text{-}Q^a\text{-}X^1 \qquad\qquad VIIIC$$

or the like, wherein, in each case, $Q^a$ represents a single bond, $C_{1-6}$ alkylene or $C_{1-6}$ heteroalkylene optionally interrupted by a heteroatom, which alkylene or heteroalkylene groups are optionally substituted with one of more substituents selected from $G^1$ and/or $Z^1$ and $X^1$, $G^1$ and $Z^1$ are as defined in claim 1;

(v) for compounds of formula I in which Q represents optionally substituted, saturated $C_{2-8}$ alkylene, saturated cycloalkylene, saturated $C_{2-8}$ heteroalkylene, saturated heterocycloalkylene, $C_{2-8}$ alkenylene, cycloalkenylene, $C_{2-8}$ heteroalkenylene or heterocycloalkenylene, reduction of a corresponding compound of formula I in which Q represents optionally substituted $C_{2-8}$ alkenylene, cycloalkenylene, $C_{2-8}$ heteroalkenylene, heterocycloalkenylene, $C_{2-8}$ alkynylene, cycloalkynylene, $C_{2-8}$ heteroalkynylene or heterocycloalknylene (as appropriate);

(vi) for compounds of formula I in which D represents a single bond, —C(O)—, —C(R⁷)(R⁸)—, $C_{2-4}$ alkylene or —S(O)₂—, reaction of a compound of formula IX,

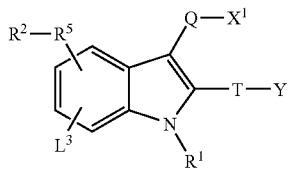

wherein $L^3$ represents $L^1$ or $L^2$ as defined above, which group is attached to one or more of the carbon atoms of the benzenoid ring of the indole, R²-R⁵ represents whichever of the three other substituents on the benzenoid ring are already present in that ring, and Q, X¹, R¹, R², R³, R⁴, R⁵, T and Y are as defined in claim 1, with a compound of formula X, $$E\text{-}D^a\text{-}L^4 \qquad\qquad X$$

wherein $D^a$ represents a single bond, —C(O)—, —C(R⁷)(R⁸)—, $C_{2-4}$ alkylene or —S(O)₂—, $L^4$ represents $L^1$ (when $L^3$ is $L^2$) or $L^2$ (when $L^3$ is $L^1$), E, R⁷ and R⁸ are as defined in claim 1 and $L^1$ and $L^2$ are as defined above;

(vii) for compounds of formula I in which D represents —S—, —O— or $C_{2-4}$ alkynylene in which the triple bond is adjacent to E, reaction of a compound of formula IX as defined above in which $L^3$ represents $L^2$ as defined above with a compound of formula XI, $$E\text{-}D^b\text{-}H \qquad\qquad XI$$

wherein $D^b$ represents —S—, —O— or $C_{2-4}$ alkynylene in which the triple bond is adjacent to E and E is as defined in claim 1;

(viii) for compounds of formula I in which D represents —S(O)— or —S(O)₂—, oxidation of a corresponding compound of formula I in which D represents —S—;

(ix) for compounds of formula I in which D represents —O— or —S—, reaction of a compound of formula XII,

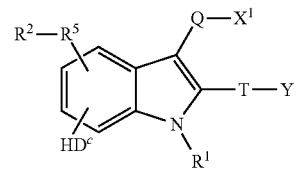

wherein the -$D^c$-H group is attached to one or more of the carbon atoms of the benzenoid ring of the indole, $D^c$ represents —O— or —S— and Q, X¹, R¹, T and Y are as defined in claim 1, and R²-R⁵ is as defined above with a compound of formula XIII, $$E\text{-}L^2 \qquad\qquad XIII$$

wherein $L^2$ is as defined above;

(x) for compounds of formula I in which T and Y are as defined in claim 1, provided that when Y represents —C(O)OR$^{9a}$, —S(O)₃R$^{9e}$, —P(O)(OR$^{9f}$)₂, —P(O)(OR$^{9g}$)N(R$^{10h}$)R$^{9h}$, —P(O)(N(R$^{10i}$)R$^{9i}$)₂, —B(OR$^{9y}$)₂ or —S(O)₂N(R$^{10z}$)R$^{9z}$, R$^{9a}$, R$^{9e}$ to R$^{9i}$, R$^{9y}$, R$^{9z}$, R$^{10h}$, R$^{10i}$ and R$^{10z}$ are other than H, reaction of a compound of formula XIV,

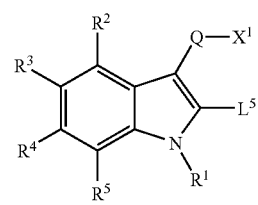

wherein $L^5$ represents a suitable group, and Q, X¹, R¹, R², R³, R⁴ and R⁵ are as defined in claim 1, with a compound of formula XV, $$L^6\text{-}T\text{-}Y^a \qquad\qquad XV$$

wherein $Y^s$ represents Y, provided that when Y represents —C(O)OR$^{9a}$, —S(O)$_3$R$^{9e}$, —P(O)(OR$^{9f}$)$_2$, —P(O)(OR$^{9g}$)N(R$^{10h}$)R$^{9h}$, —P(O)(N(R$^{10i}$)R$^{9i}$)$_2$, —B(OR$^{9y}$)$_2$ or —S(O)$_2$N(R$^{10z}$)R$^{9z}$, R$^{9a}$, R$^{9e}$ to R$^{9i}$, R$^{9y}$, R$^{9z}$, R$^{10h}$, R$^{10i}$ and R$^{10z}$ are other than H, L$^6$ represents a suitable leaving group and T is as defined in claim 1;

(xi) for compounds of formula I in which T represents a single bond, Y represents —C(O)OR$^{9a}$ and R$^{9a}$ represents H, reaction of a compound of formula XIV as defined above in which L$^5$ represents either:
(I) an alkali metal; or
(II) —Mg-halide,
with carbon dioxide, followed by acidification;

(xii) for compounds of formula I in which T represents a single bond and Y represents —C(O)OR$^{9a}$, reaction of a corresponding compound of formula XIV in which L$^5$ is a suitable leaving group with CO (or a reagent that is a suitable source of CO), in the presence of a compound of formula XVA, R$^{9a}$OH         XVA wherein R$^{9a}$ is as defined in claim 1, and an appropriate catalyst system;

(xiii) for compounds of formula I in which T represents a single bond, Y represents —B(OR$^{9y}$)$_2$ and R$^{9y}$ represents H, reaction of a compound of formula XIV as defined above with boronic acid or a protected derivative thereof, followed by (if necessary) deprotection;

(xiv) for compounds of formula I in which T represents a single bond and Y represents —S(O)$_3$R$^{9e}$, reaction of a compound of formula XIV as defined above with:
(A) for such compounds in which R$^{9e}$ represents H, either SO$_3$ or with SO$_2$ followed by treatment with N-chlorosuccinimide and then hydrolysis;
(B) for such compounds in which R$^{9e}$ is other than H, chlorosulfonic acid followed by reaction with a compound of formula XX as defined below in which R$^{9za}$ represents R$^{9e}$;

(xv) for compounds of formula I in which T represents a single bond and Y represents

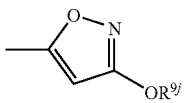

in which R$^{9j}$ represents hydrogen, reaction of a corresponding compound of formula I in which T represents a C$_2$ alkylene group substituted at the carbon atom that is attached to the indole ring system by Z$^1$, in which Z$^1$ represents =O and Y represents —C(O)OR$^{9a}$, in which R$^{9a}$ represents C$_{1-6}$ alkyl with hydroxylamine or an acid addition salt thereof;

(xvi) for compounds of formula I in which T represents a single bond and Y represents

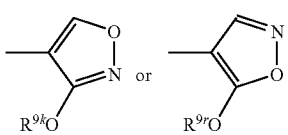

in which R$^{9k}$ and R$^{9r}$ represent hydrogen, reaction of a corresponding compound of formula I in which T represents a C$_1$ alkylene group substituted with G$^1$, in which G$^1$ represents -A$^1$-R$^{12a}$, A$^1$ represents —C(O)A$^2$, A$^2$ represents a single bond and R$^{12a}$ represents H, and Y represents —C(O)OR$^{9a}$, in which R$^{9a}$ represents methyl, or ethyl, respectively, with hydroxylamine or an acid addition salt thereof;

(xvii) for compounds of formula I in which T represents a single bond and Y represents

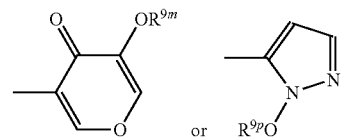

in which R$^{9m}$ and R$^{9p}$ represent hydrogen, reaction of a corresponding compound of formula I in which T represents a single bond, Y represents —B(OR$^{9y}$)$_2$ and R$^{9y}$ represents H with a compound of formula XV in which T represents a single bond, Y$^a$ represents

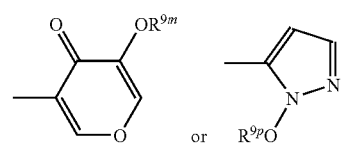

respectively, in which R$^{9m}$ and R$^{9p}$ represent hydrogen, or a protected derivative of either compound;

(xviii) for compounds of formula I in which T represents a single bond and Y represents

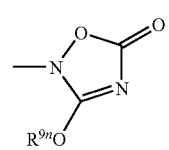

in which R$^{9n}$ represents hydrogen, reaction of a compound of formula XVI,

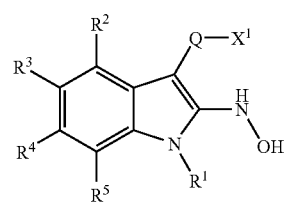

XVI wherein Q, X$^1$, R$^1$, R$^2$, R$^3$, R$^4$ and R$^5$ are as defined in claim 1 with ethoxycarbonyl isocyanate in the presence of a suitable solvent, followed by refluxing in the presence of Triton B and an alcoholic solvent;

(xix) for compounds of formula I in which T represents a single bond and Y represents

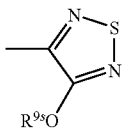

in which $R^{9s}$ represents hydrogen, reaction of a corresponding compound of formula I in which T represents a single bond and Y represents —C(O)OR$^{9a}$, in which R$^{9a}$ represents H with trimethylsilyl chloride (or the like), followed by reaction of the resultant intermediate with N$_4$S$_4$;

(xx) for compounds of formula I in which T represents a single bond and Y represents

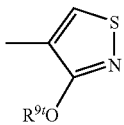

in which $R^{9t}$ represents hydrogen, reaction of a compound of formula XVII,

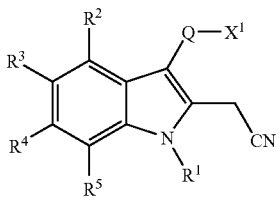
XVII wherein Q, X$^1$, R$^1$, R$^2$, R$^3$, R$^4$ and R$^5$ are as defined in claim 1 with a base and CS$_2$ in the presence of a suitable solvent, oxidation of the resultant intermediate, and finally heating the resultant intermediate in the presence of a strong acid;

(xxi) for compounds of formula I in which T represents a single bond and Y represents

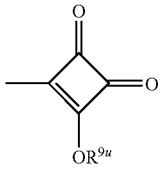

in which $R^{9u}$ represents hydrogen, reaction of a corresponding compound of formula I in which T represents C$_1$ alkylene, Y represents —C(O)OR$^{9a}$ and R$^{9a}$ represents H or an activated derivative thereof with 1,1,2,2-tetraethoxyethene;

(xxii) for compounds of formula I in which T represents a single bond and Y represents

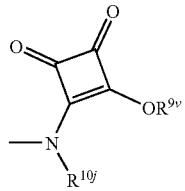

in which $R^{9v}$ and $R^{10j}$ independently represent hydrogen, reaction of a compound of formula XVI as defined above with 3,4-dimethoxycyclobutene-1,2-dione followed by acid;

(xxiii) for compounds of formula I in which T represents a single bond and Y represents

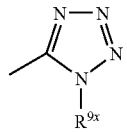

in which $R^{9x}$ represents hydrogen, reaction of a compound of formula XVIII,

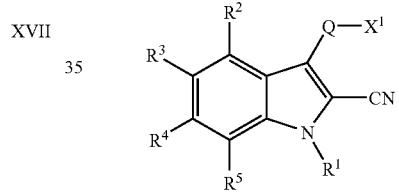
XVIII wherein Q, X$^1$, R$^1$, R$^2$, R$^3$, R$^4$ and R$^5$ are as defined in claim 1 with NaN$_3$;

(xxiv) for compounds of formula I in which T represents optionally substituted C$_{2-8}$ alkenylene or C$_{2-8}$ heteroalkylene (in which a point of unsaturation is between the carbon atoms that are α and β to the indole ring), reaction of a compound of formula XIX,

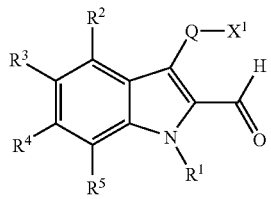
XIX wherein Q, X$^1$, R$^1$, R$^2$, R$^3$, R$^4$ and R$^5$ are as defined in claim 1 with a compound of formula XIXA,

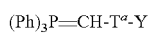
(Ph)$_3$P=CH-T$^a$-Y        XIXA or the like, wherein T$^a$ represents a single bond or optionally substituted C$_{1-6\ alkylene\ or\ C2-6}$ heteroalkylene and Y is as defined in claim 1;

(xxv) for compounds of formula I in which T represents optionally substituted, saturated $C_{2-8}$ alkylene, saturated cycloalkylene, saturated $C_{2-8}$ heteroalkylene, saturated heterocycloalkylene, $C_{2-8}$ alkenylene, cycloalkenylene, $C_{2-8}$ heteroalkenylene or heterocycloalkenylene, reduction of a corresponding compound of formula I in which T represents optionally substituted $C_{2-8}$ alkenylene, cycloalkenylene, $C_{2-8}$ heteroalkenylene, heterocycloalkenylene, $C_{2-8}$ alkynylene, cycloalkynylene, $C_{2-8}$ heteroalkynylene or heterocycloalkynylene (as appropriate);

(xxvi) for compounds of formula I in which Y represents —C(O)OR$^{9a}$, —S(O)$_3$R$^{9e}$, —P(O)(OR$^{9f}$)$_2$, or —B(OR$^{9y}$)$_2$, in which R$^{9a}$, R$^{9e}$, R$^{9f}$ and R$^{9y}$ represent H, hydrolysis of a corresponding compound of formula I in which R$^{9a}$, R$^{9e}$, R$^{9f}$ or R$^{9y}$ (as appropriate) do not represent H, or, for compounds of formula I in which Y represents —P(O)(OR$^{9f}$)$_2$ or —S(O)$_3$R$^{9e}$, in which R$^{9f}$ and R$^{9e}$ represent H, a corresponding compound of formula I in which Y represents either —P(O)(OR$^{9g}$)N(R$^{10h}$)R$^{9h}$, —P(O)(N(R$^{10i}$)R$^{9i}$)$_2$ or —S(O)$_2$N(R$^{10z}$)R$^{9z}$ (as appropriate);

(xxvii) for compounds of formula I in which Y represents —C(O)OR$^{9a}$, —S(O)$_3$R$^{9e}$, —P(O)(OR$^{9f}$)$_2$, —P(O)(OR$^{9g}$)N(R$^{10h}$)R$^{9h}$ or —B(OR$^{9y}$)$_2$ and R$^{9a}$, R$^{9e}$, R$^{9f}$, R$^{9g}$ and R$^{9y}$ do not represent H:
(A) esterification of a corresponding compound of formula I in which R$^{9a}$, R$^{9e}$, R$^{9f}$, R$^{9g}$ and R$^{9y}$ represent H; or
(B) trans-esterification of a corresponding compound of formula I in which R$^{9a}$, R$^{9e}$, R$^{9f}$, R$^{9g}$ and R$^{9y}$ do not represent H (and do not represent the same value of the corresponding R$^{9a}$, R$^{9e}$, R$^{9f}$, R$^{9g}$ and R$^{9y}$ group in the compound of formula I to be prepared), in the presence of a compound of formula XX, $$R^{9za}OH \qquad\qquad XX$$

in which R$^{9za}$ represents R$^{9a}$, R$^{9e}$, R$^{9f}$, R$^{9g}$ or R$^{9y}$ provided that it does not represent H;

(xxviii) for compounds of formula I in which T represents a $C_1$ alkylene group substituted with G$^1$, in which G$^1$ represents -A$^1$-R$^{12a}$, A$^1$ represents —C(O)A$^2$-, A$^2$ represents a single bond and R$^{12a}$ represents H, and Y represents —C(O)OR$^{9a}$, in which R$^{9a}$ is other than H, reaction of a corresponding compound of formula I in which the $C_1$ alkylene group that T represents is unsubstituted, with a $C_{1-6}$ alkyl formate in the presence of a suitable base;

(xxix) for compounds of formula I in which Q and X$^1$ are as defined in claim 1, provided that when X$^1$ or X$^2$ (as appropriate) represents —C(O)OR$^{9a}$, —C(O)N(R$^{10b}$)R$^{9b}$, —C(O)N(H)C(=NR$^{9c}$)N(R$^{10d}$)R$^{9d}$, —S(O)$_3$R$^{9e}$, —P(O)(OR$^{9f}$)$_2$, —P(O)(OR$^{9g}$)N(R$^{10h}$)R$^{9h}$, —P(O)(N(R$^{10i}$)R$^{9i}$)$_2$ or —B(OR$^{9y}$)$_2$, R$^{9a}$ to R$^{9i}$, R$^{9y}$, R$^{10b}$, R$^{10d}$, R$^{10h}$ and R$^{10i}$ are other than H, reaction of a compound of formula XXI,

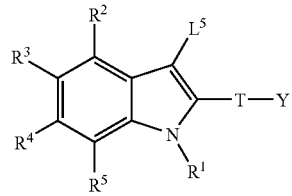

wherein T, Y, R$^1$, R$^2$, R$^3$, R$^4$ and R$^5$ are as defined in claim 1 and L$^5$ is as defined above, with a compound of formula XXII, $$L^6\text{-}Q\text{-}X^{1b} \qquad\qquad XXII$$

wherein X$^{1b}$ represents X$^1$, provided that when X$^1$ or X$^2$ (as appropriate) represents —C(O)OR$^{9a}$, —C(O)N(R$^{10b}$)R$^{9b}$, —C(O)N(H)C(=NR$^{9c}$)N(R$^{10d}$)R$^{9d}$, —S(O)$_3$R$^{9e}$, —P(O)(OR$^{9f}$)$_2$, —P(O)(OR$^{9g}$)N(R$^{10h}$)R$^{9h}$, —P(O)(N(R$^{10i}$)R$^{9i}$)$_2$ or —B(OR$^{9y}$)$_2$, R$^{9a}$ to R$^{9i}$, R$^{9y}$, R$^{10b}$, R$^{10d}$, R$^{10h}$ and R$^{10i}$ are other than H, or a protected derivative thereof, Q is as defined in claim 1 and L$^6$ is as defined above;

(xxx) for compounds of formula I in which Q represents a single bond, X$^1$ represents —C(O)OR$^{9a}$ and R$^{9a}$ represents H, reaction of a compound of formula XXI in which L$^5$ represents either:
(I) an alkali metal; or
(II) —Mg-halide,
with carbon dioxide, followed by acidification;

(xxxi) for compounds of formula I in which Q represents a single bond and X$^1$ represents —C(O)OR$^{9a}$ or —C(O)N(R$^{10b}$)R$^{9b}$, reaction of a corresponding compound of formula XXI in which L$^5$ is a suitable leaving group with CO (or a reagent that is a suitable source of CO), in the presence of a compound of formula XVA as defined above or a compound of formula XXIII as defined below, and an appropriate catalyst system;

(xxxii) for compounds of formula I in which Q represents a single bond, X$^1$ represents —B(OR$^{9y}$)$_2$ and R$^{9y}$ represents H, reaction of a compound of formula XXI as defined above with boronic acid or a protected derivative thereof and an appropriate catalyst system, followed by (if necessary) deprotection;

(xxxiii) for compounds of formula I in which Q represents a single bond and X$^1$ represents —S(O)$_3$R$^{9e}$, reaction of a compound of formula XXI as defined above with:
(A) for such compounds in which R$^{9e}$ represents H, either SO$_3$ (or a suitable source of SO$_3$ such as a SO$_3$*pyridine or SO$_3$*Et$_3$N complex) or with SO$_2$ followed by treatment with N-chlorosuccinimide and then hydrolysis;
(B) for such compounds in which R$^{9e}$ is other than H, chlorosulfonic acid followed by reaction with a compound of formula XX as defined above in which R$^{9za}$ represents R$^{9e}$;

(xxxiv) for compounds of formula I in which X$^1$ or X$^2$ (as appropriate) represents —C(O)OR$^{9a}$, —S(O)$_3$R$^{9e}$, —P(O)(OR$^{9f}$)$_2$ or —B(OR$^{9y}$)$_2$, in which R$^{9a}$, R$^{9e}$, R$^{9f}$ and R$^{9y}$ represent H, hydrolysis of a corresponding compound of formula I in which R$^{9a}$, R$^{9e}$, R$^{9f}$ or R$^{9y}$ (as appropriate) do not represent H, or for compounds of formula I in which X$^1$ or X$^2$ (as appropriate) represents —C(O)OR$^{9a}$ or —P(O)(OR$^{9f}$)$_2$, in which R$^{9a}$ and R$^{9f}$ represent H, a corresponding compound of formula I in which X$^1$ or X$^2$ (as appropriate) represents —C(O)N(H)

$S(O)_2R^{11}$, —$P(O)(OR^{9g})N(R^{10h})R^{9h}$ or —$P(O)(N(R^{10i})R^{9i})_2$ (as appropriate);

(xxxv) for compounds of formula I in which $X^1$ or $X^2$ (as appropriate) represents —$C(O)OR^{9a}$, —$S(O)_3R^{9e}$, —$P(O)(OR^{9f})_2$, —$P(O)(OR^{9g})N(R^{10h})R^{9h}$ or —$B(OR^{9y})_2$ and $R^{9a}$, $R^{9e}$, $R^{9f}$, $R^{9g}$ and $R^{9y}$ do not represent H:
(A) esterification of a corresponding compound of formula I in which $R^{9a}$, $R^{9e}$, $R^{9f}$, $R^{9g}$ and $R^{9y}$ represent H; or
(B) trans-esterification of a corresponding compound of formula I in which $R^{9a}$, $R^{9e}$, $R^{9f}$, $R^{9g}$ and $R^{9y}$ do not represent H (and do not represent the same value of the corresponding $R^{9a}$, $R^{9e}$, $R^{9f}$, $R^{9g}$ and $R^{9y}$ group in the compound of formula I to be prepared),
in the presence of the appropriate alcohol of formula XX as defined above;

(xxxvi) for compounds of formula I in which Q represents a $C_1$ alkylene group substituted with $G^1$, in which $G^1$ represents -$A^1$-$R^{12a}$, $A^1$ represents —$C(O)A^2$-, $A^2$ represents a single bond and $R^{12a}$ represents H, and $X^1$ represents —$C(O)OR^{9a}$, in which $R^{9a}$ is other than H, reaction of a corresponding compound of formula I in which the $C_1$ alkylene group that Q represents is unsubstituted, with a $C_{1-6}$ alkyl formate in the presence of a suitable base; or (xxxvii) for compounds of formula I in which $X^1$ or $X^2$ (as appropriate) represents —$C(O)N(R^{10b})R^{9b}$, —$C(O)N(H)C(=NR^{9c})N(R^{10d})R^{9d}$, —$C(O)N(H)CN$ or —$C(O)N(H)S(O)_2R^{11}$ reaction of a corresponding compound of formula I in which $X^1$ represents —$C(O)OR^9$ with a compound of formula XXIII, $$R^{25}(R^{26})NH \qquad\qquad XXIII$$

wherein $R^{25}$ and $R^{26}$ represent, in the case of a compound of formula I in which $X^1$ or $X^2$ (as appropriate) represents:
(1) —$C(O)N(R^{10b})R^{9b}$, $R^{9b}$ and $R^{10b}$;
(2) —$C(O)N(H)C(=NR^{9c})N(R^{10d})R^{9d}$, —$C(=NR^{9c})N(R^{10d})R^{9d}$ and H;
(3) —$C(O)N(H)CN$, —CN and H; or
(4) —$C(O)N(H)S(O)_2R^{11}$, —$S(O)_2R^{11}$ and H,
respectively, and $R^{9b}$ to $R^{9d}$, $R^{10b}$, $R^{10d}$ and $R^{11}$ are as defined in claim 1.

* * * * *